(12) United States Patent
Gomez et al.

(10) Patent No.: US 11,596,488 B2
(45) Date of Patent: *Mar. 7, 2023

(54) SURGICAL SYSTEM INSTRUMENT MOUNTING

(71) Applicant: INTUITIVE SURGICAL OPERATIONS, INC., Sunnyvale, CA (US)

(72) Inventors: Daniel H. Gomez, Los Gatos, CA (US); Jeffrey D. Brown, Palo Alto, CA (US); Thomas G. Cooper, Menlo Park, CA (US); Eugene F. Duval, Menlo Park, CA (US); Robert E. Holop, Santa Clara, CA (US); Anthony K. McGrogan, San Jose, CA (US); Craig R. Ramstad, Minden, NV (US); Theodore W. Rogers, Alameda, CA (US); Todd R. Solomon, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 16/851,794

(22) Filed: Apr. 17, 2020

(65) Prior Publication Data
US 2020/0246096 A1 Aug. 6, 2020

Related U.S. Application Data

(63) Continuation of application No. 15/718,963, filed on Sep. 28, 2017, now Pat. No. 10,624,672, which is a
(Continued)

(51) Int. Cl.
*A61B 34/00* (2016.01)
*B32B 3/12* (2006.01)
(Continued)

(52) U.S. Cl.
CPC .......... *A61B 34/70* (2016.02); *A61B 1/00135* (2013.01); *A61B 1/00142* (2013.01);
(Continued)

(58) Field of Classification Search
CPC . A61B 34/70; A61B 1/00135; A61B 1/00142; A61B 17/0218; A61B 17/3421;
(Continued)

(56) References Cited

U.S. PATENT DOCUMENTS 4,518,307 A 5/1985 Bloch
5,752,112 A 5/1998 Paddock et al.
(Continued)

FOREIGN PATENT DOCUMENTS

CN 2710567 Y 7/2005
CN 101011292 A 8/2007
(Continued)

OTHER PUBLICATIONS

Co-pending U.S. Appl. No. 11/762,185, filed Jun. 13, 2007.
(Continued)

*Primary Examiner* — Richard G Louis
(74) *Attorney, Agent, or Firm* — Jones Robb, PLLC

(57) ABSTRACT

An instrument manipulator may comprise a frame comprising an outer shell and an inner frame, the inner frame being movably coupled to the outer shell. The instrument manipulator may also include a plurality of actuator outputs protruding in a distal direction from the frame and an instrument support feature coupled to the outer shell. The instrument manipulator may further comprise a latching mechanism, the latching mechanism being configured to move the inner frame, the outer shell, or both relative to one another, so as to operably engage the plurality of actuator outputs with a plurality of actuator inputs of an instrument supported by the instrument support feature.

22 Claims, 50 Drawing Sheets

Related U.S. Application Data continuation of application No. 14/478,311, filed on Sep. 5, 2014, now Pat. No. 9,801,654, which is a continuation of application No. 12/855,452, filed on Aug. 12, 2010, now Pat. No. 8,852,208.

(60) Provisional application No. 61/334,978, filed on May 14, 2010.

(51) Int. Cl.

| | | |
|---|---|---|
| *F16F 1/12* | (2006.01) | |
| *A61B 34/30* | (2016.01) | |
| *A61B 34/35* | (2016.01) | |
| *A61B 34/37* | (2016.01) | |
| *A61B 46/10* | (2016.01) | |
| *A61B 17/34* | (2006.01) | |
| *A61B 46/23* | (2016.01) | |
| *A61B 50/00* | (2016.01) | |
| *A61B 90/98* | (2016.01) | |
| *H01F 5/02* | (2006.01) | |
| *H01F 5/04* | (2006.01) | |
| *H01F 27/28* | (2006.01) | |
| *H04N 5/225* | (2006.01) | |
| *H04N 5/232* | (2006.01) | |
| *H05K 1/18* | (2006.01) | |
| *A61B 1/00* | (2006.01) | |
| *A61B 50/20* | (2016.01) | |
| *A61B 50/30* | (2016.01) | |
| *B25J 15/04* | (2006.01) | |
| *A61B 17/02* | (2006.01) | |
| *A61M 13/00* | (2006.01) | |
| *A61B 17/00* | (2006.01) | |
| *A61B 90/50* | (2016.01) | |
| *G03B 5/02* | (2021.01) | |

(52) U.S. Cl.
CPC ...... *A61B 17/0218* (2013.01); *A61B 17/3421* (2013.01); *A61B 17/3423* (2013.01); *A61B 17/3474* (2013.01); *A61B 34/00* (2016.02); *A61B 34/30* (2016.02); *A61B 34/35* (2016.02); *A61B 34/37* (2016.02); *A61B 46/10* (2016.02); *A61B 46/23* (2016.02); *A61B 50/00* (2016.02); *A61B 50/20* (2016.02); *A61B 50/30* (2016.02); *A61B 90/98* (2016.02); *A61M 13/003* (2013.01); *B25J 15/04* (2013.01); *B32B 3/12* (2013.01); *F16F 1/121* (2013.01); *H01F 5/02* (2013.01); *H01F 5/04* (2013.01); *H01F 27/2823* (2013.01); *H04N 5/2252* (2013.01); *H04N 5/2253* (2013.01); *H04N 5/2254* (2013.01); *H04N 5/2257* (2013.01); *H04N 5/23287* (2013.01); *H05K 1/18* (2013.01); *A61B 2017/00477* (2013.01); *A61B 2017/3445* (2013.01); *A61B 2017/3447* (2013.01); *A61B 2034/302* (2016.02); *A61B 2034/306* (2016.02); *A61B 2050/3008* (2016.02); *A61B 2090/5025* (2016.02); *G03B 5/02* (2013.01); *G03B 2205/0015* (2013.01); *G03B 2205/0069* (2013.01); *H01F 2005/027* (2013.01); *Y10T 74/20305* (2015.01)

(58) Field of Classification Search
CPC . A61B 17/3423; A61B 17/3474; A61B 34/00; A61B 34/30; A61B 34/35; A61B 34/37; A61B 46/23; A61B 46/10; A61B 50/00; A61B 50/20; A61B 50/30; A61B 90/98; A61B 2017/00477; A61B 2017/3445; A61B 2017/3447; A61B 2034/302; A61B 2034/306; A61B 2050/3008; A61B 2090/5025; A61B 90/08; A61M 13/003; B25J 15/04; B32B 3/12; F16F 1/121; H01F 5/02; H01F 5/04; H01F 27/2823; H01F 2005/027; H04N 5/2252; H04N 5/2253; H04N 2/2254; H04N 5/2257; H04N 5/23287; H05K 1/18; G03B 5/02; G03B 2205/0015; G03B 2205/0069; Y10T 74/20305

See application file for complete search history.

(56) References Cited

U.S. PATENT DOCUMENTS

| | | |
|---|---|---|
| 5,755,713 A | 5/1998 | Bilof et al. |
| 5,827,266 A | 10/1998 | Harel et al. |
| 5,907,664 A | 5/1999 | Wang et al. |
| 6,007,550 A | 12/1999 | Wang et al. |
| 6,030,130 A | 2/2000 | Paddock et al. |
| 6,132,368 A | 10/2000 | Cooper |
| 6,309,397 B1 | 10/2001 | Julian et al. |
| 6,347,892 B1 | 2/2002 | Paddock et al. |
| 6,364,888 B1 | 4/2002 | Niemeyer et al. |
| 6,371,952 B1 | 4/2002 | Madhani et al. |
| 6,451,027 B1 | 9/2002 | Cooper et al. |
| 6,491,701 B2 | 12/2002 | Tierney et al. |
| 6,574,355 B2 | 6/2003 | Green |
| 6,575,644 B2 | 6/2003 | Paddock et al. |
| 6,578,967 B1 | 6/2003 | Paddock et al. |
| 6,671,581 B2 | 12/2003 | Niemeyer et al. |
| 6,817,974 B2 | 11/2004 | Cooper et al. |
| 6,866,671 B2 | 3/2005 | Tierney et al. |
| 7,175,456 B2 | 2/2007 | Moreno et al. |
| 7,320,700 B2 | 1/2008 | Cooper et al. |
| 7,371,028 B2 | 5/2008 | Gordon et al. |
| 7,594,912 B2 | 9/2009 | Cooper et al. |
| 7,725,214 B2 | 5/2010 | Diolaiti |
| 8,852,208 B2 | 10/2014 | Gomez et al. |
| 8,945,148 B2 * | 2/2015 | Solomon ............ A61B 1/00142 606/1 |
| 9,801,654 B2 | 10/2017 | Gomez et al. |
| 9,955,996 B2 | 5/2018 | McGrogan et al. |
| 10,624,672 B2 * | 4/2020 | Gomez ............ A61B 17/3421 |
| 10,856,946 B2 | 12/2020 | Solomon et al. |
| 10,918,449 B2 | 2/2021 | Solomon et al. |
| 2002/0042620 A1 | 4/2002 | Julian et al. |
| 2005/0059960 A1 | 3/2005 | Simaan et al. |
| 2005/0251156 A1 | 11/2005 | Toth et al. |
| 2006/0013523 A1 | 1/2006 | Childers et al. |
| 2006/0161136 A1 | 7/2006 | Anderson et al. |
| 2006/0161138 A1 | 7/2006 | Orban et al. |
| 2006/0167440 A1 | 7/2006 | Cooper et al. |
| 2006/0235436 A1 | 10/2006 | Anderson et al. |
| 2007/0005045 A1 | 1/2007 | Mintz et al. |
| 2007/0016174 A1 | 1/2007 | Millman et al. |
| 2007/0089557 A1 | 4/2007 | Solomon et al. |
| 2007/0119274 A1 | 5/2007 | Devengenzo et al. |
| 2007/0137371 A1 | 6/2007 | Devengenzo et al. |
| 2007/0142969 A1 | 6/2007 | Devengenzo et al. |
| 2007/0156019 A1 | 7/2007 | Larkin et al. |
| 2007/0173789 A1 | 7/2007 | Schena |
| 2007/0233052 A1 | 10/2007 | Brock |
| 2007/0283970 A1 | 12/2007 | Mohr et al. |
| 2007/0287884 A1 | 12/2007 | Schena |
| 2007/0287889 A1 | 12/2007 | Mohr |
| 2007/0287992 A1 | 12/2007 | Diolaiti et al. |
| 2008/0004634 A1 | 1/2008 | Farritor et al. |
| 2008/0015611 A1 | 1/2008 | Jinno et al. |
| 2008/0058861 A1 | 3/2008 | Cooper et al. |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin et al. |
| 2008/0065099 A1 | 3/2008 | Cooper et al. |
| 2008/0065100 A1 | 3/2008 | Larkin |

(56) References Cited

U.S. PATENT DOCUMENTS

| | | |
|---|---|---|
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065109 A1 | 3/2008 | Larkin et al. |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0103491 A1 | 5/2008 | Omori et al. |
| 2008/0151041 A1 | 6/2008 | Shafer et al. |
| 2008/0177284 A1 | 7/2008 | Lee et al. |
| 2008/0215065 A1 | 9/2008 | Wang et al. |
| 2008/0235436 A1 | 9/2008 | Zimmer et al. |
| 2008/0243106 A1 | 10/2008 | Coe et al. |
| 2008/0287963 A1 | 11/2008 | Rogers et al. |
| 2009/0041565 A1 | 2/2009 | Rodriguez |
| 2009/0163948 A1 | 6/2009 | Sunaoshi et al. |
| 2009/0192524 A1 | 7/2009 | Itkowitz et al. |
| 2009/0248039 A1 | 10/2009 | Cooper et al. |
| 2009/0248040 A1 | 10/2009 | Cooper et al. |
| 2009/0314131 A1 | 12/2009 | Bailey |
| 2009/0322001 A1 | 12/2009 | Luke et al. |
| 2009/0326322 A1 | 12/2009 | Diolaiti et al. |
| 2009/0326552 A1 | 12/2009 | Diolaiti |
| 2009/0326553 A1 | 12/2009 | Mustufa et al. |
| 2010/0111645 A1 | 5/2010 | Al-Mouhamed et al. |
| 2010/0170519 A1 | 7/2010 | Romo et al. |
| 2010/0204713 A1 | 8/2010 | Ruiz Morales |
| 2010/0274087 A1 | 10/2010 | Diolaiti et al. |
| 2010/0318101 A1 | 12/2010 | Choi et al. |
| 2010/0332033 A1 | 12/2010 | Diolaiti et al. |
| 2011/0015650 A1 | 1/2011 | Choi et al. |
| 2011/0040305 A1 | 2/2011 | Gomez et al. |
| 2011/0040404 A1 | 2/2011 | Diolaiti et al. |
| 2011/0082365 A1 | 4/2011 | McGrogan et al. |
| 2011/0152879 A1 | 6/2011 | Williams et al. |
| 2011/0196419 A1 | 8/2011 | Cooper |
| 2011/0201883 A1 | 8/2011 | Cooper et al. |
| 2011/0202068 A1 | 8/2011 | Diolaiti et al. |
| 2011/0277576 A1 | 11/2011 | Cooper |
| 2011/0277579 A1 | 11/2011 | Anderson et al. |
| 2011/0277580 A1 | 11/2011 | Cooper et al. |
| 2011/0277775 A1 | 11/2011 | Holop et al. |
| 2011/0277776 A1 | 11/2011 | McGrogan et al. |
| 2011/0282351 A1 | 11/2011 | Cooper et al. |
| 2011/0282357 A1 | 11/2011 | Rogers et al. |
| 2011/0282359 A1 | 11/2011 | Duval |
| 2012/0010628 A1 | 1/2012 | Cooper et al. |
| 2018/0014852 A1 | 1/2018 | Gomez et al. |
| 2018/0214176 A1 | 8/2018 | Solomon et al. |
| 2018/0353204 A1 | 12/2018 | Solomon et al. |
| 2021/0220066 A1 | 7/2021 | Solomon et al. |

FOREIGN PATENT DOCUMENTS

| | | |
|---|---|---|
| CN | 101474090 A | 7/2009 |
| JP | H11123675 A | 5/1999 |
| JP | 2003024336 A | 1/2003 |
| JP | 2007029274 A | 2/2007 |
| JP | 2009148859 A | 7/2009 |
| JP | 2009525098 A | 7/2009 |
| KR | 20080072667 A | 8/2008 |
| KR | 20080100211 A | 11/2008 |
| WO | WO-9825666 A1 | 6/1998 |
| WO | WO-200121085 A1 | 3/2001 |
| WO | WO-0241759 A3 | 8/2002 |
| WO | WO-2006039092 A2 | 4/2006 |
| WO | WO-2006079108 A1 | 7/2006 |
| WO | WO-2006124390 A2 | 11/2006 |
| WO | WO-2007041094 A1 | 4/2007 |
| WO | WO-2007075864 A1 | 7/2007 |
| WO | WO-2007114975 A2 | 10/2007 |
| WO | WO-2007126443 A2 | 11/2007 |
| WO | WO-2007146987 A2 | 12/2007 |
| WO | WO-2009002701 A2 | 12/2008 |
| WO | WO-2009061915 A2 | 5/2009 |
| WO | WO-2009102102 A1 | 8/2009 |
| WO | WO-2009151205 A1 | 12/2009 |

OTHER PUBLICATIONS

Co-pending U.S. Appl. No. 60/813,028, filed Jun. 13, 2006.
Co-pending U.S. Appl. No. 60/813,029, filed Jun. 13, 2006.
Co-pending U.S. Appl. No. 60/813,030, filed Jun. 13, 2006.
Co-pending U.S. Appl. No. 60/813,075, filed Jun. 13, 2006.
Co-pending U.S. Appl. No. 60/813,125, filed Jun. 13, 2006.
Co-pending U.S. Appl. No. 60/813,126, filed Jun. 13, 2006.
Co-pending U.S. Appl. No. 60/813,129, filed Jun. 13, 2006.
Co-pending U.S. Appl. No. 60/813,131, filed Jun. 13, 2006.
Co-pending U.S. Appl. No. 60/813,172, filed Jun. 13, 2006.
Co-pending U.S. Appl. No. 60/813,173, filed Jun. 13, 2006.
Co-pending U.S. Appl. No. 60/813,198, filed Jun. 13, 2006.
Co-pending U.S. Appl. No. 60/813,207, filed Jun. 13, 2006.
Co-pending U.S. Appl. No. 60/813,328, filed Jun. 13, 2006.
Co-pending U.S. Appl. No. 61/334,978, filed May 14, 2010.
Extended European Search Report for Application No. EP17188902.5, dated Jan. 12, 2018, 10 pages.
PCT/US2011/035109 International Search Report and Written Opinion of the International Searching Authority, dated Aug. 2, 2011, 9 pages.
PCT/US2011/035117 International Search Report and Written Opinion of the International Searching Authority, dated Aug. 2, 2011, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European search report for Application No. EP20155212.2, dated Jun. 9, 2020, 12 pages.

\* cited by examiner

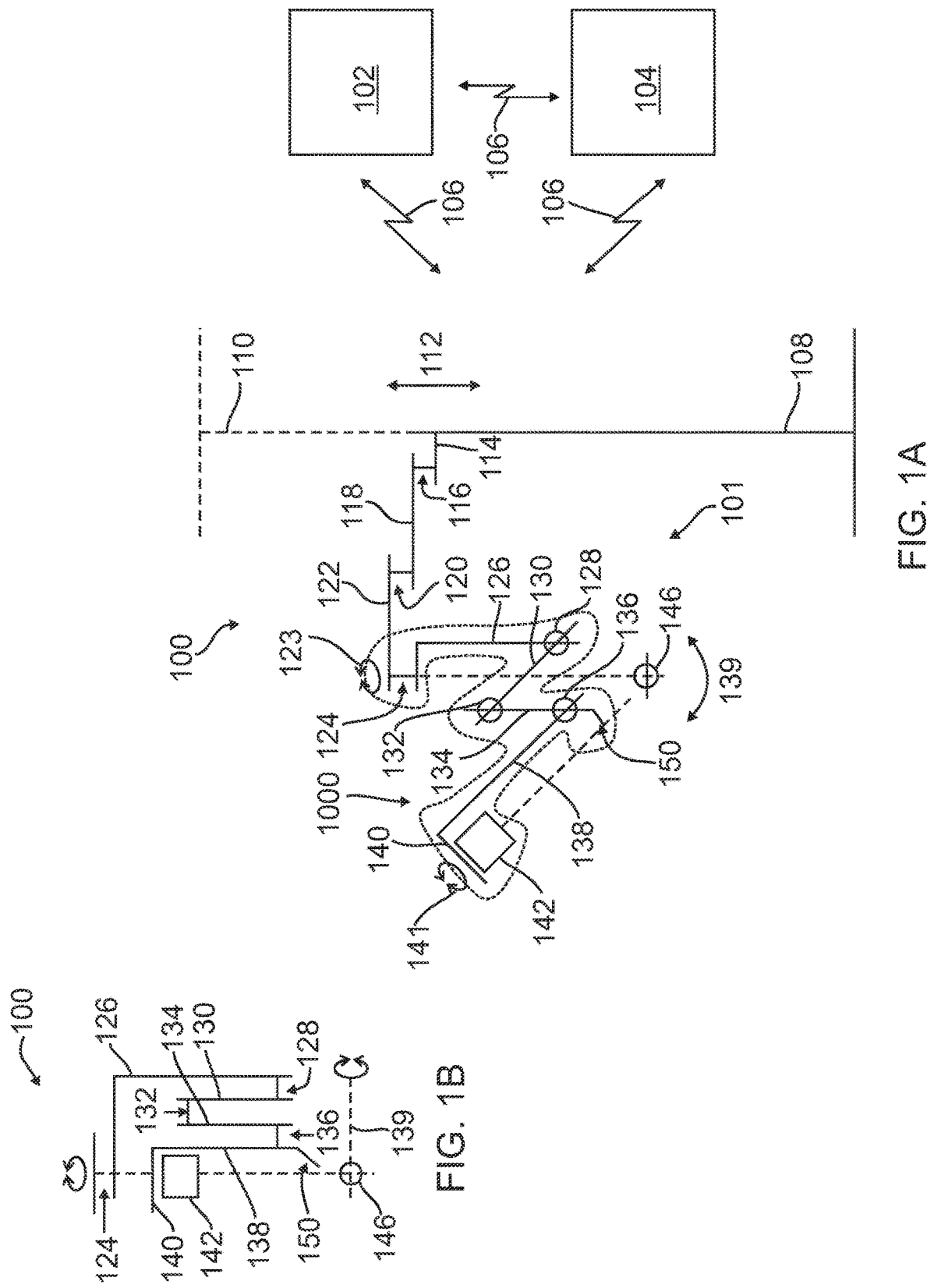

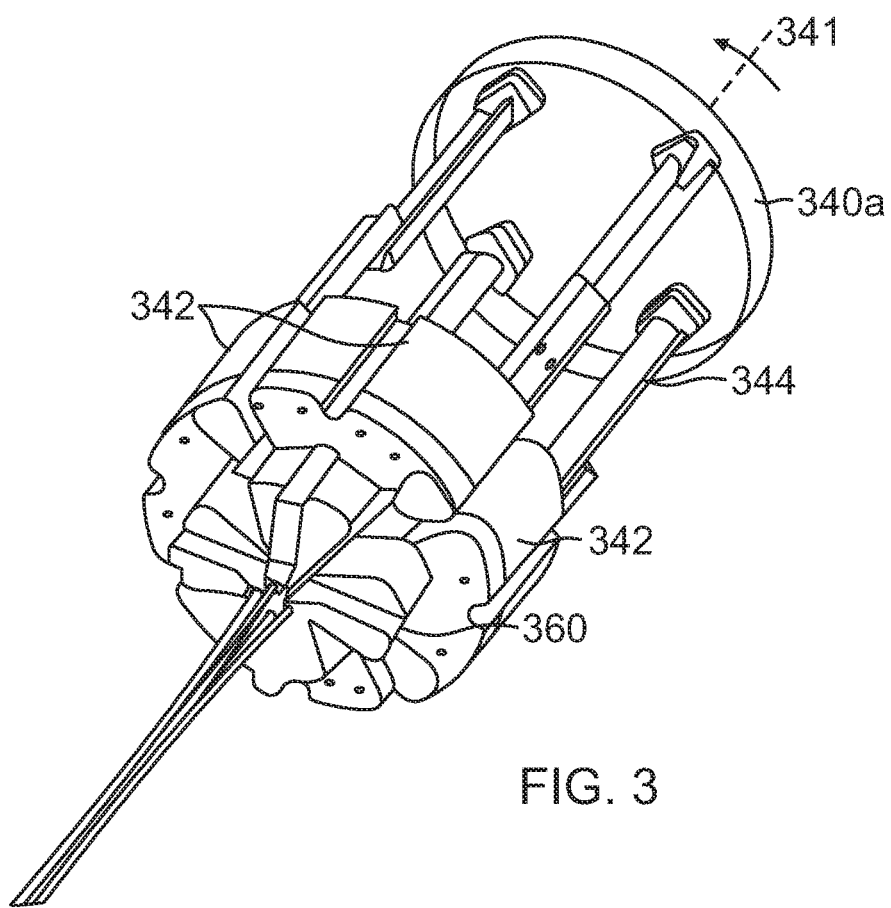
FIG. 3
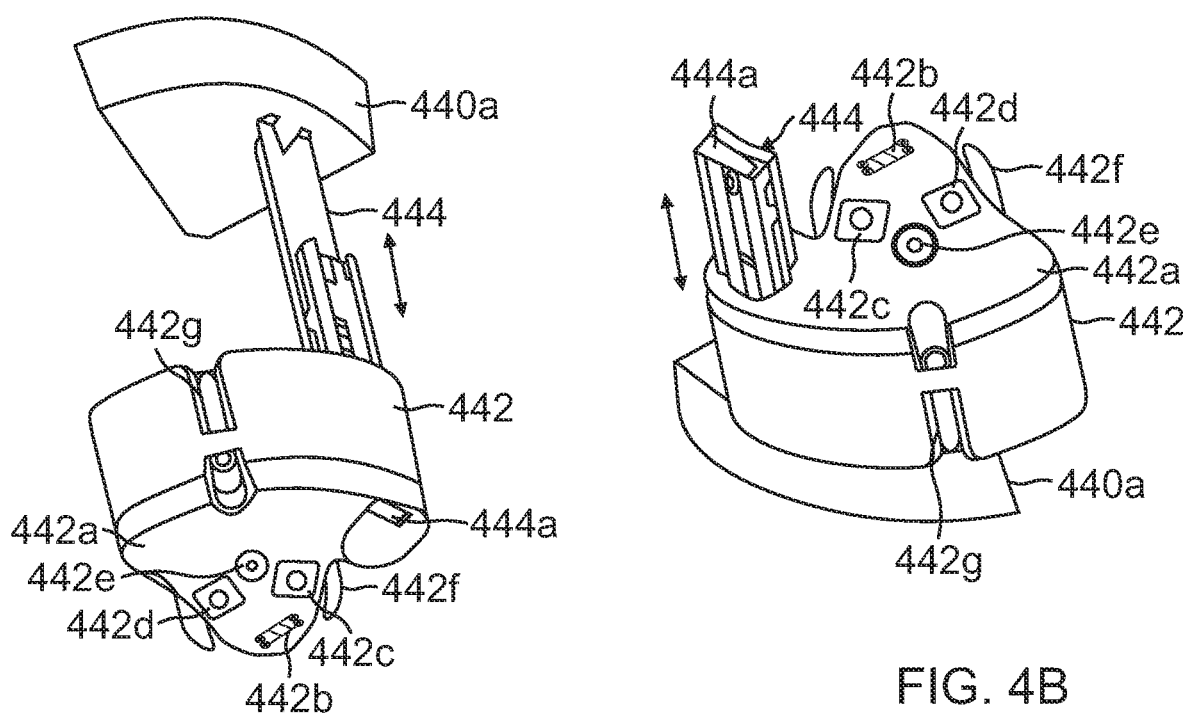
FIG. 4A
FIG. 4B

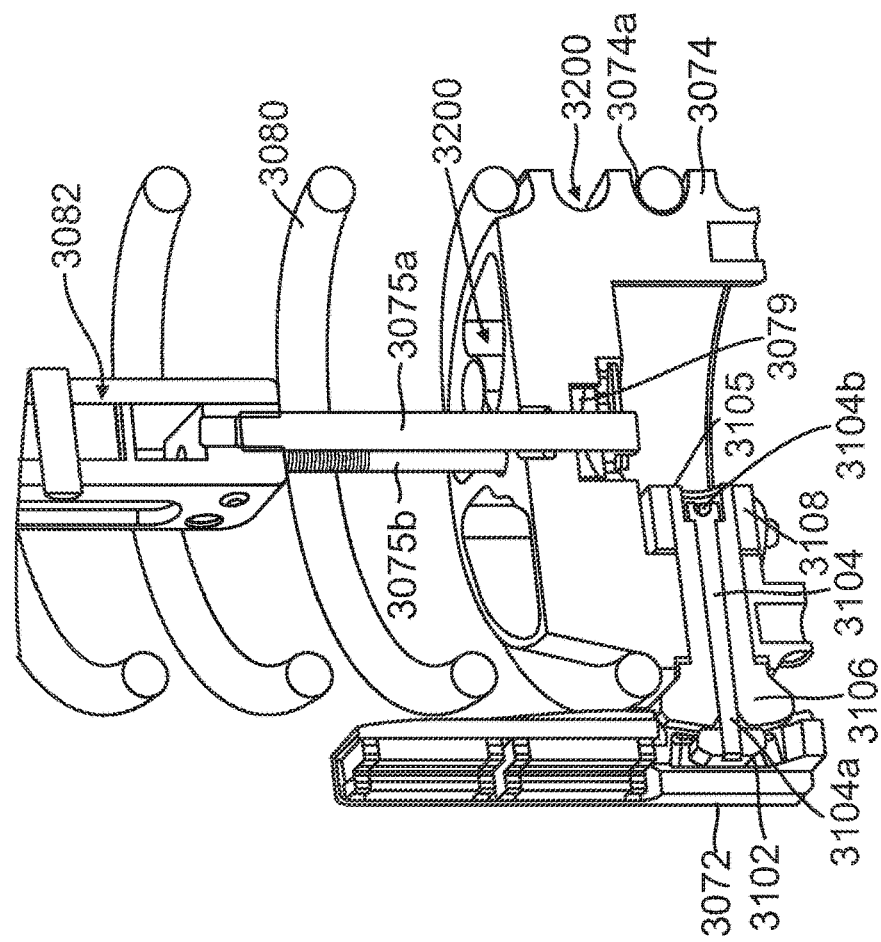
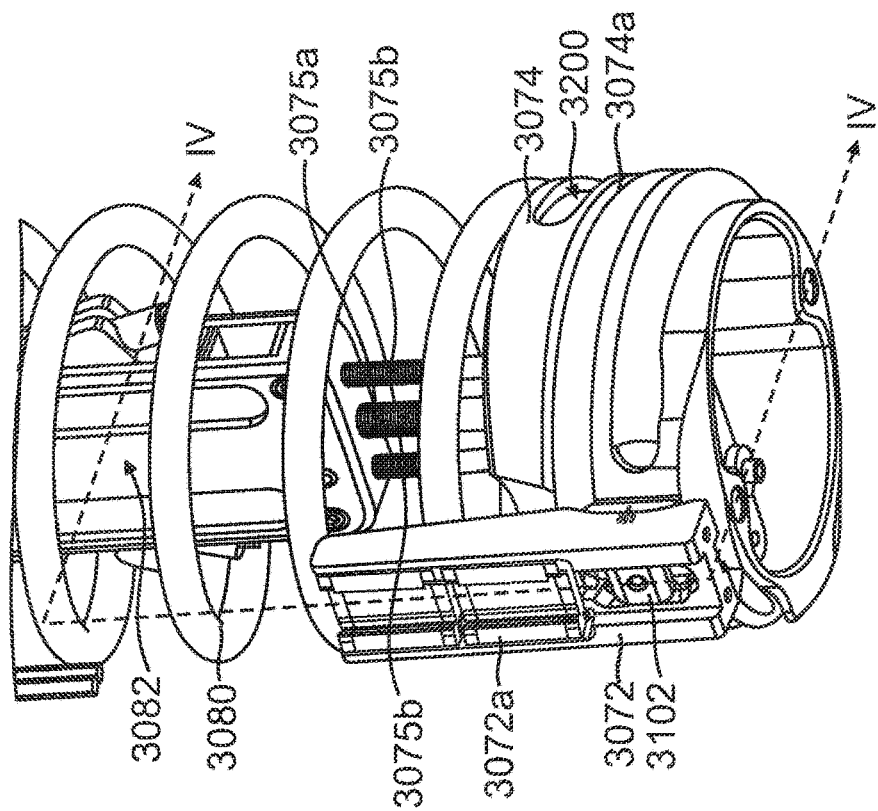
FIG. 32B
FIG. 32A

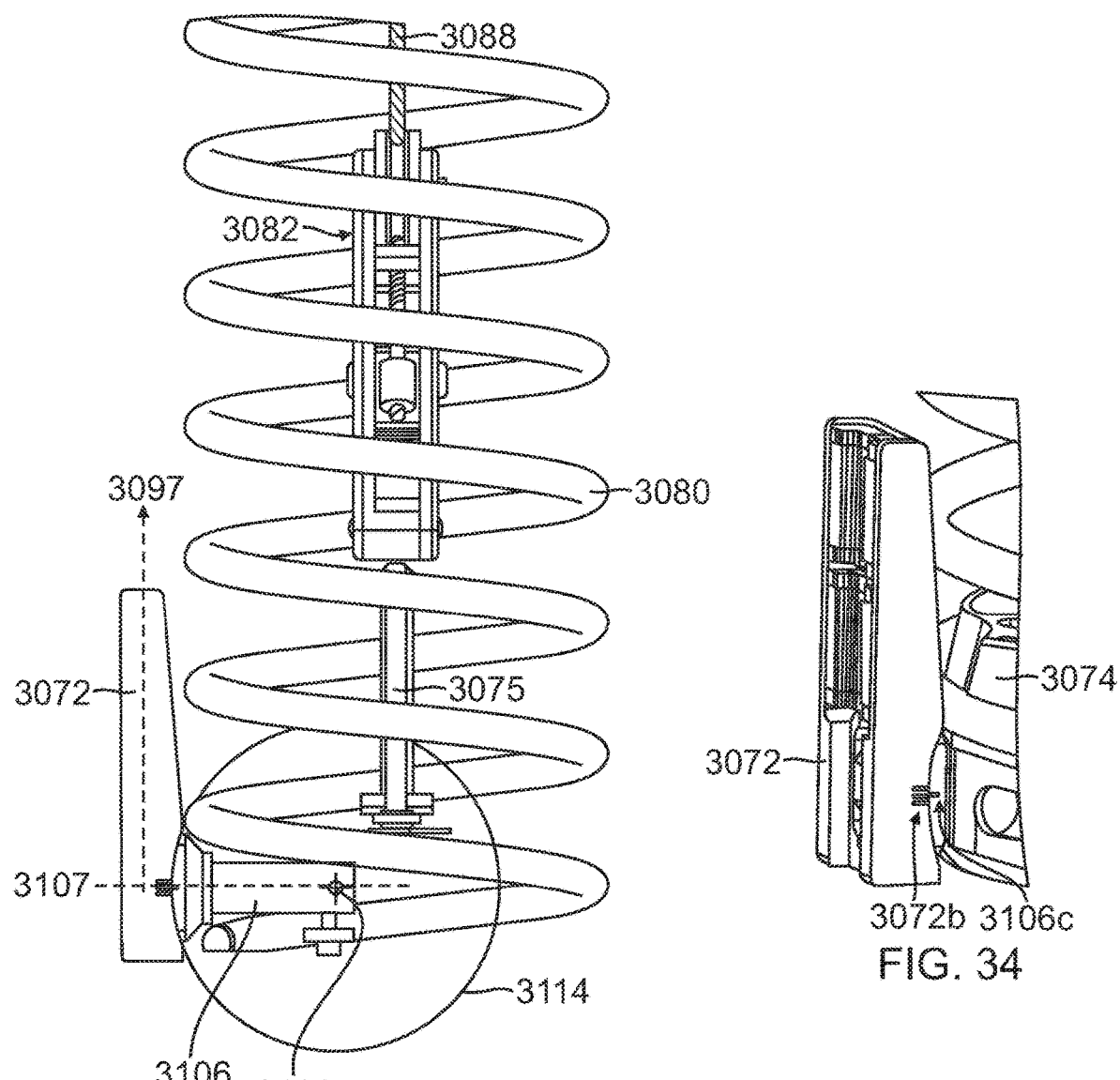
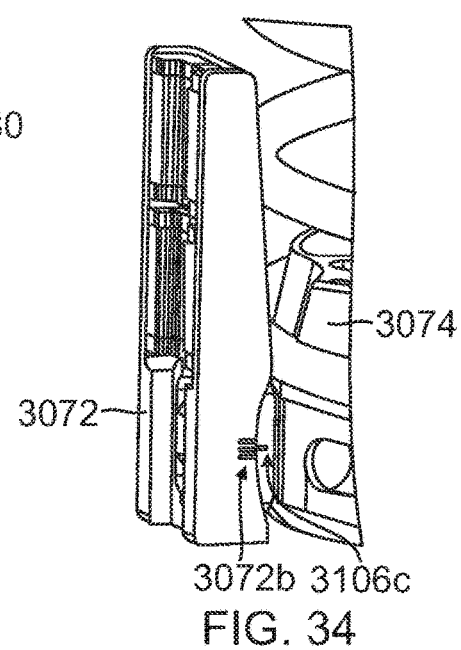
FIG. 34
FIG. 33
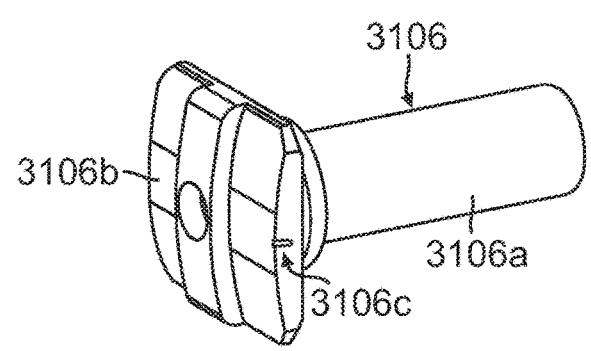
FIG. 35

SURGICAL SYSTEM INSTRUMENT MOUNTING

CROSS-REFERENCE TO RELATED APPLICATIONS

This application is a continuation of U.S. application Ser. No. 15/718,963, filed Sep. 28, 2017, which is a continuation of U.S. application Ser. No. 14/478,311, filed Sep. 5, 2014 (now U.S. Pat. No. 9,801,654), which is a continuation of U.S. application Ser. No. 12/855,452, filed Aug. 12, 2010 (now U.S. Pat. No. 8,852,208), which claims the benefit of U.S. Provisional Application No. 61/334,978, filed May 14, 2010, each of which is incorporated herein by reference in its entirety.

This application is related to U.S. patent application Ser. No. 11/762,165, filed Jun. 13, 2007, which is incorporated by reference herein for all purposes. U.S. patent application Ser. No. 11/762,165 claimed the priority benefit of the following U.S. provisional patent applications, all of which are incorporated by reference herein: 60/813,028 entitled "Single port system 2" filed Jun. 13, 2006 by Cooper et al.; Ser. No. 60/813,029 entitled "Single port surgical system 1" filed Jun. 13, 2006 by Cooper; 60/813,030 entitled "Independently actuated optical train" filed Jun. 13, 2006 by Larkin et al.; Ser. No. 60/813,075 entitled "Modular cannula architecture" filed Jun. 13, 2006 by Larkin et al.; Ser. No. 60/813,125 entitled "Methods for delivering instruments to a surgical site with minimal disturbance to intermediate structures" filed Jun. 13, 2006 by Larkin et al.; Ser. No. 60/813,126 entitled "Rigid single port surgical system" filed Jun. 13, 2006 by Cooper; 60/813,129 entitled "Minimum net force actuation" filed Jun. 13, 2006 by Cooper et al.; Ser. No. 60/813,131 entitled "Side working tools and camera" filed Jun. 13, 2006 by Duval et al.; Ser. No. 60/813,172 entitled "Passing cables through joints" filed Jun. 13, 2006 by Cooper; 60/813,173 entitled "Hollow smoothly bending instrument joints" filed Jun. 13, 2006 by Larkin et al.; Ser. No. 60/813,198 entitled "Retraction devices and methods" filed Jun. 13, 2006 by Mohr et al.; Ser. No. 60/813,207 entitled "Sensory architecture for endoluminal robots" filed Jun. 13, 2006 by Diolaiti et al.; and 60/813,328 entitled "Concept for single port laparoscopic surgery" filed Jun. 13, 2006 by Mohr et al.

In addition, this application is related to the following pending U.S. patent applications, all of which are incorporated by reference herein: Ser. No. 11/762,217 entitled "Retraction of tissue for single port entry, robotically assisted medical procedures" by Mohr; Ser. No. 11/762,222 entitled "Bracing of bundled medical devices for single port entry, robotically assisted medical procedures" by Mohr et al.; Ser. No. 11/762,231 entitled "Extendable suction surface for bracing medical devices during robotically assisted medical procedures" by Schena; Ser. No. 11/762,236 entitled "Control system configured to compensate for non-ideal actuator-to-joint linkage characteristics in a medical robotic system" by Diolaiti et al.; Ser. No. 11/762,185 entitled "Surgical instrument actuation system" by Cooper et al.; Ser. No. 11/762,172 entitled "Surgical instrument actuator" by Cooper et al.; Ser. No. 11/762,161 entitled "Minimally invasive surgical instrument advancement" by Larkin et al.; Ser. No. 11/762,158 entitled "Surgical instrument control and actuation" by Cooper et al.; Ser. No. 11/762,154 entitled "Surgical instrument with parallel motion mechanism" by Cooper; Ser. No. 11/762,149 entitled "Minimally invasive surgical apparatus with side exit instruments" by Larkin; Ser. No. 11/762,170 entitled "Minimally invasive surgical apparatus with side exit instruments" by Larkin; Ser. No. 11/762,143 entitled "Minimally invasive surgical instrument system" by Larkin; Ser. No. 11/762,135 entitled "Side looking minimally invasive surgery instrument assembly" by Cooper et al.; Ser. No. 11/762,132 entitled "Side looking minimally invasive surgery instrument assembly" by Cooper et al.; Ser. No. 11/762,127 entitled "Guide tube control of minimally invasive surgical instruments" by Larkin et al.; Ser. No. 11/762,123 entitled "Minimally invasive surgery guide tube" by Larkin et al.; Ser. No. 11/762,120 entitled "Minimally invasive surgery guide tube" by Larkin et al.; Ser. No. 11/762,118 entitled "Minimally invasive surgical retractor system" by Larkin; Ser. No. 11/762,114 entitled "Minimally invasive surgical illumination" by Schena et al.; Ser. No. 11/762,110 entitled "Retrograde instrument" by Duval et al.; Ser. No. 11/762,204 entitled "Retrograde instrument" by Duval et al.; Ser. No. 11/762,202 entitled "Preventing instrument/tissue collisions" by Larkin; Ser. No. 11/762,189 entitled "Minimally invasive surgery instrument assembly with reduced cross section" by Larkin et al.; Ser. No. 11/762,191 entitled "Minimally invasive surgical system" by Larkin et al.; Ser. No. 11/762,196 entitled "Minimally invasive surgical system" by Duval et al.; and Ser. No. 11/762,200 entitled "Minimally invasive surgical system" by Diolaiti.

This application is also related to the following U.S. patent applications, all of which are incorporated by reference herein: U.S. patent application Ser. No. 12/163,051 (filed Jun. 27, 2008; entitled "Medical Robotic System with Image Referenced Camera Control Using Partitionable Orientation and Translational Modes"); U.S. patent application Ser. No. 12/163,069 (filed Jun. 27, 2008; entitled "Medical Robotic System Having Entry Guide Controller with Instrument Tip Velocity Limiting"); U.S. patent application Ser. No. 12/494,695 (filed Jun. 30, 2009; entitled "Control of Medical Robotic System Manipulator About Kinematic Singularities"); U.S. patent application Ser. No. 12/541,913 (filed Aug. 15, 2009; entitled "Smooth Control of an Articulated Instrument Across Areas with Different Work Space Conditions"); U.S. patent application Ser. No. 12/571,675 (filed Oct. 1, 2009; entitled "Laterally Fenestrated Cannula"); U.S. patent application Ser. No. 12/613,328 (filed Nov. 5, 2009; entitled "Controller Assisted Reconfiguration of an Articulated Instrument During Movement Into and Out Of an Entry Guide"); U.S. patent application Ser. No. 12/645,391 (filed Dec. 22, 2009; entitled "Instrument Wrist with Cycloidal Surfaces"); U.S. patent application Ser. No. 12/702,200 (filed Feb. 8, 2010; entitled "Direct Pull Surgical Gripper"); U.S. patent application Ser. No. 12/704,669 (filed Feb. 12, 2010; entitled "Medical Robotic System Providing Sensory Feedback Indicating a Difference Between a Commanded State and a Preferred Pose of an Articulated Instrument"); U.S. patent application Ser. No. 12/163,087 (filed Jun. 27, 2008; entitled "Medical Robotic System Providing an Auxiliary View of Articulatable Instruments Extending Out Of a Distal End of an Entry Guide"); U.S. patent application Ser. No. 12/780,071 (filed May 14, 2010; entitled "Medical Robotic System with Coupled Control Modes"); U.S. patent application Ser. No. 12/780,747 (filed May 14, 2010; entitled "Cable Re-ordering Device"); U.S. patent application Ser. No. 12/780,758 (filed May 14, 2010; entitled "Force Transmission for Robotic Surgical Instrument"); U.S. patent application Ser. No. 12/780,773 (filed May 14, 2010; entitled "Overforce Protection Mechanism"); U.S. patent application Ser. No. 12/832,580 (filed Jul. 8, 2010; entitled "Sheaths for Jointed Instruments"); U.S. patent application Ser. No. 12/855,499 (filed Aug. 12, 2010;

entitled "Surgical System Sterile Drape"); U.S. patent application Ser. No. 12/855,488 (filed Aug. 12, 2010; entitled "Surgical System Entry Guide"); U.S. patent application Ser. No. 12/855,413 (filed Aug. 12, 2010; entitled "Surgical System Instrument Manipulator Actuator Suspension"); U.S. patent application Ser. No. 12/855,434 (filed Aug. 12, 2010; entitled "Surgical System Architecture"); U.S. patent application Ser. No. 12/855,475 (filed Aug. 12, 2010; entitled "Surgical System Counterbalance"); and U.S. patent application Ser. No. 12/855,461 (filed Aug. 12, 2010; entitled "Surgical System Instrument Sterile Adapter").

BACKGROUND

In robotically-assisted or telerobotic surgery, the surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each performs various functions for the surgeon, e.g., holding or driving a needle, grasping a blood vessel, or dissecting, cauterizing or coagulating tissue.

The number of degrees of freedom (DOFs) is the number of independent variables that uniquely identify the pose/configuration of a telerobotic system. Since robotic manipulators are kinematic chains that map the (input) joint space into the (output) Cartesian space, the notion of DOF can be expressed in any of these two spaces. In particular, the set of joint DOFs is the set of joint variables for all the independently controlled joints. Without loss of generality, joints are mechanisms that provide, e.g., a single translational (prismatic joints) or rotational (revolute joints) DOF. Any mechanism that provides more than one DOF motion is considered, from a kinematic modeling perspective, as two or more separate joints. The set of Cartesian DOFs is usually represented by the three translational (position) variables (e.g., surge, heave, sway) and by the three rotational (orientation) variables (e.g. Euler angles or roll/pitch/yaw angles) that describe the position and orientation of an end effector (or tip) frame with respect to a given reference Cartesian frame.

For example, a planar mechanism with an end effector mounted on two independent and perpendicular rails has the capability of controlling the x/y position within the area spanned by the two rails (prismatic DOFs). If the end effector can be rotated around an axis perpendicular to the plane of the rails, there are then three input DOFs (the two rail positions and the yaw angle) that correspond to three output DOFs (the x/y position and the orientation angle of the end effector).

Although the number of non-redundant Cartesian DOFs that describe a body within a Cartesian reference frame, in which all the translational and orientational variables are independently controlled, can be six, the number of joint DOFs is generally the result of design choices that involve considerations of the complexity of the mechanism and the task specifications. Accordingly, the number of joint DOFs can be more than, equal to, or less than six. For non-redundant kinematic chains, the number of independently controlled joints is equal to the degree of mobility for the end effector frame. For a certain number of prismatic and revolute joint DOFs, the end effector frame will have an equal number of DOFs (except when in singular configurations) in Cartesian space that will correspond to a combination of translational (x/y/z position) and rotational (roll/pitch/yaw orientation angle) motions.

The distinction between the input and the output DOFs is extremely important in situations with redundant or "defective" kinematic chains (e.g., mechanical manipulators). In particular, "defective" manipulators have fewer than six independently controlled joints and therefore do not have the capability of fully controlling end effector position and orientation. Instead, defective manipulators are limited to controlling only a subset of the position and orientation variables. On the other hand, redundant manipulators have more than six joint DOFs. Thus, a redundant manipulator can use more than one joint configuration to establish a desired 6-DOF end effector pose. In other words, additional degrees of freedom can be used to control not just the end effector position and orientation but also the "shape" of the manipulator itself. In addition to the kinematic degrees of freedom, mechanisms may have other DOFs, such as the pivoting lever movement of gripping jaws or scissors blades.

Telerobotic surgery through remote manipulation has been able to reduce the size and number of incisions required in surgery to enhance patient recovery while also helping to reduce patient trauma and discomfort. However, telerobotic surgery has also created many new challenges. Robotic manipulators adjacent the patient have made patient access sometimes difficult for patient-side staff, and for robots designed particularly for single port surgery, access to the single port is of vital importance. For example, a surgeon will typically employ a large number of different surgical instruments/tools during a procedure and ease of access to the manipulator and single port and ease of instrument exchange are highly desirable.

Another challenge results from the fact that a portion of the electromechanical surgical manipulator will be positioned adjacent the operation site. Accordingly, the surgical manipulator may become contaminated during surgery and is typically disposed of or sterilized between operations. From a cost perspective, it would be preferable to sterilize the device. However, the servo motors, sensors, encoders, and electrical connections that are necessary to robotically control the motors typically cannot be sterilized using conventional methods, e.g., steam, heat and pressure, or chemicals, because the system parts would be damaged or destroyed in the sterilization process.

A sterile drape has been previously used to cover the surgical manipulator and has previously included holes through which an adaptor (for example a wrist unit adaptor or a cannula adaptor) would enter the sterile field. However, this disadvantageously requires detachment and sterilization of the adaptors after each procedure and also causes a greater likelihood of contamination through the holes in the drape.

Furthermore, with current sterile drape designs for multi-arm surgical robotic systems, each individual arm of the system is draped, but such designs are not applicable for a single port system, in particular when all the instrument actuators are moved together by a single slave manipulator.

What is needed, therefore, are improved telerobotic systems, apparatus, and methods for remotely controlling surgical instruments at a surgical site on a patient. In particular, these systems, apparatus, and methods should be configured to minimize the need for sterilization to improve cost efficiency while also protecting the system and the surgical patient. In addition, these systems, apparatus, and methods should be designed to minimize instrument exchange time and difficulty during the surgical procedure while offering an accurate interface between the instrument and the manipulator. Furthermore, these systems and apparatus should be configured to minimize form factor so as to provide the most available space around the entry port for surgical staff while also providing for improved range of motion. Furthermore, these systems, apparatus, and methods should provide for organizing, supporting, and efficiently operating multiple instruments through a single port while reducing collisions between instruments and other apparatus.

SUMMARY

The present disclosure provides improved surgical systems, apparatus, and methods for telerobotic surgery. According to one aspect, a system, apparatus, and method provide at least one telemanipulated surgical instrument at a distal end of a draped instrument manipulator and manipulator arm with an accurate and robust interface while also providing for ease of instrument exchange and enhanced instrument manipulation, each surgical instrument working independently of the other and each having an end effector with at least six actively controlled degrees of freedom in Cartesian space (i.e., surge, heave, sway, roll, pitch, yaw).

In one embodiment, a robotic surgical system includes a base, and a setup link operably coupled to the base, the setup link locating a remote center of motion for the robotic surgical system. The system further includes a proximal link operably coupled to the setup link, a distal link operably coupled to the proximal link, and a plurality of instrument manipulators rotatably coupled to a distal end of the distal link, each of the instrument manipulators including a plurality of actuator outputs distally protruding from a distal end of a frame.

In another embodiment, a robotic surgical system includes the elements described above and a plurality of surgical instruments operably coupled to the distal end of a corresponding instrument manipulator, wherein each instrument has actuator inputs on a proximal face of a force transmission mechanism engaged with corresponding actuator outputs of the corresponding instrument manipulator.

In yet another embodiment, a method of coupling a surgical instrument to a manipulator arm of a robotic surgical system includes providing a robotic surgical system as described above and mounting a proximal face of a surgical instrument to the distal end of a corresponding instrument manipulator to operably couple the actuator outputs of the instrument manipulator and actuator inputs of the surgical instrument.

A more complete understanding of embodiments of the present disclosure will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 1A and 1B illustrate schematic views of a patient side support assembly in a telesurgical system with and without a sterile drape, respectively, in accordance with an embodiment of the present disclosure.

FIG. 3 is a perspective view that illustrates an embodiment of a manipulator base platform, cluster of instrument manipulators, and mounted instruments.

FIGS. 4A and 4B illustrate perspective views of an instrument manipulator extended and retracted, respectively, along an insertion axis.

FIGS. 5A-2 and 5B-2 illustrate sectional views of FIGS. 5A1 and 5B1, respectively.

FIGS. 5C-1 through 5C-4 illustrate different views of the instrument manipulator without an outer housing.

FIGS. 32A and 32B illustrate a bottom perspective view and a sectional view, respectively, of a distal portion of the counterbalancing link in accordance with an embodiment.

FIG. 33 illustrates a side view of the distal portion of the counterbalancing link without an end plug, FIG. 34 illustrates an enlarged perspective view of the end plug linear guide, and FIG. 35 illustrates a perspective view of an adjustment pin in accordance with various aspects of the present disclosure.

Figure 2A:
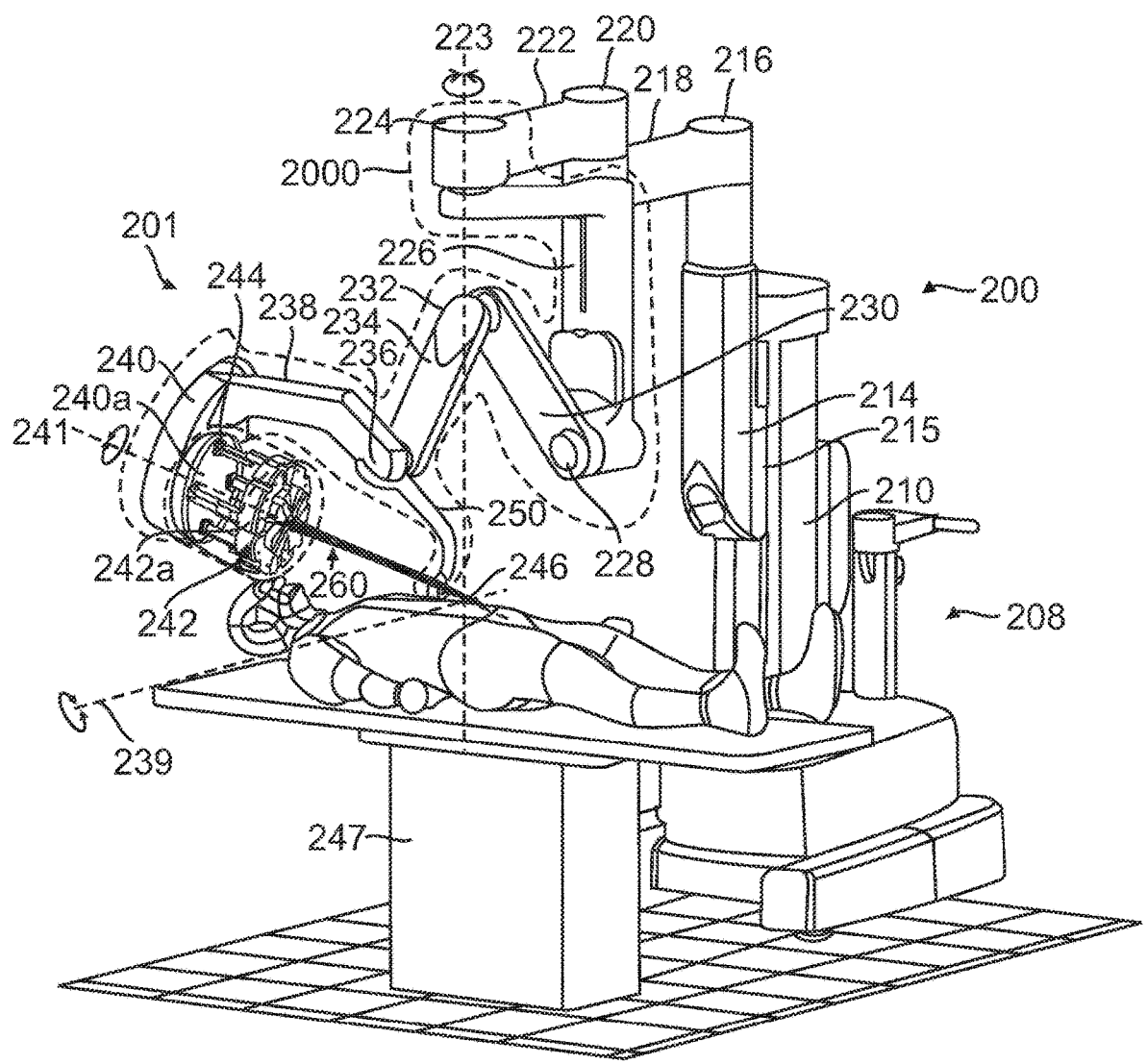
FIG. 2A is a diagrammatic perspective view that illustrates an embodiment of a telesurgical system with a sterile drape and mounted instruments.

Embodiments of the present disclosure and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

This description and the accompanying drawings that illustrate aspects and embodiments of the present disclosure should not be taken as limiting. Various mechanical, compositional, structural, electrical, and operational changes may be made without departing from the spirit and scope of this description. In some instances, well-known circuits, structures, and techniques have not been shown in detail in order not to obscure the disclosure. Like numbers in two or more figures represent the same or similar elements.

Further, this description's terminology is not intended to limit the disclosure. For example, spatially relative terms, such as "beneath", "below", "lower", "above", "upper" "proximal", "distal", and the like, may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

In one example, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

The use of an operator's inputs at a master device to control a robotic slave device and perform work at a work site is well known. Such systems are called various names, such as teleoperation, telemanipulation, or telerobotic systems. One type of telemanipulation system gives the operator a perception of being present at the work site, and such systems are called, for example, telepresence systems. The da Vinci® Surgical System, commercialized by Intuitive Surgical, Inc. of Sunnyvale, Calif., is an example of a telemanipulation system with telepresence. Telepresence fundamentals for such a surgical system are disclosed in U.S. Pat. No. 6,574,355 (filed Mar. 21, 2001), which is incorporated herein by reference. A teleoperated surgical system (with or without a telepresence feature) may be referred to as a telesurgical system.

To avoid repetition in the figures and the descriptions below of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. Accordingly, aspects described with reference to one depicted and/or described embodiment may be present with or applied to other depicted and/or described embodiments unless it is impractical to do so.

Accordingly, several general aspects apply to various descriptions below. Various surgical instruments, guide tubes, and instrument assemblies are applicable in the present disclosure and are further described in U.S. patent application Ser. No. 11/762,165 (filed Jun. 13, 2007; U.S. Patent Application Pub. No. US 2008/0065105 A1), which is incorporated herein by reference. Surgical instruments alone, or assemblies including guide tubes, multiple instruments, and/or multiple guide tubes, are applicable in the present disclosure. Therefore, various surgical instruments may be utilized, each surgical instrument working independently of the other, and each having an end effector. In some instances the end effectors operate with at least six actively controlled DOFs in Cartesian space (i.e., surge, heave, sway, roll, pitch, yaw), via a single entry port in a patient. One or more additional end effector DOFs may apply to, e.g., end effector jaw movement in gripping or shearing instruments.

For example, at least one surgical end effector is shown or described in various figures. An end effector is the part of the minimally invasive surgical instrument or assembly that performs a specific surgical function (e.g., forceps/graspers, needle drivers, scissors, electrocautery hooks, staplers, clip appliers/removers, etc.). Many end effectors themselves have a single DOF (e.g., graspers that open and close). The end effector may be coupled to the surgical instrument body with a mechanism that provides one or more additional DOFs, such as "wrist" type mechanisms. Examples of such mechanisms are shown in U.S. Pat. No. 6,371,952 (filed Jun. 28, 1999; Madhani et al.) and in U.S. Pat. No. 6,817,974 (filed Jun. 28, 2002; Cooper et al.), both of which are incorporated by reference herein, and may be known as various Intuitive Surgical, Inc. Endowrist.RTM. mechanisms as used on both 8 mm and 5 mm instruments for da Vinci.RTM. Surgical Systems. Although the surgical instruments described herein generally include end effectors, it should be understood that in some aspects an end effector may be omitted. For example, the blunt distal tip of an instrument body shaft may be used to retract tissue. As another example, suction or irrigation openings may exist at the distal tip of a body shaft or the wrist mechanism. In these aspects, it should be understood that descriptions of positioning and orienting an end effector include positioning and orienting the tip of a surgical instrument that does not have an end effector. For example, a description that addresses the reference frame for a tip of an end effector should also be read to include the reference frame of a tip of a surgical instrument that does not have an end effector.

Throughout this description, it should be understood that a mono or stereoscopic imaging system/image capture component/camera device may be placed at the distal end of an instrument wherever an end effector is shown or described (the device may be considered a "camera instrument"), or it may be placed near or at the distal end of any guide tube or other instrument assembly element. Accordingly, the terms "imaging system" and the like as used herein should be broadly construed to include both image capture components and combinations of image capture components with associated circuitry and hardware, within the context of the aspects and embodiments being described. Such endoscopic imaging systems (e.g., optical, infrared, ultrasound, etc.) include systems with distally positioned image sensing chips and associated circuits that relay captured image data via a wired or wireless connection to outside the body. Such endoscopic imaging systems also include systems that relay images for capture outside the body (e.g., by using rod lenses or fiber optics). In some instruments or instrument assemblies a direct view optical system (the endoscopic image is viewed directly at an eyepiece) may be used. An example of a distally positioned semiconductor stereoscopic imaging system is described in U.S. patent application Ser. No. 11/614,661 (filed Dec. 21, 2006; disclosing "Stereoscopic Endoscope"; Shafer et al.), which is incorporated by reference. Well-known endoscopic imaging system components, such as electrical and fiber optic illumination connections, are omitted or symbolically represented for clarity. Illumination for endoscopic imaging is typically represented in the drawings by a single illumination port. It should be understood that these depictions are exemplary. The sizes, positions, and numbers of illumination ports may vary. Illumination ports are typically arranged on multiple sides of the imaging apertures, or completely surrounding the imaging apertures, to minimize deep shadows.

In this description, cannulas are typically used to prevent a surgical instrument or guide tube from rubbing on patient tissue. Cannulas may be used for both incisions and natural orifices. For situations in which an instrument or guide tube does not frequently translate or rotate relative to its insertion (longitudinal) axis, a cannula may not be used. For situations that require insufflation, the cannula may include a seal to prevent excess insufflation gas leakage past the instrument or guide tube. Examples of cannula assemblies which support insufflation and procedures requiring insufflation gas at the surgical site may be found in U.S. patent application Ser. No. 12/705,439 (filed Feb. 12, 2010; disclosing "Entry Guide for Multiple Instruments in a Single Port System"), the full disclosure of which is incorporated by reference herein for all purposes. For thoracic surgery that does not require insufflation, the cannula seal may be omitted, and if instruments or guide tube insertion axis movement is minimal, then the cannula itself may be omitted. A rigid guide tube may function as a cannula in some configurations for instruments that are inserted relative to the guide tube. Cannulas and guide tubes may be, e.g., steel or extruded plastic. Plastic, which is less expensive than steel, may be suitable for one-time use.

Various instances and assemblies of flexible surgical instruments and guide tubes are shown and described in U.S. patent application Ser. No. 11/762,165, cited above. Such flexibility, in this description, is achieved in various ways. For example, a segment of an instrument or guide tube may be a continuously curving flexible structure, such as one based on a helical wound coil or on tubes with various segments removed (e.g., kerf-type cuts). Or, the flexible part may be made of a series of short, pivotally connected segments ("vertebrae") that provide a snake-like approximation of a continuously curving structure. Instrument and guide tube structures may include those in U.S. Patent Application Pub. No. US 2004/0138700 (filed Dec. 2, 2003; Cooper et al.), which is incorporated by reference herein. For clarity, the figures and associated descriptions generally show only two segments of instruments and guide tubes, termed proximal (closer to the transmission mechanism; farther from the surgical site) and distal (farther from the transmission mechanism; closer to the surgical site). It should be understood that the instruments and guide tubes may be divided into three or more segments, each segment being rigid, passively flexible, or actively flexible. Flexing and bending as described for a distal segment, a proximal segment, or an entire mechanism also apply to intermediate segments that have been omitted for clarity. For instance, an intermediate segment between proximal and distal segments may bend in a simple or compound curve. Flexible segments may be various lengths. Segments with a smaller outside diameter may have a smaller minimum radius of curvature while bending than segments with a larger outside diameter. For cable-controlled systems, unacceptably high cable friction or binding limits minimum radius of curvature and the total bend angle while bending. The guide tube's (or any joint's) minimum bend radius is such that it does not kink or otherwise inhibit the smooth motion of the inner surgical instrument's mechanism. Flexible components may be, for example, up to approximately four feet in length and approximately 0.6 inches in diameter. Other lengths and diameters (e.g., shorter, smaller) and the degree of flexibility for a specific mechanism may be determined by the target anatomy for which the mechanism has been designed.

In some instances only a distal segment of an instrument or guide tube is flexible, and the proximal segment is rigid. In other instances, the entire segment of the instrument or guide tube that is inside the patient is flexible. In still other instances, an extreme distal segment may be rigid, and one or more other proximal segments are flexible. The flexible segments may be passive or they may be actively controllable ("steerable"). Such active control may be done using, for example, sets of opposing cables (e.g., one set controlling "pitch" and an orthogonal set controlling "yaw"; three cables can be used to perform similar action). Other control elements such as small electric or magnetic actuators, shape memory alloys, electroactive polymers ("artificial muscle"), pneumatic or hydraulic bellows or pistons, and the like may be used. In instances in which a segment of an instrument or guide tube is fully or partially inside another guide tube, various combinations of passive and active flexibility may exist. For instance, an actively flexible instrument inside a passively flexible guide tube may exert sufficient lateral force to flex the surrounding guide tube. Similarly, an actively flexible guide tube may flex a passively flexible instrument inside it. Actively flexible segments of guide tubes and instruments may work in concert. For both flexible and rigid instruments and guide tubes, control cables placed farther from the center longitudinal axis may provide a mechanical advantage over cables placed nearer to the center longitudinal axis, depending on compliance considerations in the various designs.

The flexible segment's compliance (stiffness) may vary from being almost completely flaccid (small internal frictions exist) to being substantially rigid. In some aspects, the compliance is controllable. For example, a segment or all of a flexible segment of an instrument or guide tube can be made substantially (i.e., effectively but not infinitely) rigid (the segment is "rigidizable" or "lockable"). The lockable segment may be locked in a straight, simple curve or in a compound curve shape. Locking may be accomplished by applying tension to one or more cables that run longitudinally along the instrument or guide tube that is sufficient to cause friction to prevent adjacent vertebrae from moving. The cable or cables may run through a large, central hole in each vertebra or may run through smaller holes near the vertebra's outer circumference. Alternatively, the drive element of one or more motors that move one or more control cables may be soft-locked in position (e.g., by servocontrol) to hold the cables in position and thereby prevent instrument or guide tube movement, thus locking the vertebrae in place. Keeping a motor drive element in place may be done to effectively keep other movable instrument and guide tube components in place as well. It should be understood that the stiffness under servocontrol, although effective, is generally less than the stiffness that may be obtained with braking placed directly on joints, such as the braking used to keep passive setup joints in place. Cable stiffness generally dominates because it is generally less than servosystem or braked joint stiffness.

In some situations, the compliance of the flexible segment may be continuously varied between flaccid and rigid states. For example, locking cable tension can be increased to increase stiffness but without locking the flexible segment in a rigid state. Such intermediate compliance may allow for telesurgical operation while reducing tissue trauma that may occur due to movements caused by reactive forces from the surgical site. Suitable bend sensors incorporated into the flexible segment allow the telesurgical system to determine instrument and/or guide tube position as it bends. U.S. Patent Application Pub. No. US 2006/0013523 (filed Jul. 13, 2005; Childers et al.), which is incorporated by reference herein, discloses a fiber optic position shape sensing device and method. U.S. patent application Ser. No. 11/491,384 (filed Jul. 20, 2006; Larkin et al.), which is incorporated by reference herein, discloses fiber optic bend sensors (e.g., fiber Bragg gratings) used in the control of such segments and flexible devices.

A surgeon's inputs to control aspects of the minimally invasive surgical instrument assemblies, instruments, end effectors, and manipulator arm configuration as described herein are generally done using an intuitive, camera-referenced control interface. For example, the da Vinci® Surgical System includes a surgeon's console with such a control interface, which may be modified to control aspects described herein. The surgeon manipulates one or more master manual input mechanisms having, e.g., 6 DOFs to control the slave instrument assembly and instrument. The input mechanisms include a finger-operated grasper to control one or more end effector DOFs (e.g., closing grasping jaws). Intuitive control is provided by orienting the relative positions of the end effectors and the endoscopic imaging system with the positions of the surgeon's input mechanisms and image output display. This orientation allows the surgeon to manipulate the input mechanisms and end effector controls as if viewing the surgical work site in substantially true presence. This teleoperation true presence means that the surgeon views an image from a perspective that appears to be that of an operator directly viewing and working at the surgical site. U.S. Pat. No. 6,671,581 (filed Jun. 5, 2002; Niemeyer et al.), which is incorporated by reference, contains further information on camera referenced control in a minimally invasive surgical apparatus.

Single Port Surgical System

Referring now to FIGS. 1A and 1B, schematic side and front views are shown that illustrate aspects of a robot-assisted (telemanipulative) minimally invasive surgical system that uses aspects of the minimally invasive surgical instruments, instrument assemblies, and manipulation and control systems described herein. The three main components are an endoscopic imaging system 102, a surgeon's console 104 (master), and a patient side support system 100 (slave), all interconnected by wired (electrical or optical) or wireless connections 106 as shown. One or more electronic data processors may be variously located in these main components to provide system functionality. Examples are disclosed in U.S. patent application Ser. No. 11/762,165, cited above. A sterile drape 1000, shown in dotted line, advantageously drapes at least a portion of the patient side support system 100 to maintain a sterile field during a surgical procedure while also providing for efficient and simple instrument exchange in conjunction with an accurate interface between the instrument and its associated manipulator.

Imaging system 102 performs image processing functions on, e.g., captured endoscopic imaging data of the surgical site and/or preoperative or real time image data from other imaging systems external to the patient. Imaging system 102 outputs processed image data (e.g., images of the surgical site, as well as relevant control and patient information) to the surgeon at the surgeon's console 104. In some aspects the processed image data is output to an optional external monitor visible to other operating room personnel or to one or more locations remote from the operating room (e.g., a surgeon at another location may monitor the video; live feed video may be used for training; etc.).

The surgeon's console 104 includes, e.g., multiple DOF mechanical input ("master") devices that allow the surgeon to manipulate the surgical instruments, guide tubes, and imaging system ("slave") devices as described herein. These input devices may in some aspects provide haptic feedback from the instruments and instrument assembly components to the surgeon. Console 104 also includes a stereoscopic video output display positioned such that images on the display are generally focused at a distance that corresponds to the surgeon's hands working behind/below the display screen. These aspects are discussed more fully in U.S. Pat. No. 6,671,581 which is incorporated by reference herein.

Control during insertion may be accomplished, for example, by the surgeon virtually moving the image with one or both of the masters; she uses the masters to move the image side to side and to pull it towards herself, consequently commanding the imaging system and its associated instrument assembly (e.g., a flexible guide tube) to steer towards a fixed center point on the output display and to advance inside the patient. In one aspect the camera control is designed to give the impression that the masters are fixed to the image so that the image moves in the same direction that the master handles are moved. This design causes the masters to be in the correct location to control the instruments when the surgeon exits from camera control, and consequently it avoids the need to clutch (disengage), move, and declutch (engage) the masters back into position prior to beginning or resuming instrument control. In some aspects the master position may be made proportional to the insertion velocity to avoid using a large master workspace. Alternatively, the surgeon may clutch and declutch the masters to use a ratcheting action for insertion. In some aspects, insertion may be controlled manually (e.g., by hand operated wheels), and automated insertion (e.g., servomotor driven rollers) is then done when the distal end of the surgical instrument assembly is near the surgical site. Preoperative or real time image data (e.g., MRI, X-ray) of the patient's anatomical structures and spaces available for insertion trajectories may be used to assist insertion.

The patient side support system 100 includes a floor-mounted base 108, or alternately a ceiling mounted base 110 as shown by the alternate lines. The base may be movable or fixed (e.g., to the floor, ceiling, wall, or other equipment such as an operating table).

Base 108 supports an arm assembly 101 that includes a passive, uncontrolled "setup" portion and an actively controlled "manipulator" portion. In one example, the setup portion includes two passive rotational "setup" joints 116 and 120, which allow manual positioning of the coupled setup links 118 and 122 when the joint brakes are released. A passive prismatic setup joint (not shown) between the arm assembly and the base coupled to a link 114 may be used to allow for large vertical adjustments 112. Alternatively, some of these setup joints may be actively controlled, and more or fewer setup joints may be used in various configurations. The setup joints and links allow a person to place the robotic manipulator portion of the arm at various positions and orientations in Cartesian x, y, z space. The remote center of motion is the location at which yaw, pitch, and roll axes intersect (i.e., the location at which the kinematic chain remains effectively stationary while joints move through their range of motion). As described in more detail below, some of these actively controlled joints are robotic manipulators that are associated with controlling DOFs of individual surgical instruments, and others of these actively controlled joints are associated with controlling DOFs of a single assembly of these robotic manipulators. The active joints and links are movable by motors or other actuators and receive movement control signals that are associated with master arm movements at surgeon's console 104.

As shown in FIGS. 1A and 1B, a manipulator assembly yaw joint 124 is coupled between a distal end of setup link 122 and a proximal end of a first manipulator link 126. Yaw joint 124 allows link 126 to move with reference to link 122 in a motion that may be arbitrarily defined as "yaw" around a manipulator assembly yaw axis 123. As shown, the rotational axis of yaw joint 124 is aligned with a remote center of motion 146, which is generally the position at which an instrument (not shown) enters the patient (e.g., at the umbilicus for abdominal surgery). In one embodiment, setup link 122 is rotatable along a horizontal or x, y plane and yaw joint 124 is configured to allow first manipulator link 126 to rotate about yaw axis 123, such that the setup link 122, yaw joint 124, and first manipulator link 126 provide a constantly vertical yaw axis 123 for the robot arm assembly, as illustrated by the vertical dashed line from yaw joint 124 to remote center of motion 146.

A distal end of first manipulator link 126 is coupled to a proximal end of a second manipulator link 130, a distal end of second manipulator link 130 is coupled to a proximal end of a third manipulator link 134, and a distal end of third manipulator link 134 is coupled to a proximal end of a fourth manipulator link 138, by actively controlled rotational joints 128, 132, and 136, respectively. In one embodiment, links 130, 134, and 138 are coupled together to act as a coupled motion mechanism. Coupled motion mechanisms are well known (e.g., such mechanisms are known as parallel motion linkages when input and output link motions are kept parallel to each other). For example, if rotational joint 128 is actively rotated, then joints 132 and 136 also rotate so that link 138 moves with a constant relationship to link 130.

Therefore, it can be seen that the rotational axes of joints 128, 132, and 136 are parallel. When these axes are perpendicular to joint 124's rotational axis, links 130, 134, and 138 move with reference to link 126 in a motion that may be arbitrarily defined as "pitch" around a manipulator assembly pitch axis 139. Since links 130, 134, and 138 move as a single assembly in one embodiment, first manipulator link 126 may be considered an active proximal manipulator link, and second through fourth manipulator links 130, 134, and 138 may be considered collectively an active distal manipulator link.

A manipulator assembly platform 140 is coupled to a distal end of fourth manipulator link 138. Manipulator platform 140 includes a rotatable base plate that supports manipulator assembly 142, which includes two or more surgical instrument manipulators that are described in more detail below. The rotating base plate allows manipulator assembly 142 to rotate as a single unit with reference to platform 140 in a motion that may be arbitrarily defined as "roll" around a manipulator assembly roll axis 141.

For minimally invasive surgery, the instruments must remain substantially stationary with respect to the location at which they enter the patient's body, either at an incision or at a natural orifice, to avoid unnecessary tissue damage. Accordingly, the yaw and pitch motions of the instrument shaft should be centered at a single location on the manipulator assembly roll axis or instrument insertion axis that stays relatively stationary in space. This location is referred to as a remote center of motion. For single port minimally invasive surgery, in which all instruments (including a camera instrument) must enter via a single small incision (e.g., at the umbilicus) or natural orifice, all instruments must move with reference to such a generally stationary remote center of motion. Therefore, a remote center of motion for manipulator assembly 142 is defined by the intersection of manipulator assembly yaw axis 123 and manipulator assembly pitch axis 139. The configuration of links 130, 134, and 138, and of joints 128, 132, and 136 is such that remote center of motion 146 is located distal of manipulator assembly 142 with sufficient distance to allow the manipulator assembly to move freely with respect to the patient. It can be seen that manipulator assembly roll axis 141 also intersects remote center of motion 146.

As described in more detail below, a surgical instrument is mounted on and actuated by each surgical instrument manipulator of manipulator assembly 142. The instruments are removably mounted so that various instruments may be interchangeably mounted on a particular instrument manipulator. In one aspect, one or more instrument manipulators may be configured to support and actuate a particular type of instrument, such as a camera instrument. The shafts of the instruments extend distally from the instrument manipulators. The shafts extend through a common cannula placed at the entry port into the patient (e.g., through the body wall or at a natural orifice). In one aspect, an entry guide is positioned within the cannula, and each instrument shaft extends through a channel in the entry guide, so as to provide additional support for the instrument shafts. The cannula is removably coupled to a cannula mount 150, which in one embodiment is coupled to the proximal end of fourth manipulator link 138. In one implementation, the cannula mount 150 is coupled to link 138 by a rotational joint that allows the mount to move between a stowed position adjacent link 138 and an operational position that holds the cannula in the correct position so that the remote center of motion 146 is located along the cannula. During operation, the cannula mount is fixed in position relative to link 138 according to one aspect. The instrument(s) may slide through an entry guide and cannula assembly mounted to a distal end of the cannula mount 150, examples of which are explained in further detail below. The various passive setup joints/links and active joints/links allow positioning of the instrument manipulators to move the instruments and imaging system with a large range of motion when a patient is placed in various positions on a movable table. In some embodiments, a cannula mount may be coupled to the proximal link or first manipulator link 126.

Certain setup and active joints and links in the manipulator arm may be omitted to reduce the robot's size and shape, or joints and links may be added to increase degrees of freedom. It should be understood that the manipulator arm may include various combinations of links, passive joints, and active joints (redundant DOFs may be provided) to achieve a necessary range of poses for surgery. Furthermore, various surgical instruments alone or instrument assemblies including guide tubes, multiple instruments, and/or multiple guide tubes, and instruments coupled to instrument manipulators (e.g., actuator assemblies) via various configurations (e.g., on a proximal face or a distal face of the instrument transmission means or the instrument manipulator), are applicable in aspects of the present disclosure.

Figure 2B:
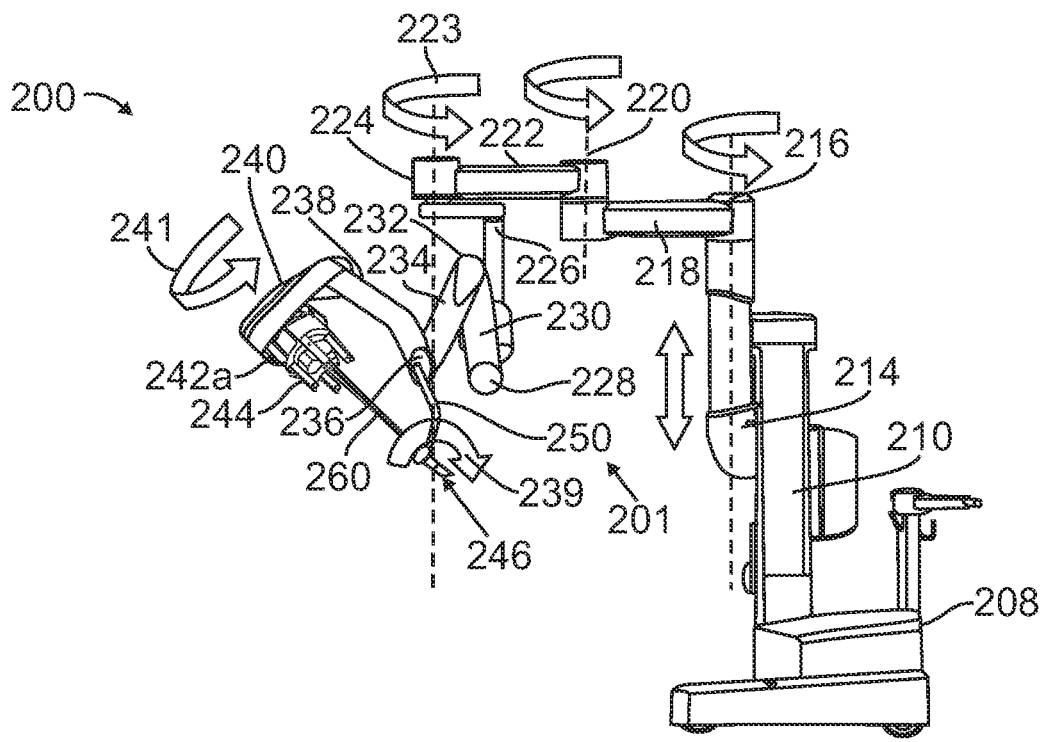
FIGS. 2B and 2C illustrate side and top views, respectively, of the telesurgical system of FIG. 2A without a sterile drape being shown.
Figure 2C:
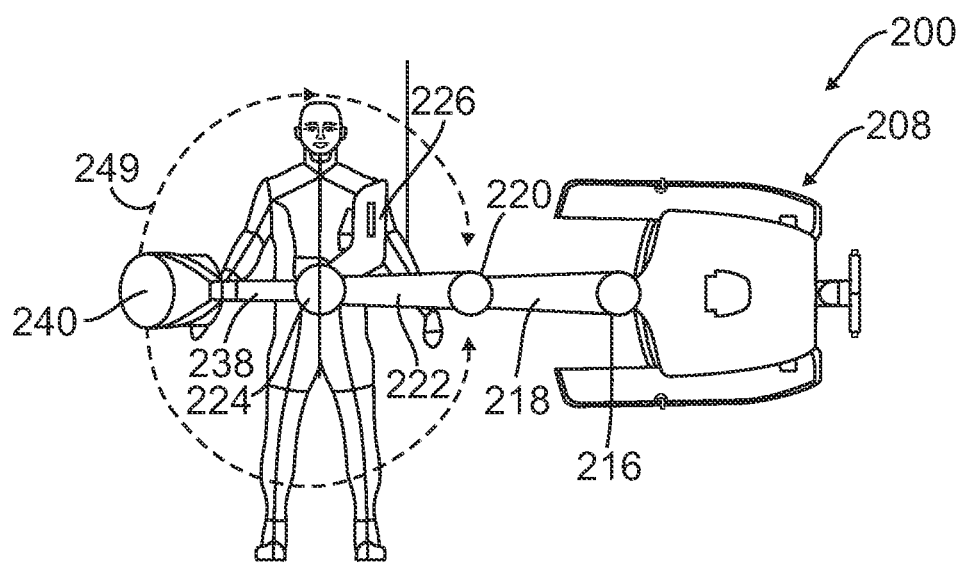

FIGS. 2A-2C are diagrammatic perspective, side, and top views, respectively, of a patient side support cart 200 in a teleoperated surgical (telesurgical) system. The depicted cart 200 is an illustrative embodiment of the general configuration described above with reference to FIGS. 1A and 1B. A surgeon's console and a video system are not shown but are applicable as described above with respect to FIGS. 1A and 1B and known telerobotic surgical system architectures (e.g., the da Vinci® Surgical System architecture). In this embodiment, cart 200 includes a floor-mounted base 208. The base may be movable or fixed (e.g., to the floor, ceiling, wall, or other sufficiently rigid structure). Base 208 supports support column 210, and an arm assembly 201 is coupled to support column 210. The arm assembly includes two passive rotational setup joints 216 and 220, which when their brakes are released allow manual positioning of the coupled setup links 218 and 222. In the depicted embodiment, setup links 218 and 222 move in a horizontal plane (parallel to the floor). The arm assembly is coupled to support column 210 at a passive sliding setup joint 215 between the column 210 and a vertical setup link 214. Joint 215 allows the manipulator arm to be vertically (perpendicular to the floor) adjusted. Accordingly, the passive setup joints and links may be used to properly position a remote center of motion 246 with reference to the patient. Once the remote center of motion 246 is properly positioned, brakes at each of the joints 215, 216, and 220 are set to prevent the setup portion of the arm from moving.

In addition, the arm assembly includes active joints and links for manipulator arm configuration and movement, instrument manipulation, and instrument insertion. The proximal end of a first manipulator link 226 is coupled to the distal end of setup link 222 via an actively controlled rotational manipulator assembly yaw joint 224. As shown, the rotational manipulator assembly yaw axis 223 of yaw joint 224 is aligned with remote center of motion 246, as illustrated by the vertical dashed line from yaw joint 224 to remote center of motion 246.

The distal end of first manipulator link 226 is coupled to the proximal end of a second manipulator link 230, the distal end of second manipulator link 230 is coupled to the proximal end of a third manipulator link 234, and the distal end of third manipulator link 234 is coupled to the proximal end of a fourth manipulator link 238, by actively controlled rotational joints 228, 232, and 236, respectively. As described above, links 230, 234, and 238 function as a coupled motion mechanism, so that fourth manipulator link 238 automatically moves in concert with second manipulator link 230 when link 230 is actuated. In the depicted embodiment, a mechanism similar to that disclosed in U.S. Pat. No. 7,594,912 (filed Sep. 30, 2004) is modified for use (see also e.g., U.S. patent application Ser. No. 11/611,849 (filed Dec. 15, 2006; U.S. Patent Application Pub. No. US 2007/0089557 A1)). Thus, first manipulator link 226 may be considered an active proximal link, and second through fourth links 230, 234, and 238 may be considered collectively an active distal link. In one embodiment, first link 226 may include a compression spring counterbalance mechanism, as further described below, to counterbalance forces from movement of the distal link about joint 228.

A manipulator assembly platform 240 is coupled to a distal end of fourth link 238. Platform 240 includes a base plate 240a upon which instrument manipulator assembly 242 is mounted. As shown in FIG. 2A, platform 240 includes a "halo" ring inside which a disk-shaped base plate 240a rotates. Configurations other than the halo and disk may be used in other embodiments. Base plate 240a's center of rotation is coincident with a manipulator assembly roll axis 241, as shown by the dashed line that extends through the center of manipulator platform 240 and remote center of motion 246. Instruments 260 are mounted to the instrument manipulators of manipulator assembly 242 on a distal face of the instrument manipulators in one embodiment.

As shown in FIGS. 2A and 2B, instrument manipulator assembly 242 includes four instrument manipulators 242a. Each instrument manipulator supports and actuates its associated instrument. In the depicted embodiment, one instrument manipulator 242a is configured to actuate a camera instrument, and three instrument manipulators 242a are configured to actuate various other interchangeable surgical instruments that perform surgical and/or diagnostic work at the surgical site. More or fewer instrument manipulators may be used. In some operational configurations, one or more manipulators may not have an associated surgical instrument during some or all of a surgical procedure. The instrument manipulators are disclosed in more detail below.

As mentioned above, a surgical instrument 260 is mounted to and actuated by a respective instrument manipulator 242a. In accordance with an aspect of the disclosure, each instrument is mounted to its associated manipulator at only the instrument's proximal end. It can be seen in FIG. 2A that this proximal end mounting feature keeps the instrument manipulator assembly 242 and support platform 240 as far from the patient as possible, which for the given instrument geometries allows the actively controlled portion of the manipulator arm to move freely within a maximum range of motion with reference to the patient while not colliding with the patient. The instruments 260 are mounted so that their shafts are clustered around manipulator assembly roll axis 241. Each shaft extends distally from the instrument's force transmission mechanism, and all shafts extend through a single cannula placed at the port into the patient. The cannula is removably held in a fixed position with reference to base plate 240a by a cannula mount 250, which is coupled to fourth manipulator link 238. A single guide tube is inserted into and freely rotates within the cannula, and each instrument shaft extends through an associated channel in the guide tube. The longitudinal axes of the cannula and guide tube are generally coincident with the roll axis 241. Therefore, the guide tube rotates within the cannula as base plate 240a rotates. In some embodiments, a cannula mount may be operably coupled to first manipulator link 226.

Each instrument manipulator 242a is movably coupled to an active telescoping insertion mechanism 244 (FIG. 2B) operably coupled to the base plate 240a and may be used to insert and withdraw the surgical instrument(s). FIG. 2A illustrates instrument manipulators 242a extended a distance toward a distal end of telescoping insertion mechanism 244 (see also FIGS. 3 and 4A), and FIG. 2B illustrates instrument manipulators 242 retracted to a proximal end of telescoping insertion mechanism 244 (see also FIG. 4B). Active joints 224, 228, 232, 236 and manipulator platform 240 move in conjunction and/or independently so that a surgical instrument (or assembly) moves around the remote center of motion 246 at an entry port, such as a patient's umbilicus, after the remote center of motion has been established by the passive setup arms and joints.

As shown in FIG. 2A, cannula mount 250 is coupled to fourth link 238 near the fourth manipulator link's proximal end. In other aspects, cannula mount 250 may be coupled to another section of the proximal link. As described above, cannula mount 250 is hinged, so that it can swing into a stowed position adjacent fourth link 238 and into an extended position (as shown) to support the cannula. During operation, cannula mount 250 is held in a fixed position relative to fourth link 238 according to one aspect.

It can be seen that in the depicted embodiment first manipulator link 226 is generally shaped as an inverted "L" in one example. A proximal leg of the "L" shaped link is coupled to link 226 at yaw joint 224, and a distal leg of the link is coupled to second manipulator link 238 at rotational joint 228. In this illustrative embodiment, the two legs are generally perpendicular, and the proximal leg of the first manipulator link rotates around a plane generally perpendicular to manipulator assembly yaw axis 223 (e.g., a horizontal (x, y) plane if the yaw axis is vertical (z)). Accordingly, the distal leg extends generally parallel to the manipulator assembly yaw axis 223 (e.g., vertically (z) if the yaw axis is vertical). This shape allows manipulator links 230, 234, and 238 to move underneath yaw joint 224, so that links 230, 234, and 238 provide a manipulator assembly pitch axis 239 that intersects remote center of motion 246. Other configurations of first link 226 are possible. For example, the proximal and distal legs of the first link 226 may not be perpendicular to each other, the proximal leg may rotate in a plane different from a horizontal plane, or link 226 may have other than a general "L" shape, such as an arc shape.

Figure 25A:
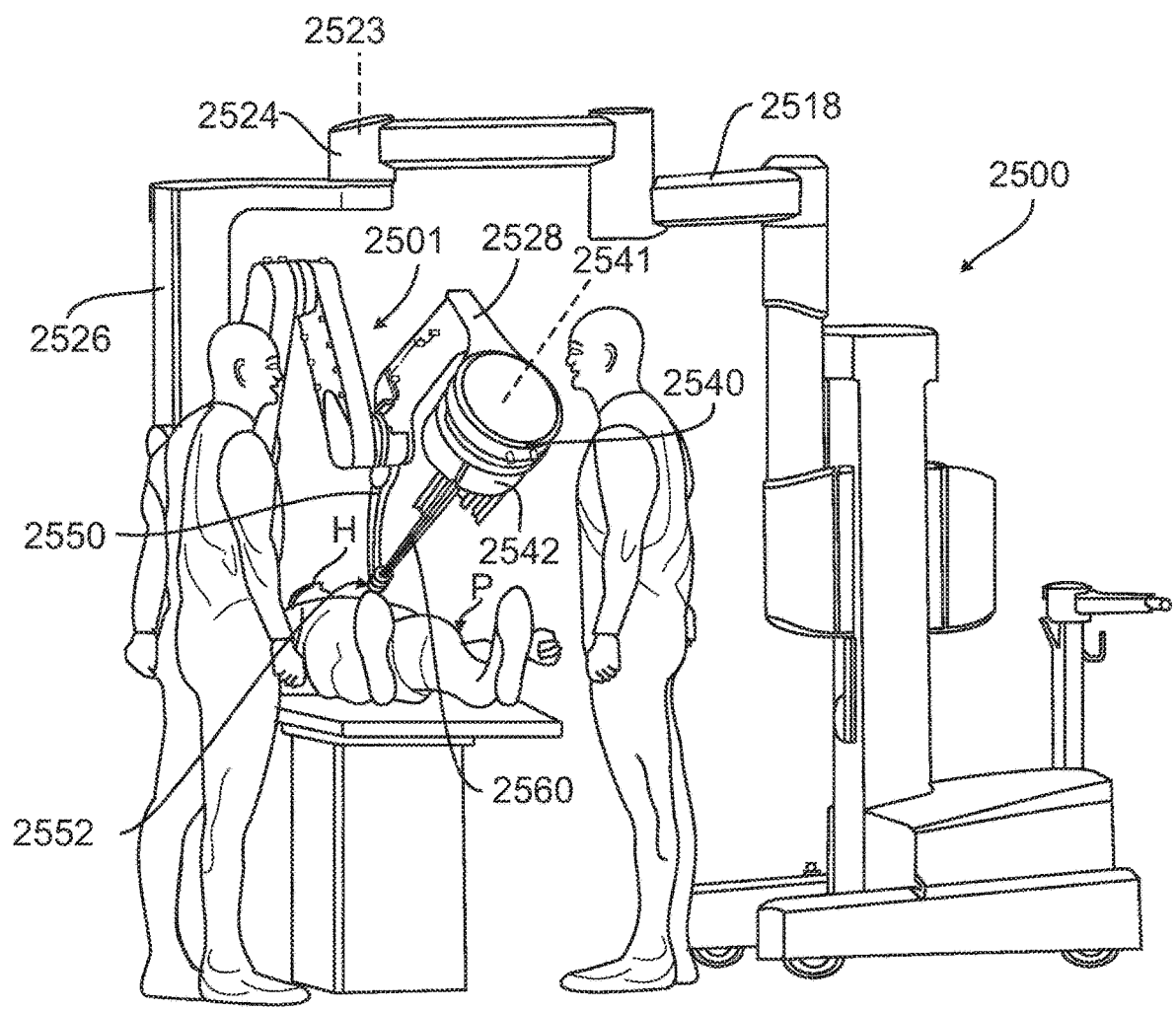
FIGS. 25A-25C, 26A-26C, and 27A-27C illustrate different views of a surgical system with an instrument manipulator assembly roll axis or instrument insertion axis pointed in different directions.
Figure 25B:
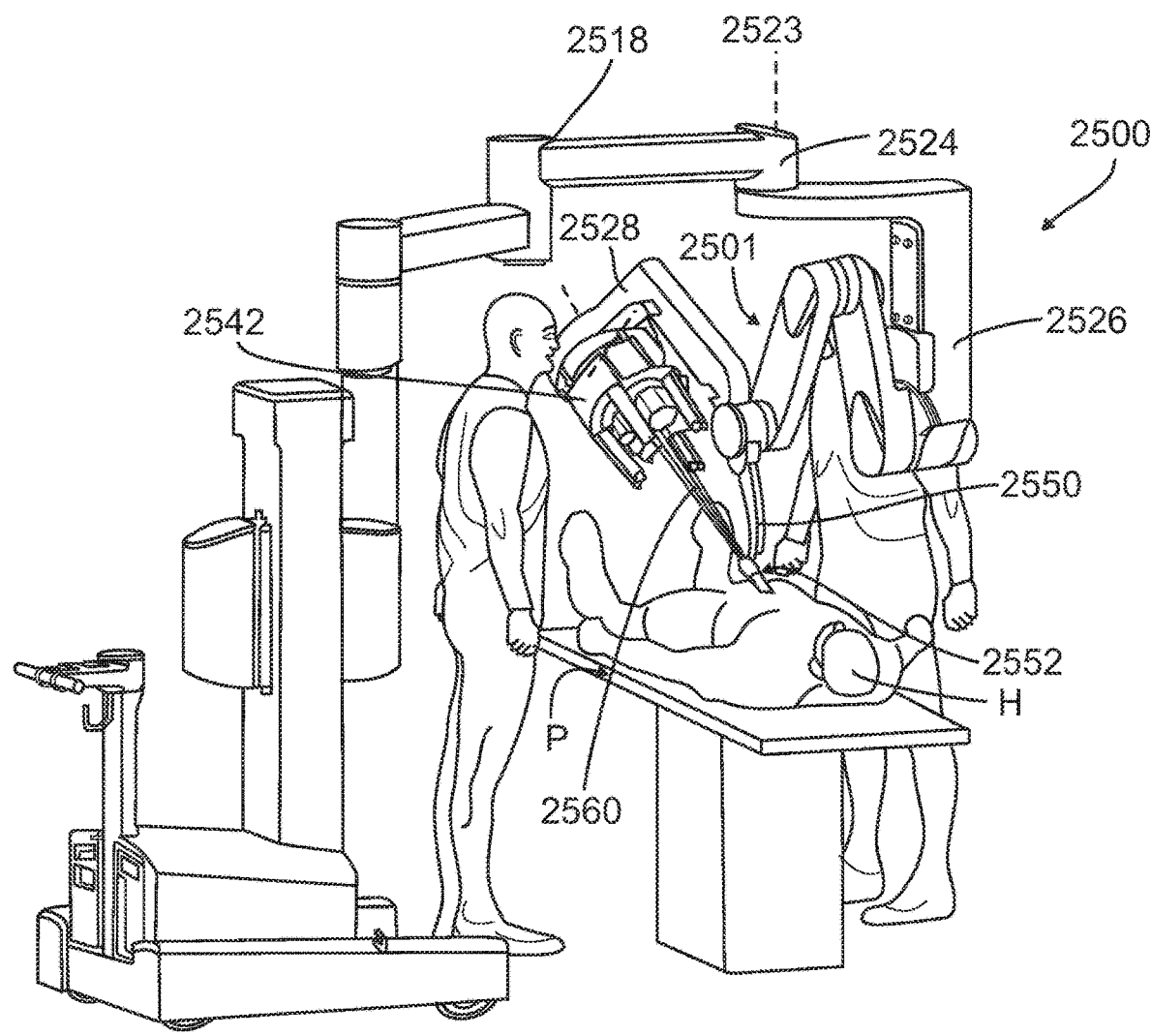
Figure 25C:
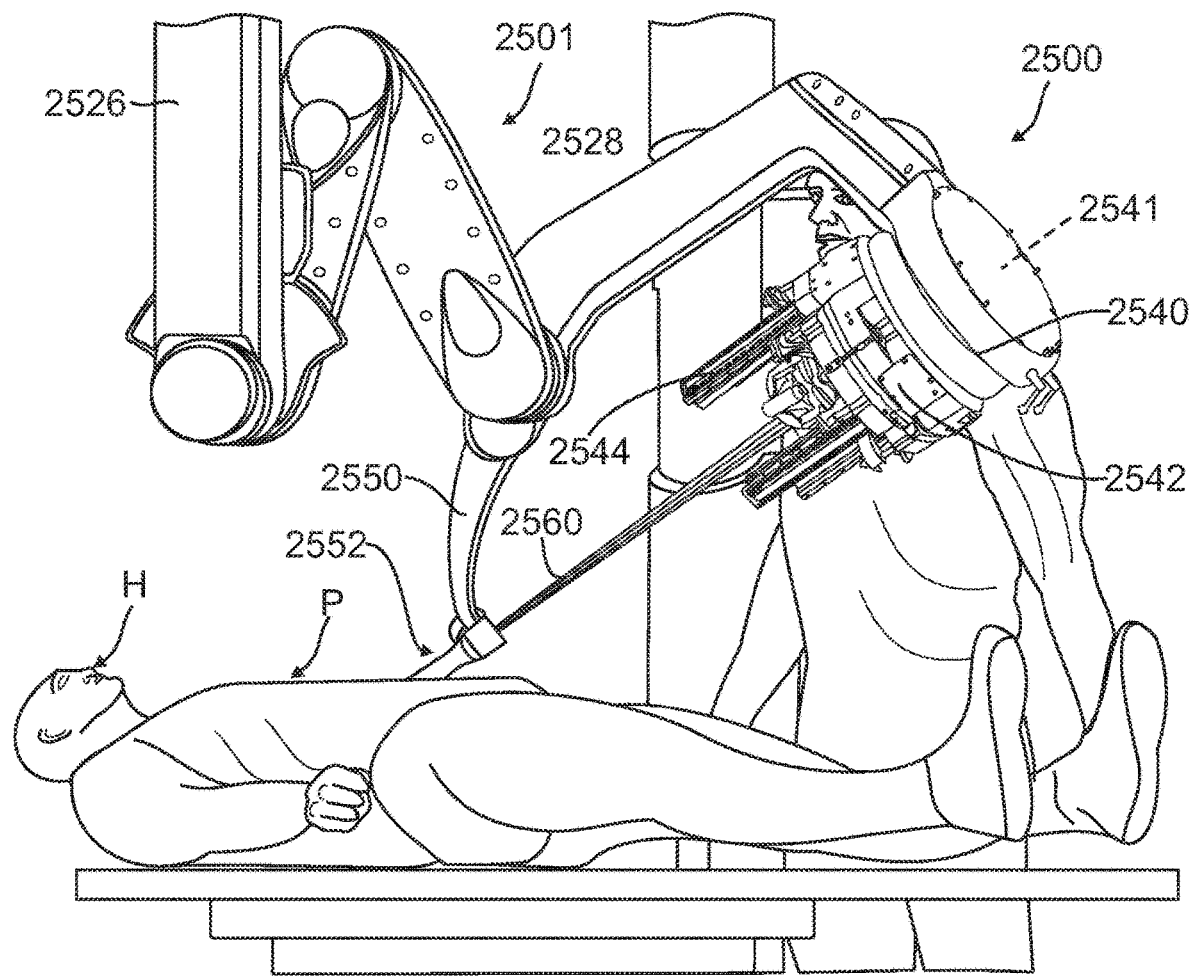
Figure 26A:
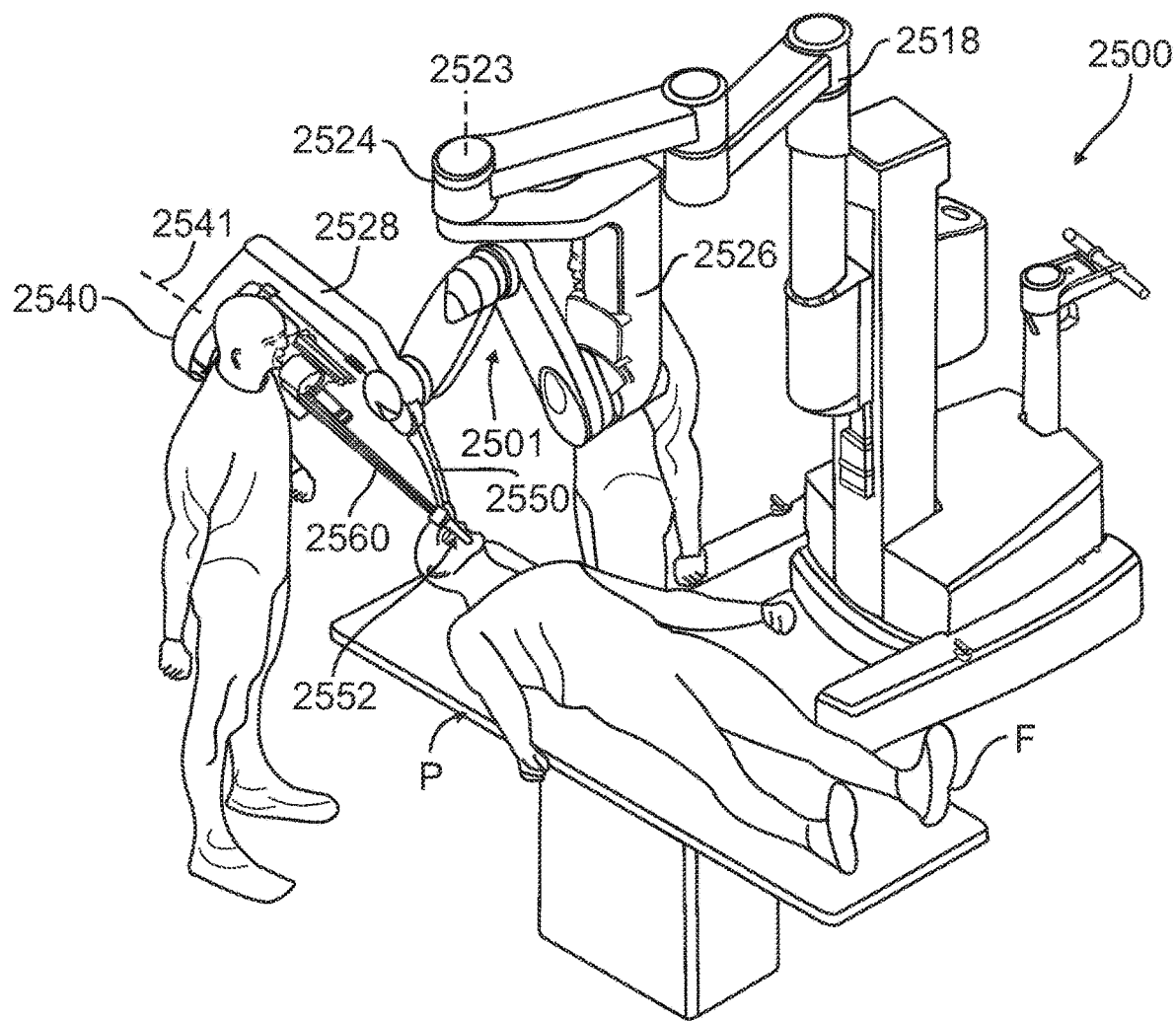
Figure 26B:
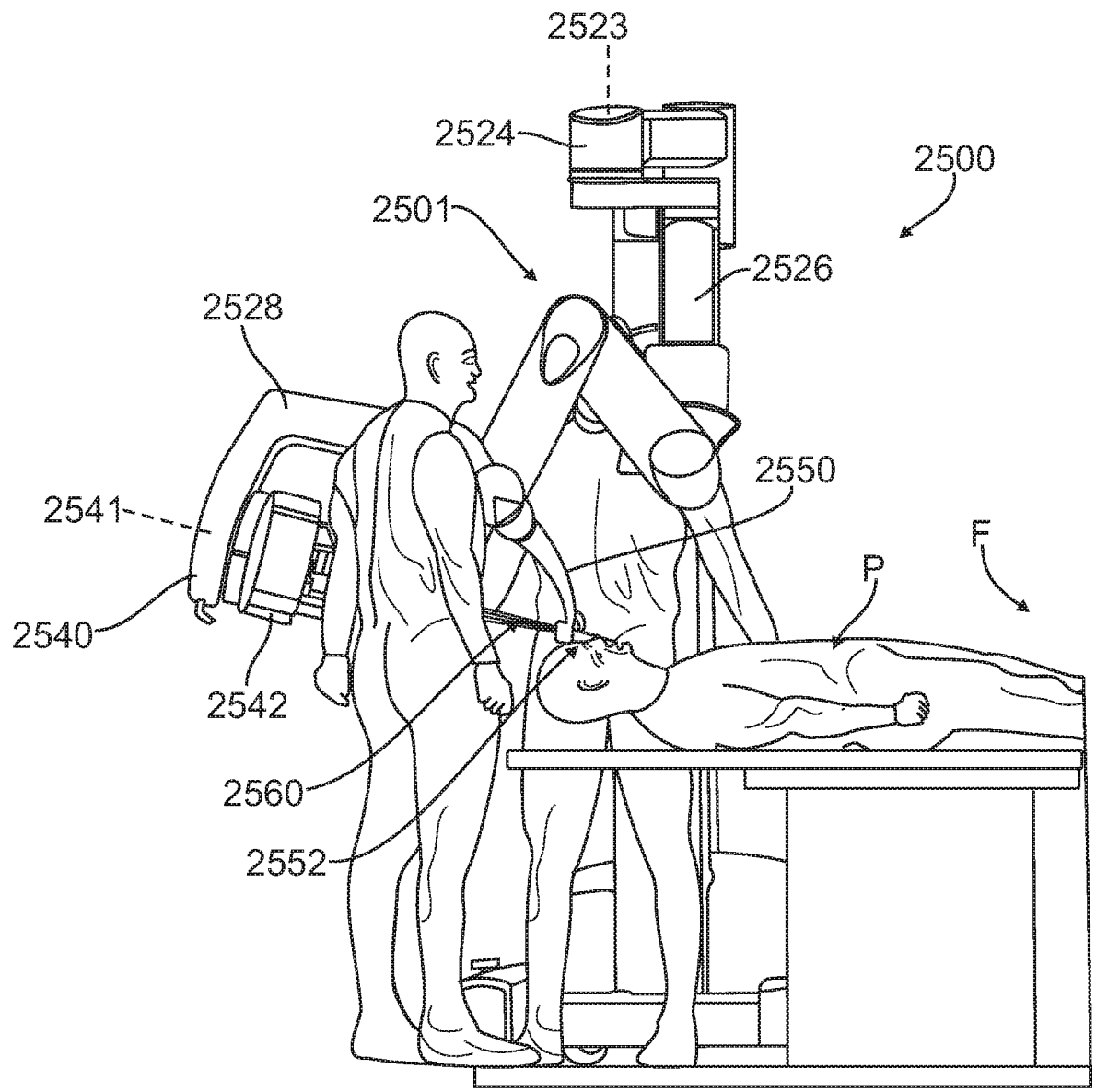
Figure 26C:
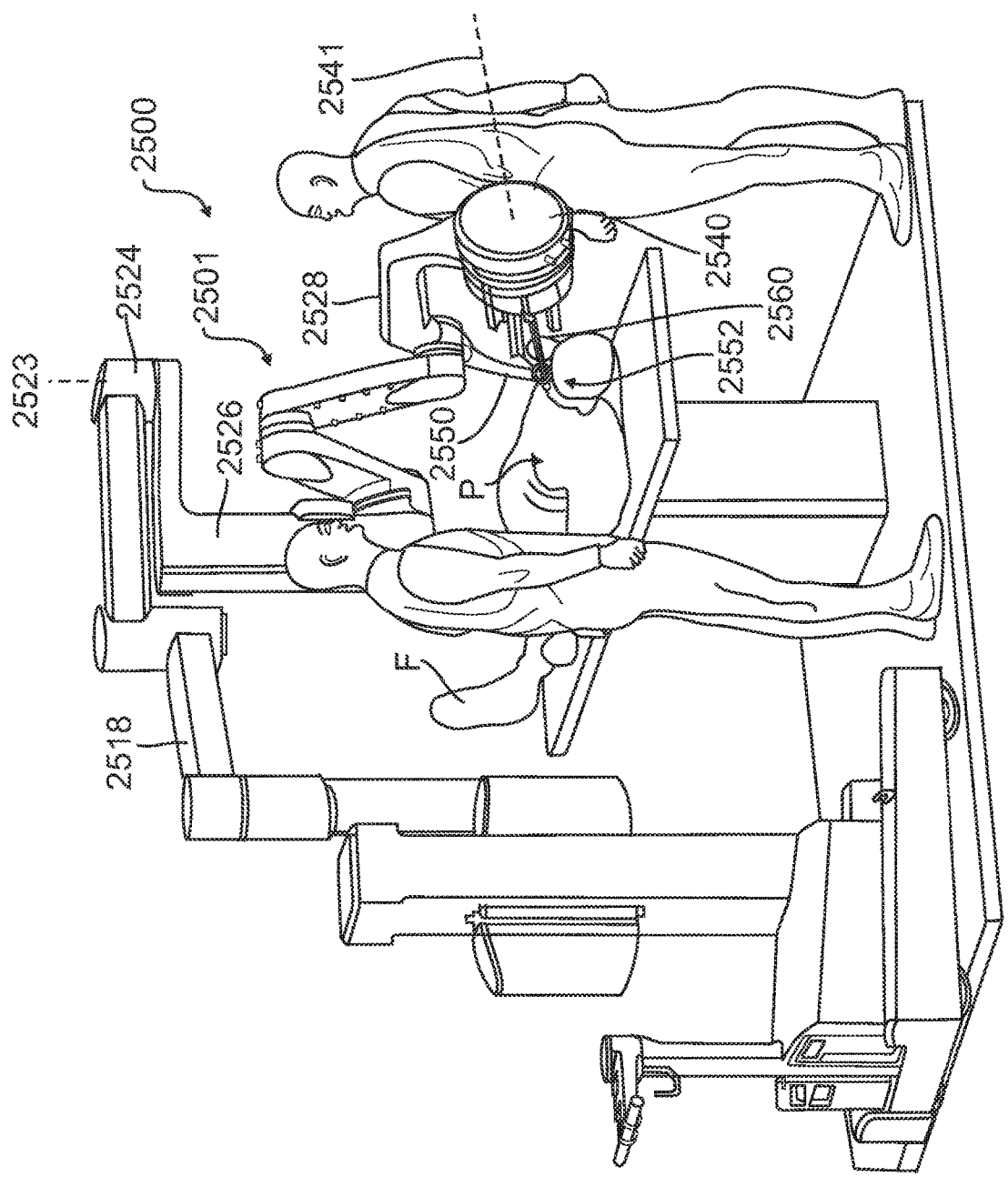

It can be seen that a vertical yaw axis 223 allows link 226 to rotate substantially 360 degrees, as shown by dashed lines 249 (FIG. 2C). In one instance the manipulator assembly yaw rotation may be continuous, and in another instance the manipulator assembly yaw rotation is approximately .+-. 180 degrees. In yet another instance, the manipulator assembly yaw rotation may be approximately 660 degrees. The pitch axis 239 may or may not be held constant during such yaw axis rotation. Since the instruments are inserted into the patient in a direction generally aligned with manipulator assembly roll axis 241, the arm can be actively controlled to position and reposition the instrument insertion direction in any desired direction around the manipulator assembly yaw axis (see, e.g., FIGS. 25A-25C showing the instrument insertion direction toward a patient's head, and FIGS. 26A-26C showing the instrument insertion direction toward a patient's feet). This capability may be significantly beneficial during some surgeries. In certain abdominal surgeries in which the instruments are inserted via a single port positioned at the umbilicus, for example, the instruments may be positioned to access all four quadrants of the abdomen without requiring that a new port be opened in the patient's body wall. Multi-quadrant access may be required for, e.g., lymph node access throughout the abdomen. In contrast, the use of a multi-port telerobotic surgical system may require that additional ports be made in the patient's body wall to more fully access other abdominal quadrants.

Figure 27A:
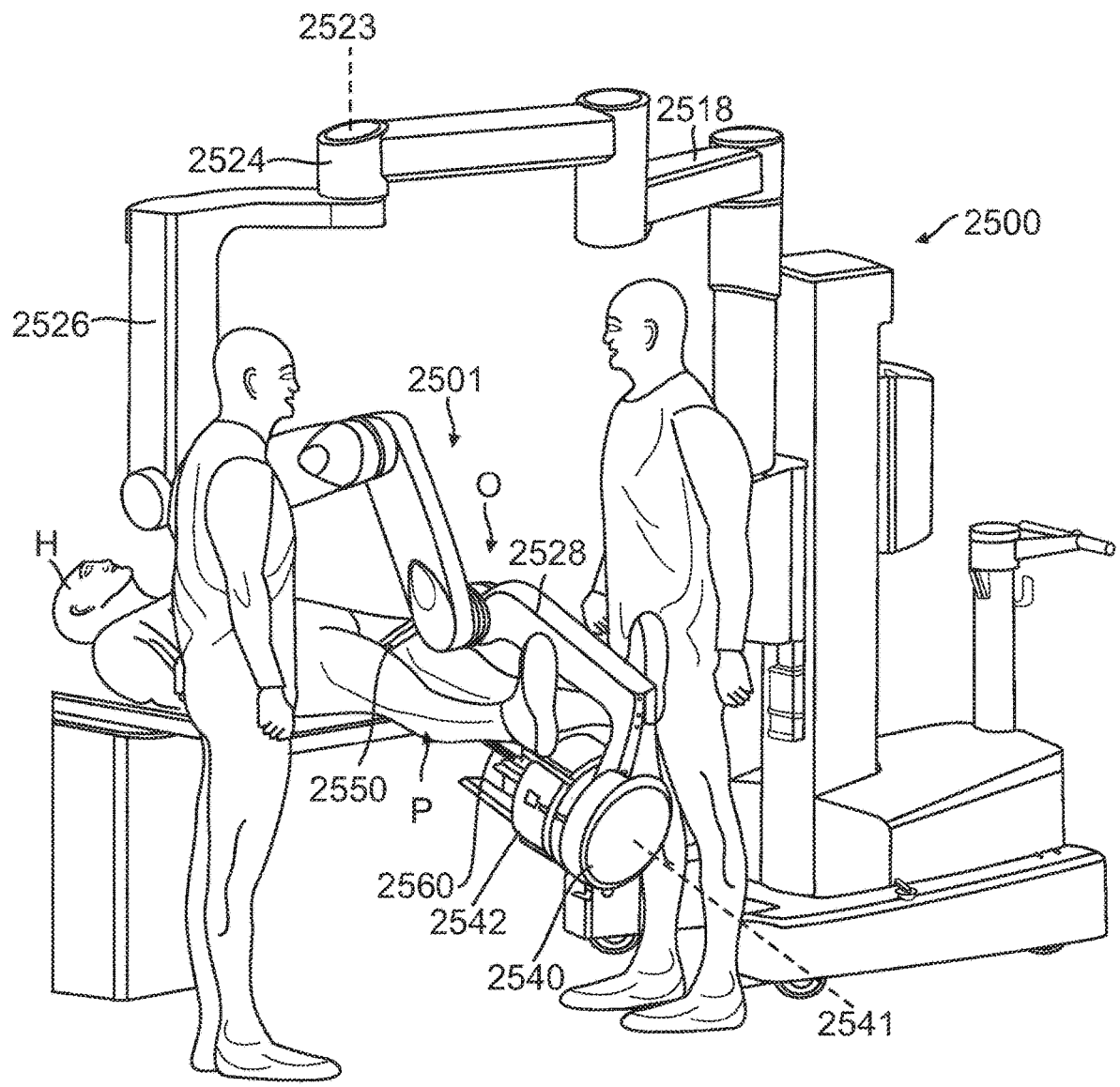
Figure 27B:
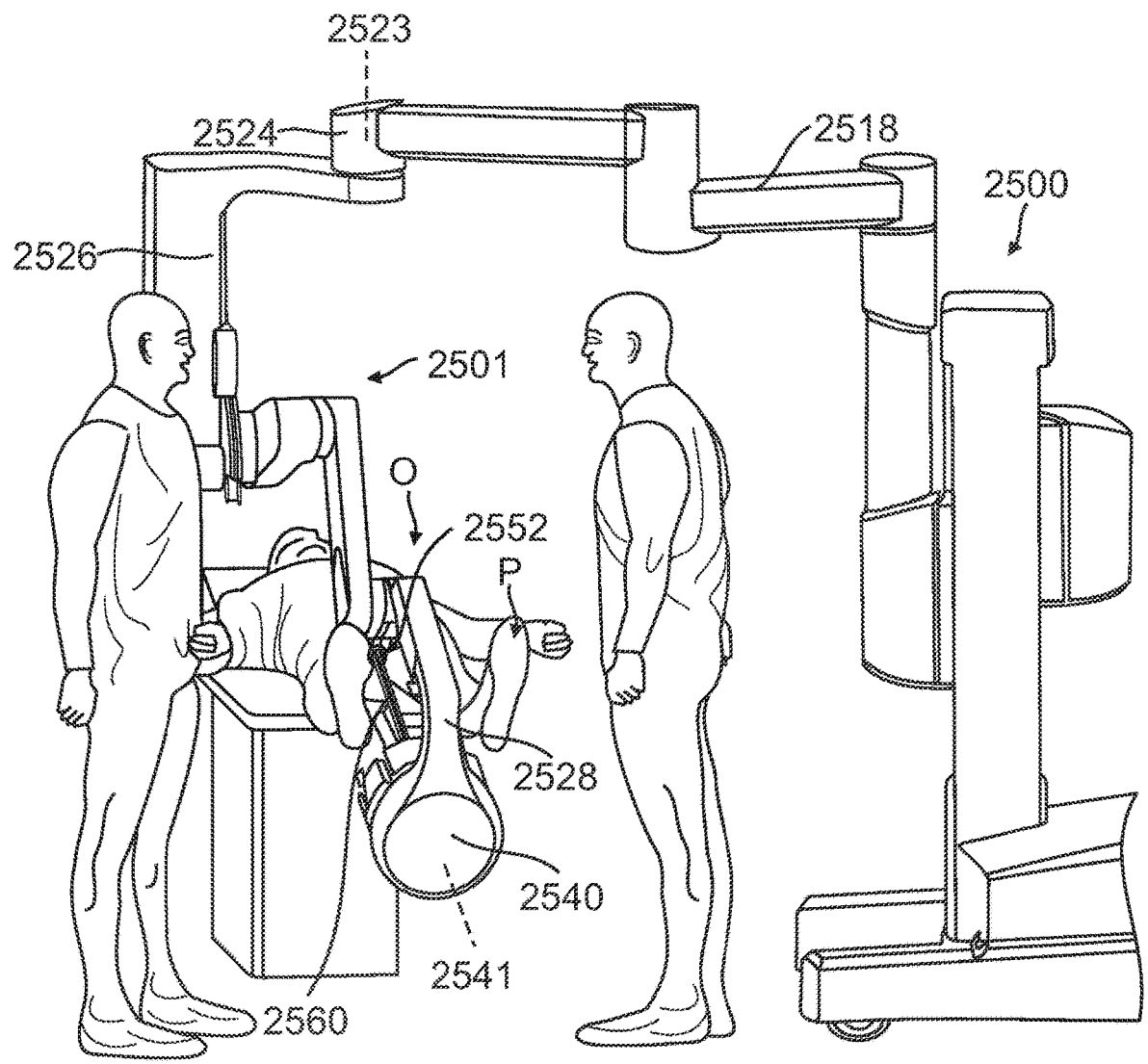
Figure 27C:
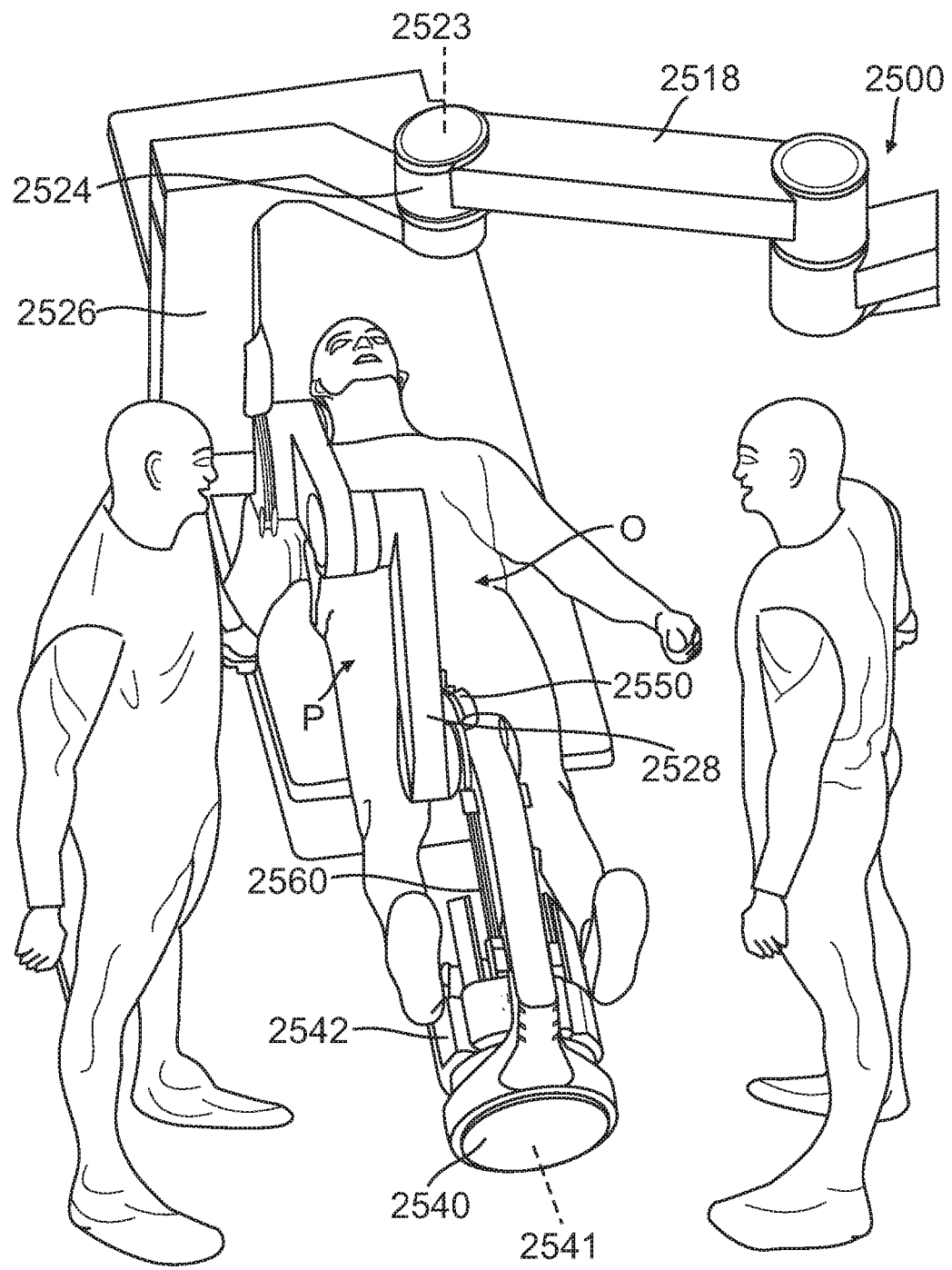

Additionally, the manipulator may direct the instrument vertically downwards and in a slightly pitched upwards configuration (see, e.g., FIGS. 27A-27C showing the instrument insertion direction pitched upwards). Thus, the angles of entry (both yaw and pitch about the remote center) for an instrument through a single entry port may be easily manipulated and altered while also providing increased space around the entry port for patient safety and patient-side personnel to maneuver.

Furthermore, links 230, 234, and 238 in conjunction with active joints 228, 232, and 236 may be used to easily manipulate the pitch angle of entry of an instrument through the single entry port while creating space around the single entry port. For example, links 230, 234, and 238 may be positioned to have a form factor "arcing away" from the patient. Such arcing away allows rotation of the manipulator arm about the yaw axis 223 that does not cause a collision of the manipulator arm with the patient. Such arcing away also allows patient side personnel to easily access the manipulator for exchanging instruments and to easily access the entry port for inserting and operating manual instruments (e.g., manual laparoscopic instruments or retraction devices). In yet another example, fourth link 238 has a form factor that arcs away from the remote center of motion and therefore the patient, allowing for greater patient safety. In other terms, the work envelope of the cluster of instrument manipulators 242a may approximate a cone, with the tip of the cone at the remote center of motion 246 and the circular end of the cone at the proximal end of the instrument manipulators 242a. Such a work envelope results in less interference between the patient and the surgical robotic system, greater range of motion for the system allowing for improved access to the surgical site, and improved access to the patient by surgical staff.

Accordingly, the configuration and geometry of the manipulator arm assembly 201 in conjunction with its large range of motion allow for multi-quadrant surgery through a single port. Through a single incision, the manipulator may direct the instrument in one direction and easily change direction; e.g., working toward the head or pelvis of a patient (see, e.g., FIGS. 25A-25C) and then changing direction toward the pelvis or head of the patient (see, e.g., FIGS. 26A-26C), by moving the manipulator arm about the constantly vertical yaw axis.

This illustrative manipulator arm assembly is used, for example, for instrument assemblies that are operated to move with reference to the remote center of motion. Certain setup and active joints and links in the manipulator arm may be omitted, or joints and links may be added for increased degrees of freedom. It should be understood that the manipulator arm may include various combinations of links, passive, and active joints (redundant DOFs may be provided) to achieve a necessary range of poses for surgery. Furthermore, various surgical instruments alone or instrument assemblies including guide tubes, multiple instruments, and/or multiple guide tubes, and instruments coupled to instrument manipulators (actuator assemblies) via various configurations (e.g., on a proximal face or a distal face of the actuator assembly or transmission mechanism), are applicable in the present disclosure.

Figures 1, 5A:
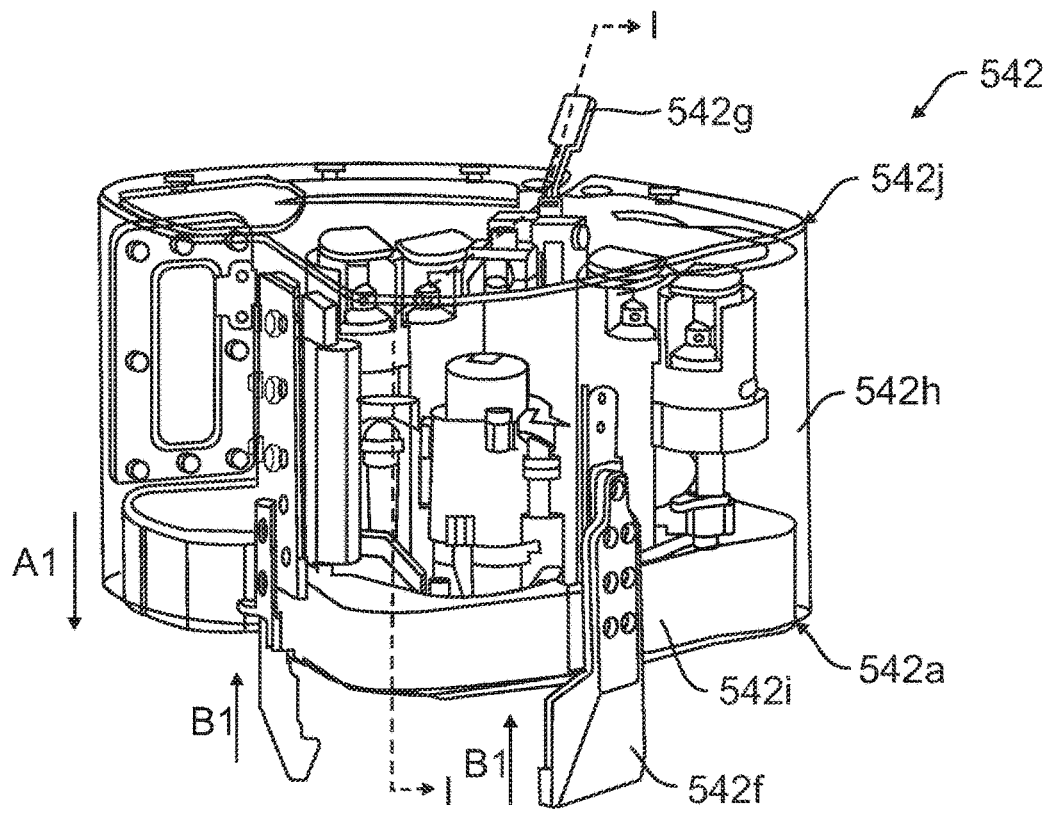
FIGS. 5A-1 and 5B-1 illustrate operation of support hooks to couple a proximal face of an instrument transmission mechanism to a distal face of the instrument manipulator.
Figures 1, 5B:
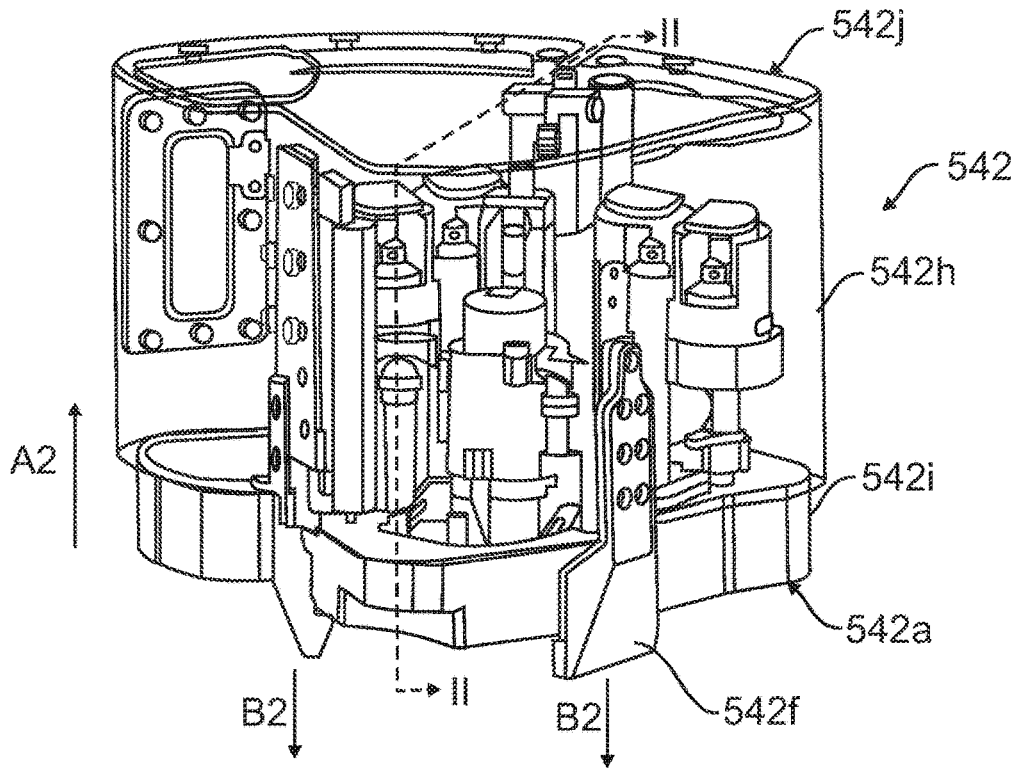
Figures 2, 5A:
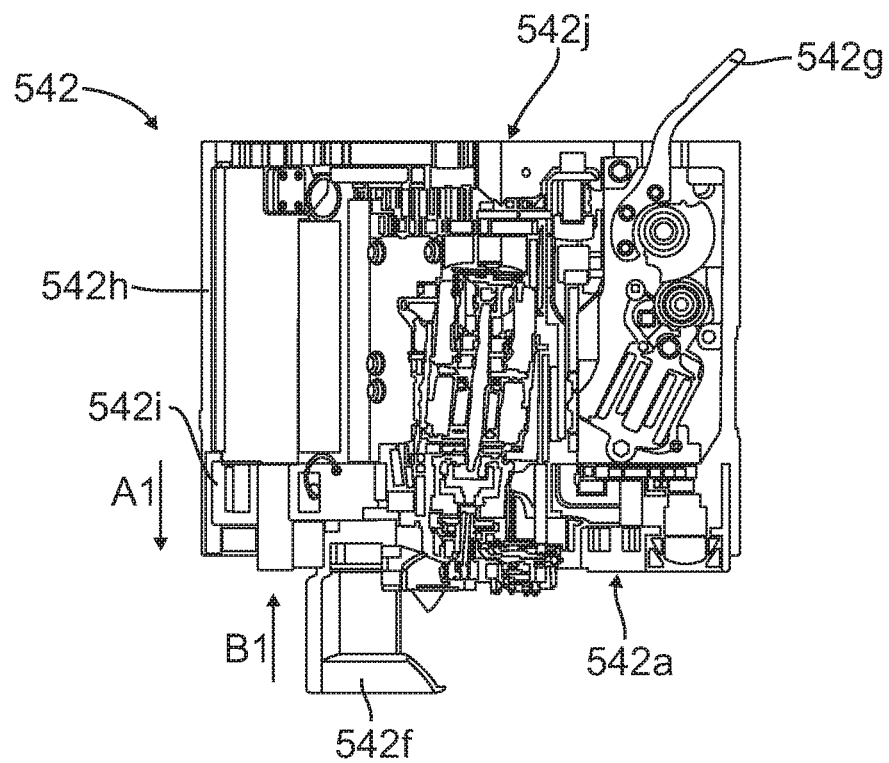
Figures 2, 5B:
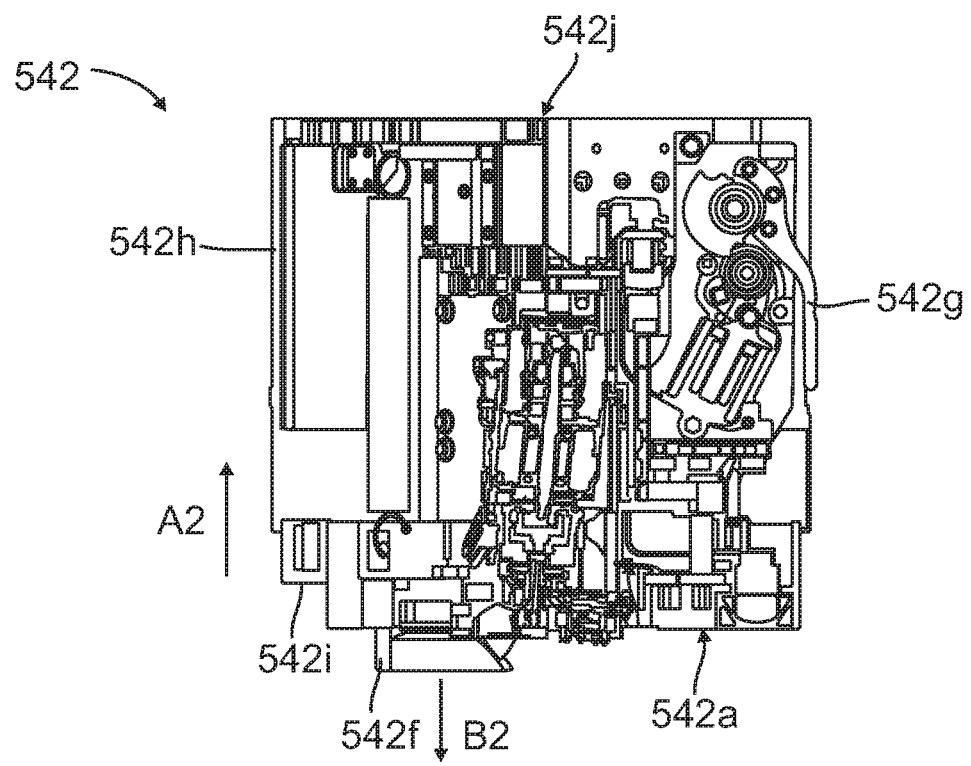
Figures 1, 5C:
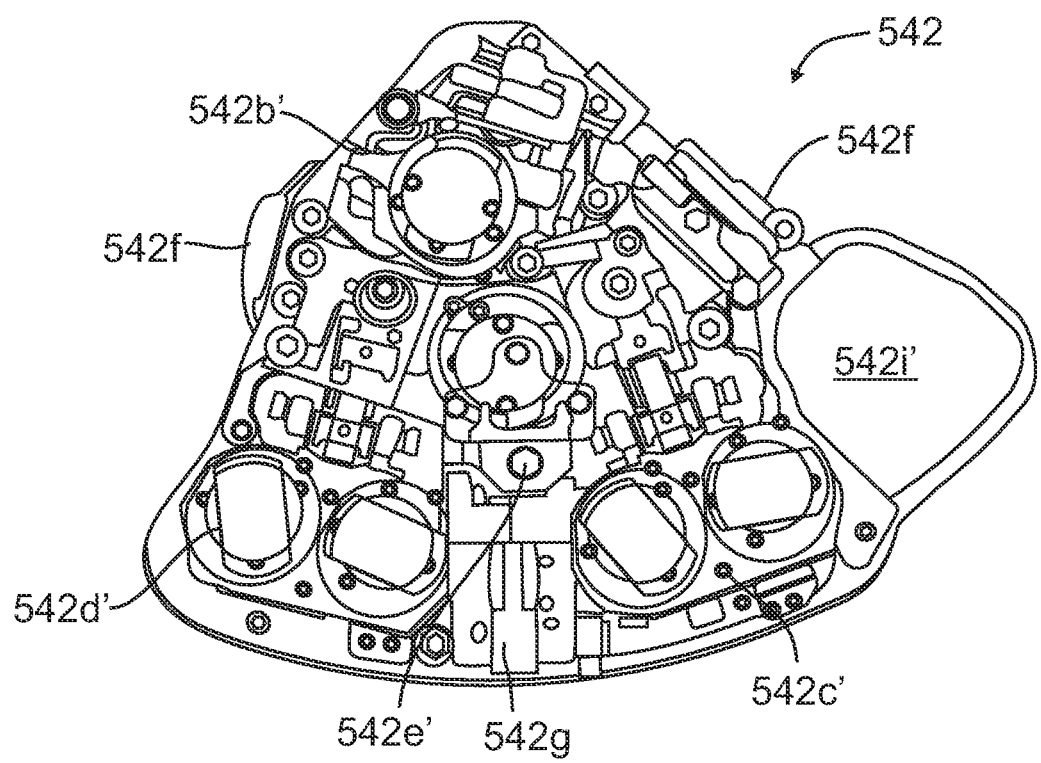
Figures 2, 5C:
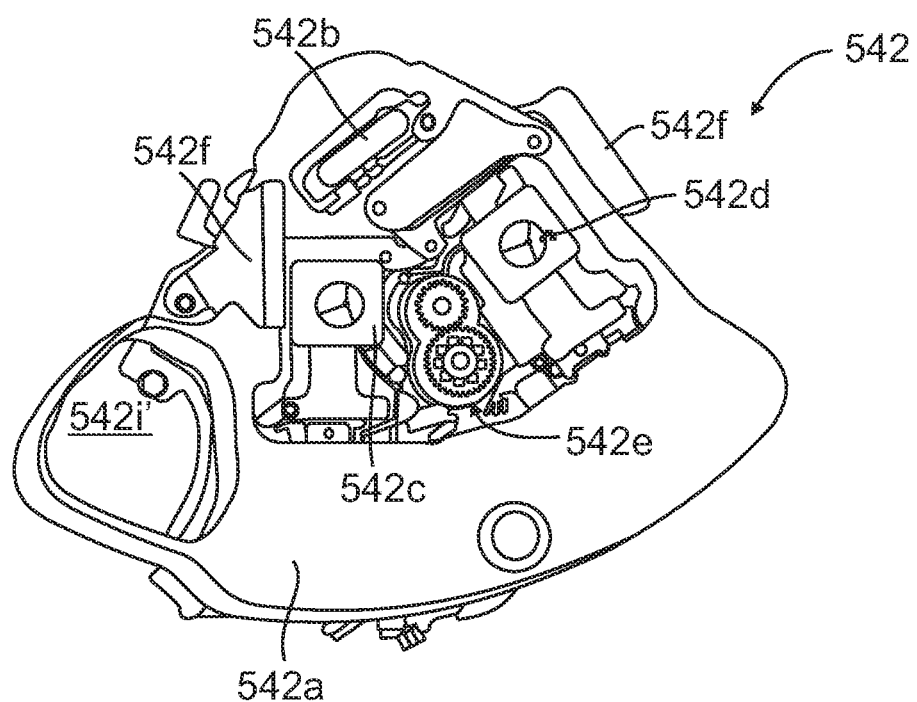
Figures 3, 5C:
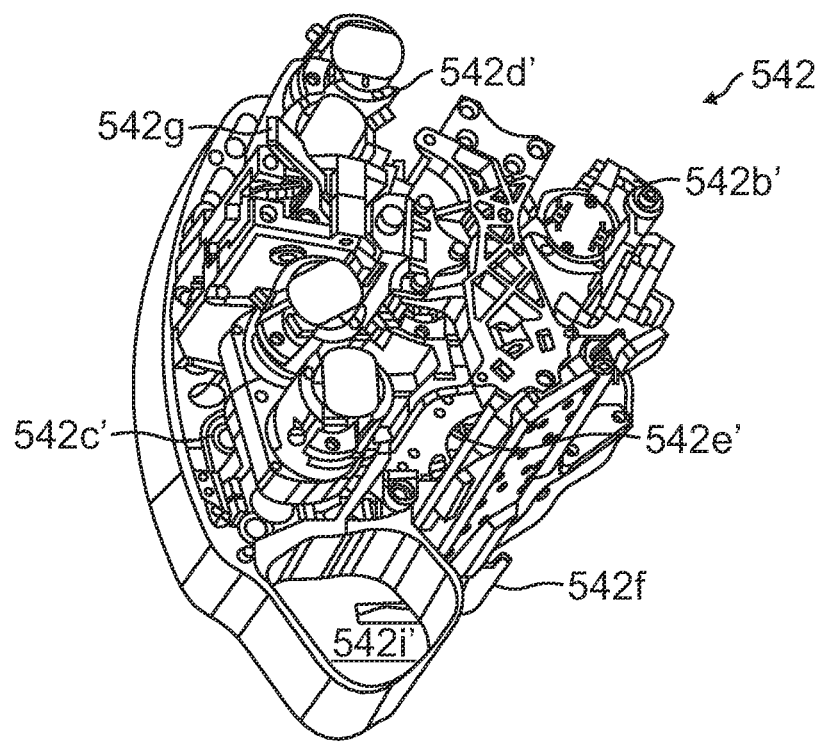

Referring now to FIGS. 3, 4A-4B, 5A-1 through 5B-2, 5C-1 through 5C-4, and 8, aspects and embodiments of the instrument manipulator will be described in greater detail with no intention of limiting the disclosure to these aspects and embodiments. FIG. 3 is a perspective view of an embodiment of a rotatable base plate 340a of a manipulator assembly platform, a cluster of four instrument manipulators 342 mounted on the base plate 340a to form an instrument manipulator assembly, and four instruments 360 (the proximal portions are illustrated) each mounted to the distal face of an associated instrument manipulator 342. Base plate 340a is rotatable about a manipulator assembly roll axis 341, as described above. In one embodiment, roll axis 341 runs through the longitudinal center of a cannula and entry guide assembly, through which the instruments 360 enter a patient's body. Roll axis 341 is also substantially perpendicular to a substantially single plane of the distal face of each instrument manipulator 342, and consequently to a substantially single plane of the proximal face of an instrument mounted to the distal face of an instrument manipulator.

Figure 8:
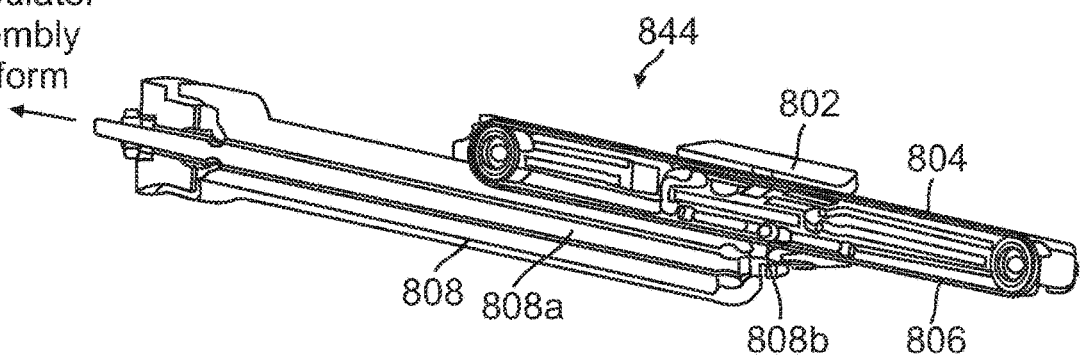
FIG. 8 illustrates a view of a telescopic insertion axis of the instrument manipulator in accordance with an embodiment of the present disclosure.

Each instrument manipulator 342 includes an insertion mechanism 344 that is coupled to the base plate 340a. FIG. 8 is a cutaway perspective view that illustrates an embodiment of the instrument insertion mechanism in more detail. As shown in FIG. 8, an instrument insertion mechanism 844 includes three links that slide linearly with reference to one another in a telescoping manner. Insertion mechanism 844 includes a carriage 802, a carriage link 804, and a base link 808. As described in U.S. patent application Ser. No. 11/613,800 (filed Dec. 20, 2006; U.S. Patent Application Pub. No. US 2007/0137371 A1), which is incorporated herein by reference, carriage link 804 slides along base link 808, and carriage 802 slides along carriage link 804. Carriage 802 and links 804,808 are interconnected by a coupling loop 806 (which in one instance includes one or more flexible metal belts; alternatively, one or more cables may be used). A lead screw 808a in base link 808 drives a slider 808b that is coupled to a fixed location on coupling loop 806. Carriage 802 is coupled to coupling loop 806 at a fixed location as well, so that as slider 808b slides a particular distance x with reference to base link 808, carriage 802 slides 2x with reference to base link 808. Various other linear motion mechanisms (e.g., lead screw and carriage) may be used in alternate implementations of the insertion mechanism.

As shown in FIGS. 3 and 8, the proximal end of base link 808 is coupled to rotatable base plate 340a, and carriage 802 is coupled to the outer shell or inner frame of an instrument manipulator 342 (e.g., within inner frame aperture 542i' of FIGS. 5C-1 through 5C-3). A servomotor (not shown) drives lead screw 808a, and as a result the instrument manipulator 342 moves proximally and distally with reference to base plate 340a in a direction generally parallel to roll axis 341. Since a surgical instrument 360 is coupled to the manipulator 342, the insertion mechanism 344 functions to insert and withdraw the instrument through the cannula towards and away from the surgical site (instrument insertion DOF). Flat electrically conductive flex cables (not shown) running adjacent the coupling loop may provide power, signals, and ground to the instrument manipulator.

It can be seen that an advantage of the telescoping feature of the insertion mechanism 344 is that it provides a larger range of motion when the instrument manipulator moves from its full proximal to its full distal position, with a smaller protruding insertion mechanism when the manipulator is at its full proximal position, than if only a single stationary insertion stage piece is used (see e.g., FIGS. 4A (full distal position) and 4B (full proximal position)). The shortened protrusion prevents the insertion mechanism from interfering with the patient during surgery and with operating room personnel, e.g., during instrument changing, when the instrument manipulator is at its proximal position.

As further illustrated in FIG. 3, the telescopic insertion mechanisms 344 are symmetrically mounted to the rotatable base plate 340a in one embodiment, and therefore the instrument manipulators 342 and mounted instruments 360 are clustered symmetrically about the roll axis 341. In one embodiment, instrument manipulators 342 and their associated instruments 360 are arranged around the roll axis in a generally pie-wedge layout, with the instrument shafts positioned close to the manipulator assembly roll axis 341. Thus, as the base plate rotates about the roll axis 341, the cluster of instrument manipulators 342 and mounted instruments 360 also rotates about the roll axis.

FIGS. 4A and 4B are perspective views that illustrate an instrument manipulator 442 at an extended and retracted position, respectively, along an insertion mechanism 444 mounted to a rotatable base plate 440a. As noted above, instrument manipulator 442 is able to extend and retract along a longitudinal axis of the insertion mechanism 444 between the base plate 440a and a free distal end 444a of the insertion mechanism, as shown by the double-sided arrows adjacent to insertion mechanism 444. In this illustrative embodiment, instruments mount against the distal face 442a of the instrument manipulator 442.

Distal face 442a includes various actuation outputs that transfer actuation forces to a mounted instrument. As shown in FIGS. 4A and 4B, such actuation outputs may include a grip output lever 442b (controlling the grip motion of an instrument end effector), a joggle output gimbal 442c (controlling the side-to-side motion and the up-and-down motion of a distal end parallel linkage ("joggle" or "elbow" mechanism)), a wrist output gimbal 442d (controlling the yaw motion and the pitch motion of an instrument end effector), and a roll output disk 442e (controlling the roll motion of an instrument). Details of such outputs, and the associated parts of the instrument force transmission mechanism that receives such outputs, may be found in U.S. patent application Ser. No. 12/060,104 (filed Mar. 31, 2008; U.S. Patent Application Pub. No. US 2009/0248040 A1), which is incorporated herein by reference. Examples of the proximal ends of illustrative surgical instruments that may receive such inputs may be found in U.S. patent application Ser. No. 11/762,165, which is referenced above. Briefly, the side-to-side and up-and-down DOFs are provided by a distal end parallel linkage, the end effector yaw and end effector pitch DOFs are provided by a distal flexible wrist mechanism, the instrument roll DOF is provided by rolling the instrument shaft while keeping the end effector at an essentially constant position and pitch/yaw orientation, and the instrument grip DOF is provided by two movable opposing end effector jaws. Such DOFs are illustrative of more or fewer DOFs (e.g., in some implementations a camera instrument omits instrument roll and grip DOFs).

In order to facilitate the mounting of an instrument against the instrument manipulator's distal face, supports such as support hooks 442f are positioned on the instrument manipulator. In the depicted embodiment, the support hooks are stationary with reference to the instrument manipulator's main housing, and the instrument manipulator's distal face moves proximally and distally to provide a secure interconnection between the instrument manipulator and the instrument. A latch mechanism 442g is used to move the instrument manipulator's distal face toward an instrument's proximal face. In an alternative embodiment, a latch mechanism may be used, to move the instrument's proximal face toward the manipulator's distal face in order to engage or disengage the manipulator outputs and instrument inputs.

FIGS. 5A-1 and 5B-1 are perspective views that illustrate an exemplary architecture of an instrument manipulator 542. FIGS. 5A-2 and 5B-2 are cross-sectional views of FIGS. 5A-1 and 5B-1 along cut lines I-I and II-II, respectively. As shown, the manipulator includes an inner frame 542i movably coupled to an outer shell 542h, for example by sliding joints, rails, or the like. Inner frame 542i moves distally and proximally with reference to outer shell 542h as the result of the action of latch mechanism 542g.

Referring now to FIGS. 5A-1 through 5B-2, the operation of support hooks 542f and latch mechanism 542g to mount an instrument (not shown) to the instrument manipulator 542 is illustrated. As shown, a distal face 542a of the instrument manipulator 542 is substantially a single plane, and it is operably coupled to a proximal face of an instrument force transmission mechanism (e.g., proximal face 960' of instrument 960 in FIGS. 9A-9B). Latch mechanism 542g may include an actuation mechanism, such as a pulley and wire, to move the inner frame and outer shell of the instrument manipulator relative to one another, and to hold distal face 542a against the instrument during operation.

In the depicted embodiment, instrument support hooks 542f are rigidly mounted to instrument manipulator outer shell 542h, and when latch mechanism 542g is actuated, the distal face 542a of the inner frame 542i of the instrument manipulator moves distally toward a distal end of support hooks 542f and away from a proximal face 542j of the outer shell of the instrument manipulator. Thus, when an instrument force transmission mechanism is mounted on the support hooks 542f, distal face 542a of the instrument manipulator moves toward the proximal face of the instrument transmission mechanism, which is restrained by support hooks 542f, in order to engage or otherwise operably interface the instrument manipulator outputs with the instrument force transmission inputs, as illustrated by arrow A1 in FIGS. 5A-1 and 5A-2. As illustrated by this embodiment, actuator outputs of the manipulator compress against and interface with the proximal instrument face to transmit instrument actuator signals to the instrument. When the latch 542g is actuated in a reverse direction, distal face 542a of the instrument manipulator moves toward proximal face 542j of the instrument manipulator (i.e., away from distal ends of stationary support hooks 5420 in order to disengage the instrument manipulator outputs from the instrument inputs, as illustrated by arrow A2 in FIGS. 5B-1 and 5B-2. An advantage of the depicted embodiment is that when the latch mechanism is activated, the actuator portions of the instrument manipulator move relative to a stationary instrument fixed in space on the support hooks. The movement of the instrument manipulator's actuators toward or away from the instrument minimizes unnecessary or unintended instrument motion during the latching or unlatching process. Accordingly, since the instrument does not move relative to the patient during the instrument mounting process, potential damage to tissue is avoided, since the distal end of the instrument may still be inside the patient.

In alternate embodiments, the support hooks 542f may be retracted toward proximal face 542j to move a proximal face of an instrument toward the distal face 542a of a stationary instrument manipulator in order to engage the instrument manipulator outputs with the instrument inputs, as shown by arrows B1 in FIGS. 5A-1 and 5A-2. When the latch is opened or reversely actuated, the process is reversed and the support hooks 542f move away from the distal face 542a of the stationary instrument manipulator in order to disengage the instrument manipulator outputs with the instrument inputs, as illustrated by arrows B2 in FIGS. 5B-1 and 5B-2.

Figures 4, 5C:
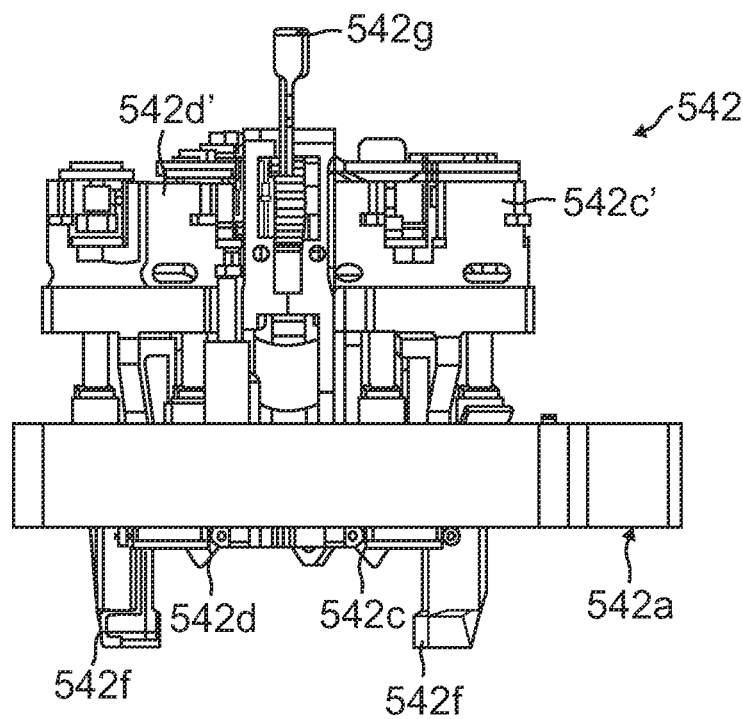

FIGS. 5C-1 through 5C-4 illustrate different views of the instrument manipulator 542 without outer shell 542h in order to reveal independent drive modules for actuating the instrument manipulator outputs. The drive modules are mounted in modular form to inner frame 542i of the instrument manipulator, which moves along with the drive modules, relative to outer shell 542h and support hooks 542f of the instrument manipulator. When the latch is closed, the inner frame of the instrument manipulator moves toward the instrument a set distance, and spring-loaded module outputs engage instrument inputs through a sterile drape, as further described below. When the latch is opened, the process is reversed. Spring-loaded actuator drive module outputs provide a robust interface with the instrument force transmission mechanism inputs through the drape, as described in more detail below.

As illustrated in the depicted embodiment, instrument manipulator 542 includes a grip actuator drive module 542b' for actuating a grip output lever 542b, a joggle actuator drive module 542c' for actuating a joggle output gimbal 542c, a wrist actuator drive module 542d' for actuating wrist output gimbal 542d, and a roll actuator drive module 542e' for actuating a roll output disc 542e. Outputs 542b, 542c, 542d, and 542e distally protrude from the distal face 542a of instrument manipulator 542, as shown for example in FIG. 5C-4, and they are adapted to engage with instrument force transmission mechanism inputs to actuate X-Y translation of the mounted instrument and grip, pitch, yaw, and roll end effector movements.

Figures 6A, 6B:
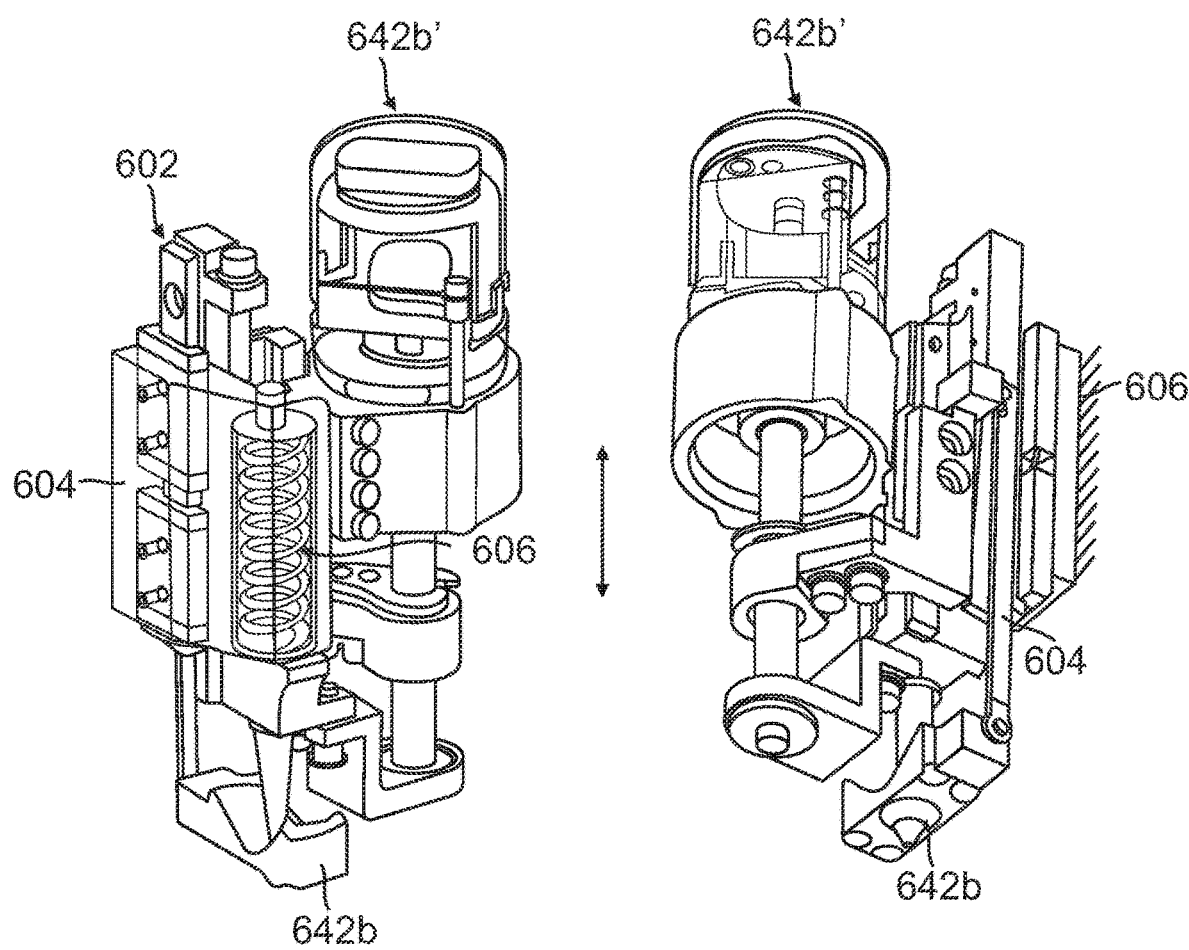
FIGS. 6A-6B illustrate different views of a grip module of the instrument manipulator in accordance with an embodiment of the present disclosure.

FIGS. 6A-6B are upper and lower perspective views of a grip actuator drive module 642b' of an instrument manipulator. Grip actuator drive module 642b' includes a linear slide 602, a drive spring mechanism 604 that includes a spring 606, and a grip drive output lever 642b. Drive spring mechanism 604 is coupled to the inner frame 542i of the instrument manipulator. As the latch 542g is actuated to engage an instrument, the inner frame moves, and the grip drive module 642b' moves along linear slide 602 until output lever 642b contacts its mating input on the instrument. This contact preloads the spring 606, thereby spring-loading the grip output 642b against an instrument input as the instrument is latched in place. The preloaded spring 606 then ensures that proper actuator drive output/input contact is maintained during operation, so that a clearance does not develop in the output/input contact, which would render precise kinematic control difficult.

Figure 7A:
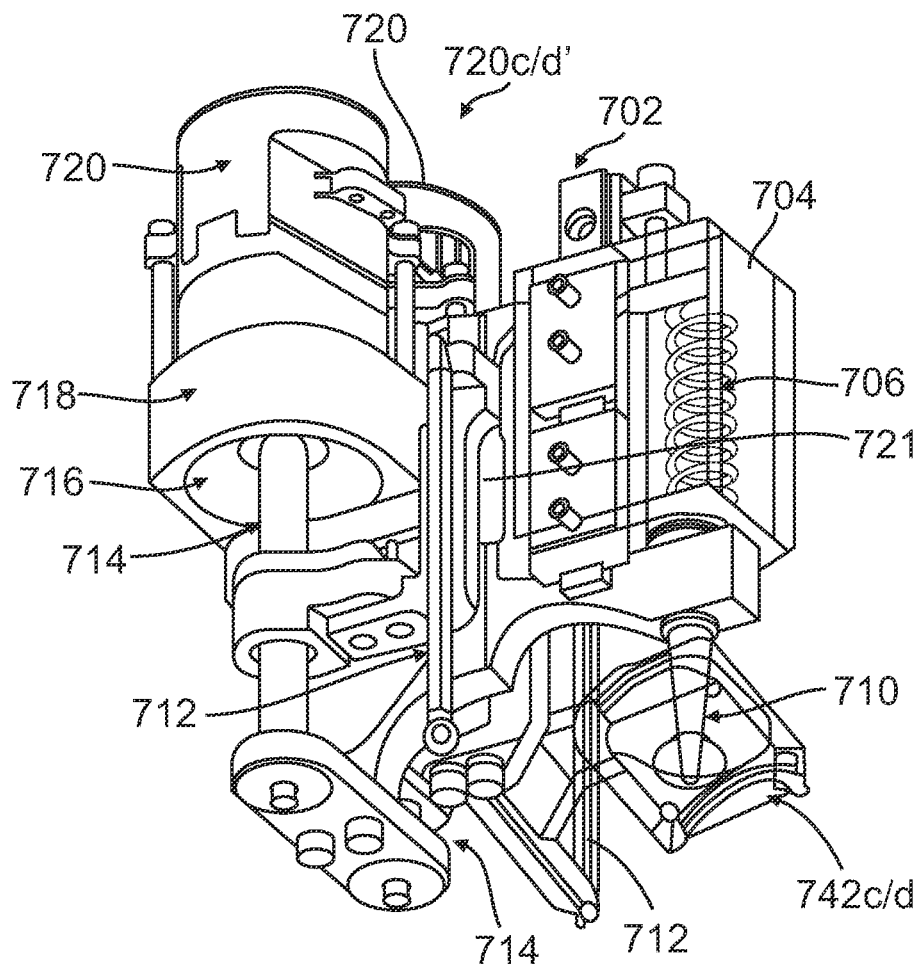
FIG. 7A illustrates a view of a gimbal actuator module of the instrument manipulator in accordance with an embodiment of the present disclosure.

FIG. 7A is a bottom perspective view of a gimbal drive module 742c/d' of the instrument manipulator that can be used to provide either the joggle output gimbal controlling X-Y translation for the joggle mechanism of the instrument or the wrist output gimbal controlling pitch and yaw for the instrument end effector. In this embodiment, gimbal drive module 742c/d' includes a linear slide 702, a drive spring mechanism 704 including a spring 706, and an actuator output gimbal 742c/d on a gimbal pin 710. Drive spring mechanism 704 is coupled to the inner frame 542i of the instrument manipulator. As latch 542f is actuated to engage an instrument, the inner frame moves distally, and actuator drive module 742c/d' moves along linear slide 702 until output gimbal 742c/d contacts its mating input on the instrument. This contact preloads the spring 706, thereby spring-loading the output gimbal 742c/d against an instrument input as the instrument is latched in place. As with the grip actuator drive module, the preloaded spring then ensures that proper actuator drive output/input contact is maintained during operation, so that a clearance does not develop in the output/input contact, which would render precise kinematic control difficult. Gimbal drive module 742c/d' further includes two "dog bone" links 712, two ball screws 714, two motors 716, two Hall effect sensors 718, and two rotary or linear motion encoders 720. Motors 716 drive associated ball screws 714, which actuate dogbone links 712. The proximal end of dogbone links 712 are coupled to linear slides 721, which move along axes parallel to ball screws 714. The distal end of dogbone lines 712 are coupled to output gimbals 742c/d, which each rotate about two orthogonal axes perpendicular to the longitudinal axis through gimbal pin 710. In one aspect, the gimbals of the drive modules have two degrees of freedom but do not have orthogonal axes.

Figure 7B:
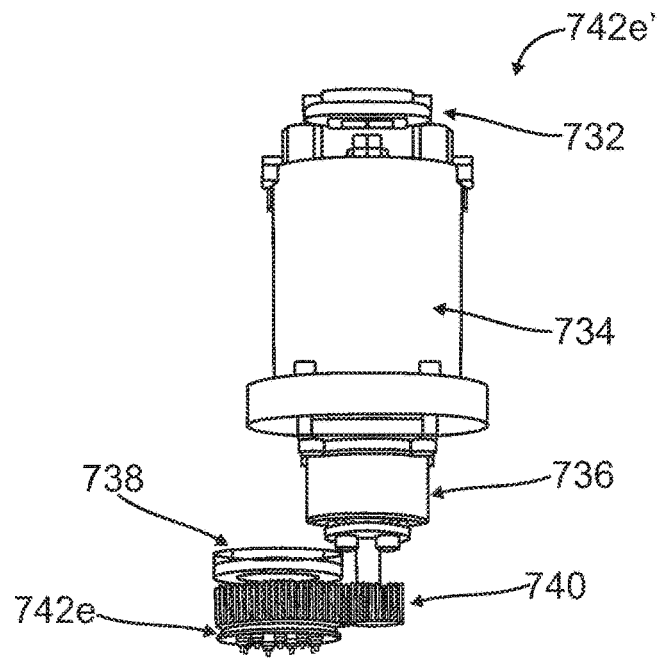
FIG. 7B illustrates a view of a roll module of the instrument manipulator in accordance with an embodiment of the present disclosure.

FIG. 7B is a bottom perspective view of a roll actuator drive module 742e' of the instrument manipulator that can be used to provide roll output disc controlling roll movement of a mounted instrument. In this embodiment, roll actuator drive module 742e' includes a motor 734 which drives a harmonic drive 736, which in turn drives spur gears 740. The spur gears 740 rotate the roll output disc 742e and thus drive the roll input disc on the instrument. An encoder 732 is used to sense position and commutate the motor 734. An absolute encoder 738 is coupled to the roll output disc 742e and senses the absolute position of instrument roll.

In one aspect, the system drive modules are operably independent and sufficiently isolated from one another, such that large forces applied through one interface output are not transferred to the other interface outputs. In other words, large forces through one interface output do not transfer to other interface outputs, and so do not affect the instrument components actuated by the other interface outputs. In one aspect, a drive module and its corresponding actuator outputs have substantially no unintended force input from another drive module and/or its corresponding actuator outputs. This feature improves instrument operation and consequently patient safety.

Figure 9A:
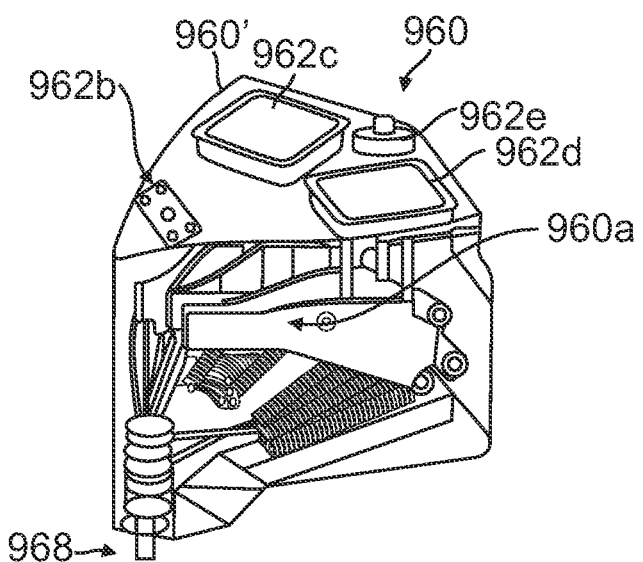
FIGS. 9A and 9B illustrate perspective views of a proximal portion and a distal portion, respectively, of an instrument configured to mount to an instrument manipulator.
Figure 9B:
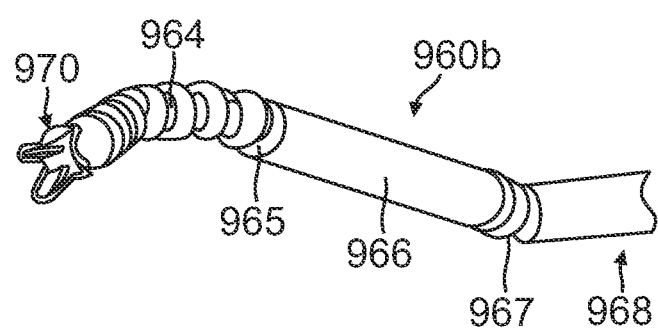

FIGS. 9A and 9B are perspective views of a proximal portion 960a and a distal portion 960b, respectively, of an instrument 960 configured to mount to the instrument manipulators of FIGS. 4A-4B and 5A-1 through 5C-4. A proximal face 960' of a transmission mechanism of instrument 960 includes an instrument grip input lever 962b that interfaces with grip output lever 542b, an instrument joggle input gimbal 962c that interfaces with joggle output gimbal 542c, an instrument wrist input gimbal 962d that interfaces with wrist output gimbal 542d, and an instrument roll input disc 962e that interfaces with roll output disc 542e. FIG. 9B illustrates an example of a distal end 960b of a flexible surgical instrument 960 including a wrist 964, a joggle mechanism 966, and an end effector 968. In one embodiment, proximal face 960' of the transmission mechanism of instrument 960 has a substantially single plane that operably interfaces with the distal face of the instrument manipulator when the manipulator outputs and instrument inputs are operably engaged. U.S. patent application Ser. No. 11/762,165 entitled "Minimally Invasive Surgical System" by Larkin et al., which is incorporated herein by reference, and U.S. patent application Ser. No. 11/762,154 entitled "Surgical Instrument With Parallel Motion Mechanism" by Cooper et al., which is incorporated herein by reference, disclose further details on applicable distal portions and proximal portions of surgical instruments, such as instrument 960.

In the illustrative aspect shown in FIGS. 9A and 9B, instrument 960 includes a transmission portion at its proximal end, an elongated instrument body, one of various surgical end effectors 968, and a snake-like, two degree of freedom wrist mechanism 964 that couples end effector 968 to the joggle mechanism 966 and the instrument body. As in the da Vinci® Surgical Systems, in some aspects the transmission portion includes disks that interface with electrical actuators (e.g., servomotors) permanently mounted on a support arm so that instruments may easily be changed. Other linkages such as matching gimbal plates and levers may be used to transfer actuating forces at the mechanical interface. Mechanical mechanisms (e.g., gears, levers, gimbals) in the transmission portion transfer the actuating forces from the disks to cables, wires, and/or cable, wire, and hypotube combinations that run through one or more channels in the instrument body (which may include one or more articulated segments) to control wrist 964 and end effector 970 movement. In some aspects, one or more disks and associated mechanisms transfer actuating forces that roll the instrument body around its longitudinal axis. The main segment of the instrument body is a substantially rigid single tube, although in some aspects it may be slightly resiliently flexible. This small flexibility allows a proximal body segment proximal of a guide tube (i.e., outside the patient) to be slightly flexed so that several instrument bodies can be spaced more closely within a guide tube than their individual transmission segment housings would otherwise allow, like several cut flowers of equal length being placed in a small-necked vase. This flexing is minimal (e.g., less than or equal to about a 5-degree bend angle in one embodiment) and does not induce significant friction because the bend angle for the control cables and hypotubes inside the instrument body is small. In other words, in one embodiment, an instrument shaft may distally exit a force transmission mechanism at a slight angle instead of orthogonal to a distal or proximal face of the force transmission mechanism. The instrument shaft may then bend slightly and continue straight to form a slight arc at a proximal section of the instrument shaft distally exiting the force transmission mechanism. Thus, the instrument may have an instrument shaft with a proximal curved section proximal to the guide tube and a distal straight section. In one example, the instrument shaft may be pitched between about zero degrees and about five degrees when distally exiting the force transmission mechanism.

As shown in FIGS. 9A and 9B, instrument 960 includes a proximal body segment 968 (that extends through a guide tube in one example) and at least one distal body segment or joggle mechanism 966 (that is positioned beyond the guide tube's distal end in one example). For example, instrument 960 includes proximal body segment 968, joggle mechanism 966 that is coupled to proximal body segment 968 at a joint 967, wrist mechanism 964 that is coupled to joggle mechanism 966 at another joint 965 (the coupling may include another, short distal body segment), and an end effector 970. In some aspects the joggle mechanism 966 and joints 965 and 967 function as a parallel motion mechanism in which the position of a reference frame at the distal end of the mechanism may be changed with respect to a reference frame at the proximal end of the mechanism without changing the orientation of the distal reference frame. Details of an applicable parallel motion or joggle mechanism including related joints of an applicable instrument is further disclosed in U.S. patent application Ser. No. 11/762,165, which has been incorporated by reference.

Figure 10:
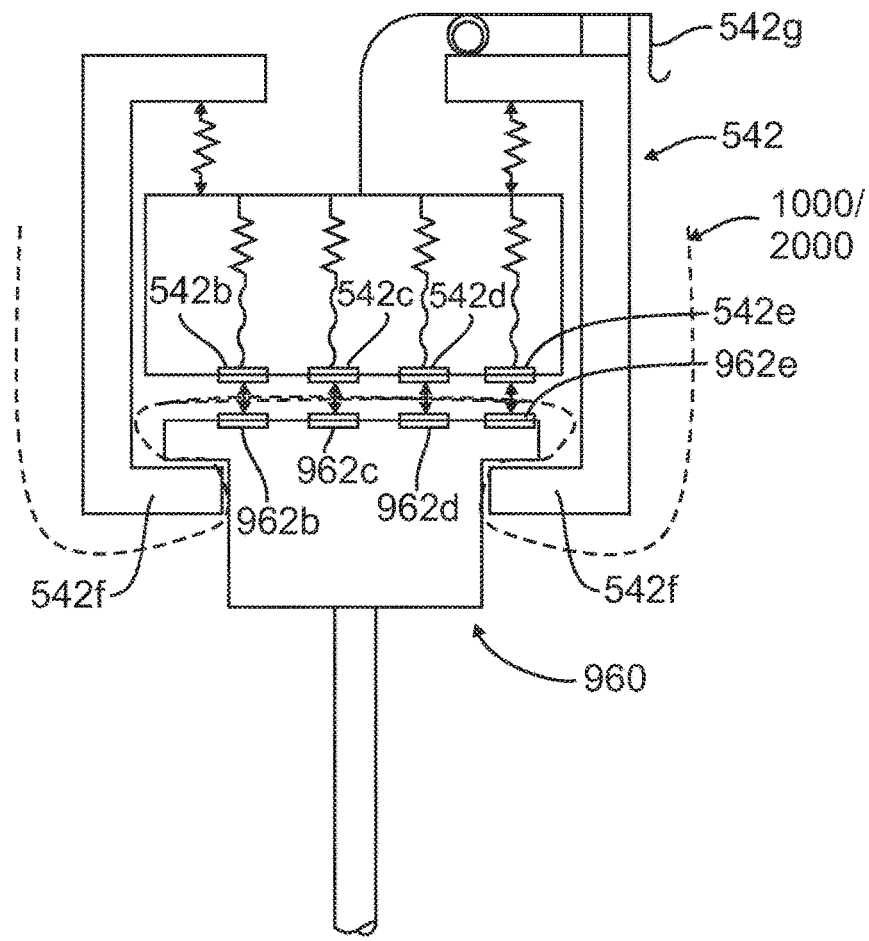
FIG. 10 illustrates a sectional diagram of an instrument manipulator operably coupled to an instrument in accordance with an embodiment of the present disclosure.

FIG. 10 is a cross-sectional side view of an instrument manipulator 542 operably coupled to an instrument 960 in accordance with aspects of the present disclosure. As shown in FIG. 10, actuator outputs 542$b$-542$e$ on a distal face of the instrument manipulator 542 interface with actuator inputs 962$b$-962$e$ on a proximal face of the surgical instrument 960.

Since the instrument end effector is provided with seven degrees of freedom (instrument insertion, grip, 2-DOF wrist articulation, 2-DOF joggle (wrist translation), and instrument roll) to facilitate surgery, the requirement for instrument actuation precision is high and a high-fidelity, low backlash interface between the instrument and the instrument manipulator is desirable. The independently operated drive system modules of the instrument manipulator (e.g., modules 542$b'$, 542$c'$, 542$d'$, and 542$e'$) allow the various drive trains to be coupled to a surgical instrument through an imprecisely manufactured drape substantially without performance comprise. As the drive system modules are not coupled to one another and sufficiently isolated from one another, large forces applied through one interface output are not transferred to the other interface outputs. In other words, large forces through one interface output do not transfer to other interface outputs, and so do not affect the instrument components actuated by the other interface outputs. In one aspect, a drive module and its corresponding actuator outputs have substantially no unintended force input from another drive module and/or its corresponding actuator outputs. This feature improves instrument operation and consequently patient safety.

In one aspect, mating disks may be used for force transmission features and actuating feature as in the da Vinci® Surgical System instrument interface. In another aspect, mating gimbal plates and levers are used. Various mechanical components (e.g., gears, levers, cables, pulleys, cable guides, gimbals, etc.) in the transmission mechanisms are used to transfer the mechanical force from the interface to the controlled element. Each actuator mechanism includes at least one actuator (e.g., servomotor (brushed or brushless)) that controls movement at the distal end of the associated instrument. For example, an actuator can be an electric servomotor that controls a surgical instrument's end effector grip DOF. An instrument (including a guide probe as described herein) or guide tube (or, collectively, the instrument assembly) may be decoupled from the associated actuator mechanisms) and slid out. It may then be replaced by another instrument or guide tube. In addition to the mechanical interface there is an electronic interface between each transmission mechanism and actuator mechanism. This electronic interface allows data (e.g., instrument/guide tube type) to be transferred. Examples of the mechanical and electrical interfaces for the various instruments, guide tubes, and imaging systems, and also about sterile draping to preserve the sterile field, are discussed in U.S. Pat. No. 6,866,671 (filed Aug. 13, 2001; Tierney et al.) and U.S. Pat. No. 6,132,368 (filed Nov. 21, 1997; Cooper), both of which are incorporated by reference herein.

Surgical instruments alone or assemblies including guide tubes, multiple instruments, and/or multiple guide tubes, and instruments coupled to actuator assemblies via various configurations (e.g., on a proximal face or a distal face of the instrument/actuator assembly), are applicable in the present disclosure. Therefore, various surgical instruments may be utilized, each surgical instrument working independently of the other and each having an end effector with at least six actively controlled DOFs in Cartesian space (i.e., surge, heave, sway, roll, pitch, yaw), via a single entry port in a patient.

The instrument shafts forming the end of these kinematic chains described above may be guided through cannulas and/or entry guides for insertion into a patient, as further described below. Examples of applicable accessory clamps and accessories, such as cannulas, are disclosed in pending U.S. application Ser. No. 11/240,087, filed Sep. 30, 2005, the full disclosure of which is incorporated by reference herein for all purposes.

Sterile Drape

Embodiments of the sterile drape will now be described in greater detail. Referring back to FIGS. 1A-1B and 2A-2C, sterile drape 1000 and 2000 are shown covering a portion of the arm assembly 101 and 201, respectively, to shield non-sterile parts of the manipulator arm from the sterile field, and also to shield the arm and its various parts from materials from the surgical procedure (e.g., body fluids, etc.). In one embodiment, the sterile drape includes a drape pocket configured to receive an instrument manipulator of an instrument manipulator assembly. The drape pocket includes an exterior surface adjacent the sterile field, and an interior surface adjacent the non-sterile instrument manipulator. The drape further includes a flexible membrane at a distal end of the drape pocket for interfacing between an output of the instrument manipulator (e.g., the interface that transmits an actuating force to the associated instrument) and an input of the surgical instrument (e.g., the interface that receives the actuating force from the associated instrument), and a rotatable seal operably coupled to a proximal opening of the drape pocket.

In another embodiment, the sterile drape includes a plurality of drape pockets, with each drape pocket including a plurality of flexible membranes at a distal end for interfacing between outputs of a respective instrument manipulator and inputs of a respective surgical instrument that control wrist, roll, grip, and translational motions of the surgical instrument. A rotatable seal, such as a labyrinth seal, may be operably coupled to a proximal opening of the drape pockets to allow all drape pockets to rotate together as a group with reference to a more proximal portion of the drape. In one example, a first portion of the rotatable seal that includes the multiple drape pockets is coupled to the rotatable base plate of the manipulator assembly platform and a second portion of the rotatable seal is coupled to a frame of the manipulator assembly platform.

In yet another embodiment, a method of draping the manipulator arm of a robotic surgical system includes first positioning a distal end of a sterile drape at the distal ends of the instrument manipulators, and then draping each instrument manipulator with a drape pocket from the distal end of the instrument manipulator to a proximal end of the instrument manipulator. The rotatable seal of the sterile drape is then coupled to a frame and a rotatable base plate of the manipulator assembly platform. The remaining parts of the manipulator arm may then be draped as desired from a distal end of the manipulator arm to a proximal end of the manipulator arm. In this example, the manipulator arm is draped from instrument manipulators to the yaw joint.

Advantageously, the configuration and geometry of the manipulator arm and instrument manipulators with a sterile drape provide for a large range of motion allowing for multi-quadrant surgery through a single port (i.e., surgical access in all patient quadrants from the single entry port), increased space around the patient and the entry port, and increased patient safety, while also providing for a robust instrument/manipulator interface, ease of instrument exchange, and maintenance of a sterile environment, as described above.

Referring back to FIG. 10, the actuator outputs of the instrument manipulator 542 engage with the actuator inputs of the instrument 960 through sterile drape 1000 or 2000. As noted above, in one embodiment, when latch 542g is actuated, the inner frame of the instrument manipulator 542 moves toward the instrument 960 a set distance and spring-loaded module outputs 542b-542e engage instrument inputs 962b-962e through drape 1000 or 2000. The independent actuator drive modules 542b', 542c', 542d', and 542e' in the instrument manipulator 542 provide actuator outputs 542b, 542c, 542d, and 542e, respectively, that engage instrument inputs 962b, 962c, 962d, and 962e, respectively, through the sterile drape upon actuating latch mechanism 542g, as described above.

Figure 11A:
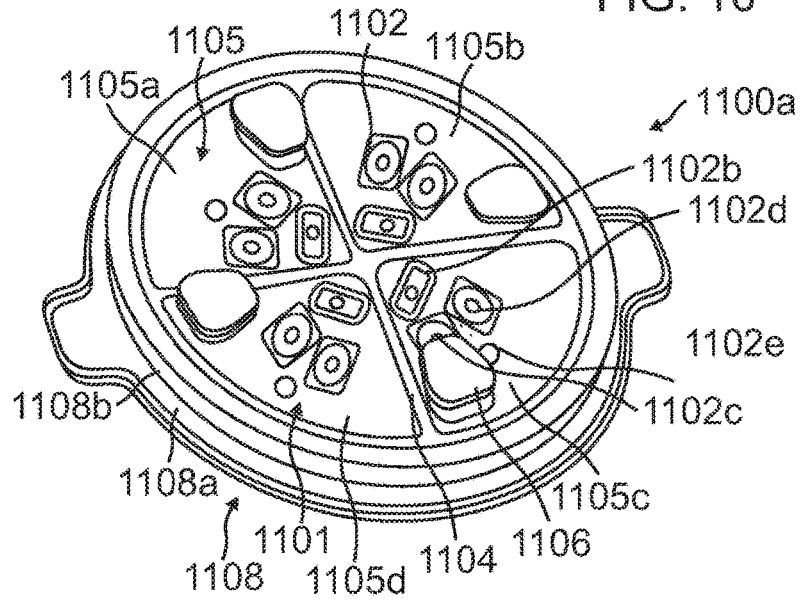
FIGS. 11A-11B illustrate perspective views of a portion of a sterile drape in a retracted state and an extended state, respectively, in accordance with an embodiment of the present disclosure.
Figure 11B:
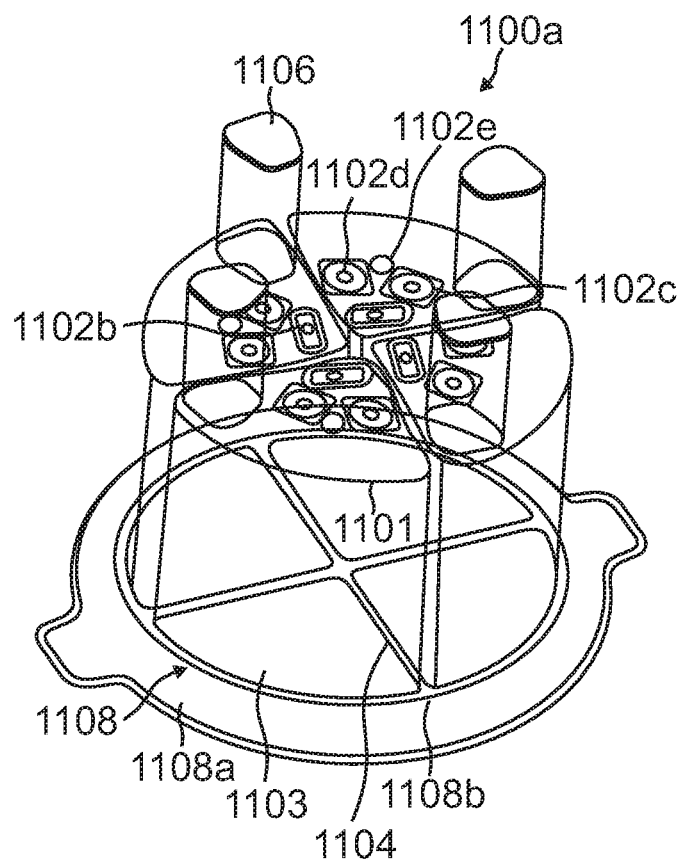
Figure 11C:
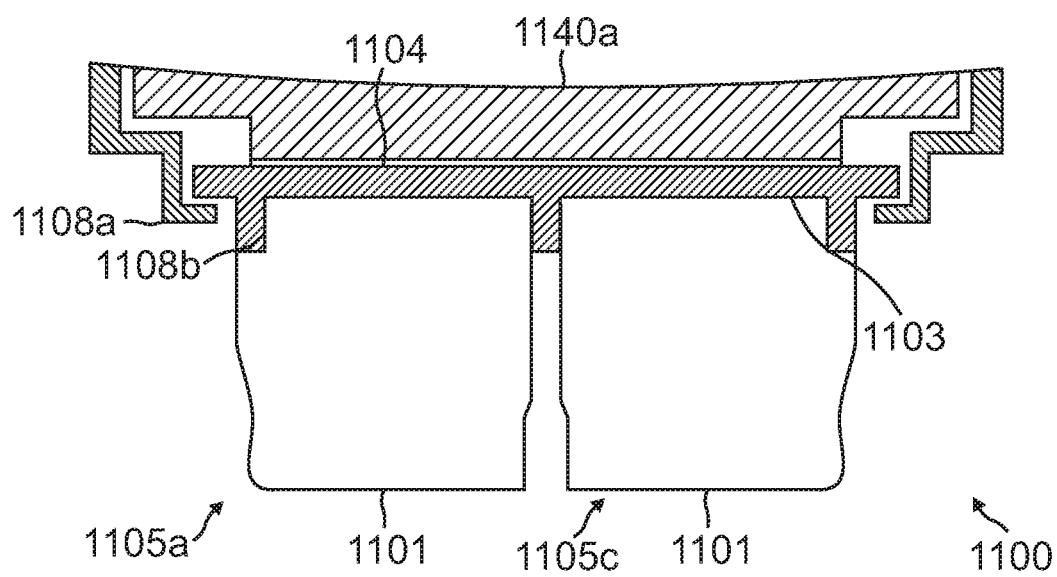
FIG. 11C illustrates a sectional view of a rotating sterile drape portion mounted to a distal end of a manipulator arm including a base platform in accordance with an embodiment of the present disclosure.

Referring now to FIGS. 11A-11D in conjunction with FIG. 10, FIGS. 11A-11B illustrate perspective views of a first drape portion 1100a of a sterile drape 1100 (FIG. 11D) in a retracted state and an extended state, respectively, and FIG. 11C illustrates a sectional view of drape portion 1100a mounted to a distal end of a rotatable base plate 1140a of a manipulator platform in accordance with an embodiment of the present disclosure. Descriptions of sterile drapes 1000 and 2000 above are applicable with respect to sterile drape 1100. For example, sterile drape 1100 covers a portion of the manipulator arm assembly, and in particular the instrument manipulators, to shield non-sterile parts of the manipulator arm from the sterile field. Furthermore, drape portion 1100a includes a plurality of drape pockets 1105 (e.g., four wedge-shaped drape pockets 1105a-1105d are shown), each including an exterior surface configured to be adjacent the sterile field, and an interior surface configured to be adjacent the non-sterile instrument manipulators. Each of the drape pockets 1105 further includes a plurality of flexible membranes 1102 at a distal end 1101 of the drape pockets 1105 for interfacing between outputs of the instrument manipulators and inputs of the surgical instruments. In one example, flexible membranes 1102b, 1102c, 1102d, and 1102e interface between the instrument manipulator outputs 542b, 542c, 542d, and 542e and the instrument inputs 962b, 962c, 962d, 962e to control instrument grip, translation, wrist, and roll motions, respectively, of the surgical instrument. A flexible membrane provides a pocket extension 1106 for the telescoping insertion mechanism of each instrument manipulator (e.g., insertion mechanism 444) along which the instrument manipulator may translate.

In one aspect, a distal end of pocket extension 1106 is attached to the insertion mechanism such that the drape pocket extension 1106 moves with the insertion mechanism and remains in a compact form away from the patient to provide space and access to a surgical port. In one example, the distal end of pocket extension 1106 can be attached to the carriage link 804 of an insertion mechanism 844 (FIG. 8) by any appropriate attachment means, such as clips, tabs, Velcro strips, and the like.

A rotatable seal 1108 operably couples proximal openings 1103 of the drape pockets 1105 to the manipulator platform of the manipulator arm assembly. In one example, the rotatable seal 1108 includes a rotatable labyrinth seal having a roll cover portion 1108a and a base comb portion 1108b rotatable within and relative to the roll cover portion 1108a. In one embodiment, base comb portion 1108b includes a disc with ribs 1104 that form a plurality of wedge-shaped "frames" with apertures, each of the frames sized to circumscribe an instrument manipulator. In one embodiment, base comb portion 1108*b* includes ribs 1104 formed ninety degrees apart within the disc. Proximal ends of the drape pockets 1105 are coupled to each of the frames of the base comb portion 1108*b*. Accordingly, the ribbed base comb portion 1108*b* aids in draping individual instrument manipulators which are closely clustered on the rotatable base plate of the instrument manipulator and further aids in maintaining the orientation and arrangement of the drape pockets 1105 as the draped instrument manipulators move during a surgical procedure.

Roll cover portion 1108*a* fixedly mounts to the frame of the manipulator platform and base comb portion 1108*b* fixedly mounts to the rotatable base plate 1140*a*, such that when base plate 1140*a* is rotated, the base comb portion 1108*b* also rotates in combination with the draped instrument manipulators while roll cover portion 1108*a* is stationary being fixedly mounted to the manipulator platform frame.

FIGS. 11A and 11B illustrate the drape pockets 1105 in retracted and extended states, respectively, as the instrument manipulators retract and extend along their respective insertion axes. Although the four drape pockets 1105 are shown equally retracted and extended, the drape pockets may independently retract and extend as the instrument manipulators are independently and/or dependently controlled with respect to one another.

It is also noted that base comb portion 1108*b* may include various number of ribs oriented at angles other than ninety degrees as long as space is provided to fit an instrument manipulator through each of the frames of the base comb portion. In one example, the base comb portion 1108*b* may be comprised of ribs that divide a circular area into a multitude of segments that are each sized to enclose an instrument manipulator.

Figure 11D:
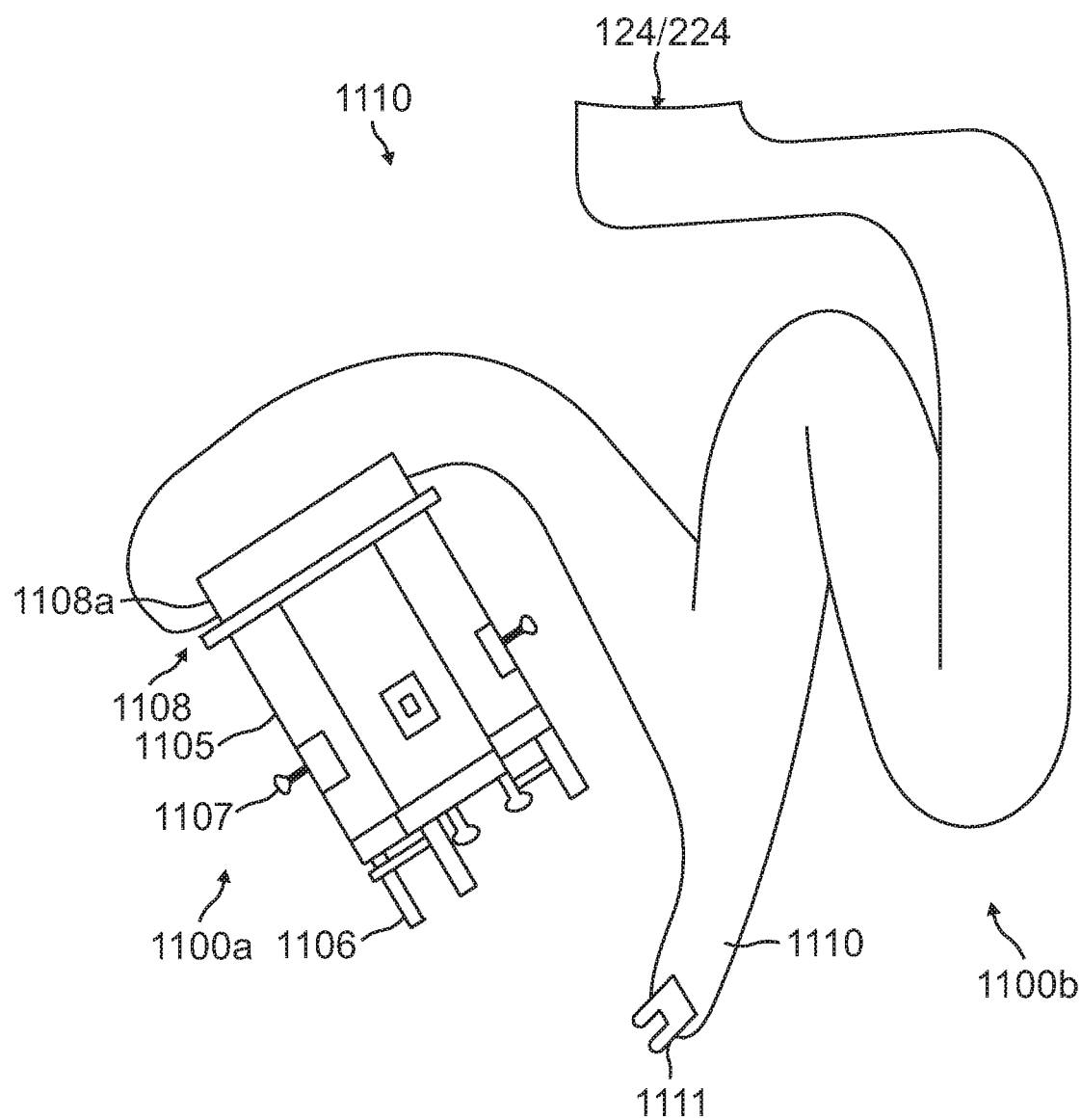
FIG. 11D illustrates an extended sterile drape in accordance with an embodiment of the present disclosure.

Sterile drape 1100 also allows for transitioning from the draping of the individual instrument manipulators to the remaining parts of the manipulator arm assembly, as shown in FIG. 11D. The drape 1100 may continue from the rotatable seal 1108 (e.g., the roll cover portion 1108*a*) to blend into a larger second drape portion 1100*b* designed to cover remaining portions (e.g., joints and links) of the manipulator arm as desired, in one example continuously covering the manipulator arm to the manipulator assembly yaw joint (e.g., yaw joint 124, 224). Accordingly, the rotatable seal 1108 allows for the instrument manipulator cluster to freely rotate relative to the rest of the manipulator arm assembly while substantially the entire arm assembly remains draped, thereby preserving the sterile environment of the surgical site.

In accordance with another embodiment, the sterile drape portion 1100*b* includes a cannula mounting arm pocket 1110 designed to drape a retractable cannula mounting arm as described in further detail below. In one embodiment, a movable cannula mount includes a base portion coupled to the manipulator arm and a retractable portion movably coupled to the base portion. The retractable portion may be moved between a retracted position and a deployed position via a rotating joint so that the rectractable portion may be rotated upwards or folded toward the base portion to create more space around the patient and/or to more easily don a drape over the cannula mount when draping the manipulator arm. Other joints may be used to couple the retractable portion and the base portion, including but not limited to a ball and socket joint or a universal joint, a sliding joint to create a telescoping effect, and the like, so that the retractable portion may be moved closer to the base portion in order to reduce the overall form factor of the cannula mount.

In another embodiment, the entire cannula mount may be internally telescoping relative to the manipulator arm. Accordingly, the movable cannula mounting arm allows for the draping of a larger robot arm with a relatively smaller opening in the drape. The drape may be positioned over the retracted cannula mounting arm and then after being draped within pocket 1110, the cannula mounting arm may be extended into an operating position. According to one aspect, the cannula mounting arm is fixed in the operating position during operation of an instrument.

In one instance, drape pocket 1110 may include a reinforced drape section 1111 that fits over a clamp (see, e.g., clamps 1754 in FIGS. 19A-19B and 20A-20B, and clamp 2454 and receptacle 2456 in FIGS. 24A-24D) on a distal end of the cannula mounting arm.

The drape 1100*a* may further include a latch cover 1107 on the side of individual drape pockets 1105 to cover the individual latches 1342*g* (FIGS. 14A, 15, 16A, and 17A-17C) that may extend outside the circumference of the instrument manipulator during use.

Advantageously, because of the distal face of the instrument manipulator that interfaces with an instrument, the spring-loaded and independent outputs of the instrument manipulator, and advantageous sterile drape, instruments may be easily and robustly exchanged onto the instrument manipulator while maintaining a robust sterile environment during a surgical procedure. Furthermore, the sterile drape allows for the surgical robotic system to be quickly and easily prepared while also providing for improved range of motion (e.g., rotational motion) with a small form factor, thereby reducing operating room preparation time and costs.

Sterile Adapter

Figure 12:
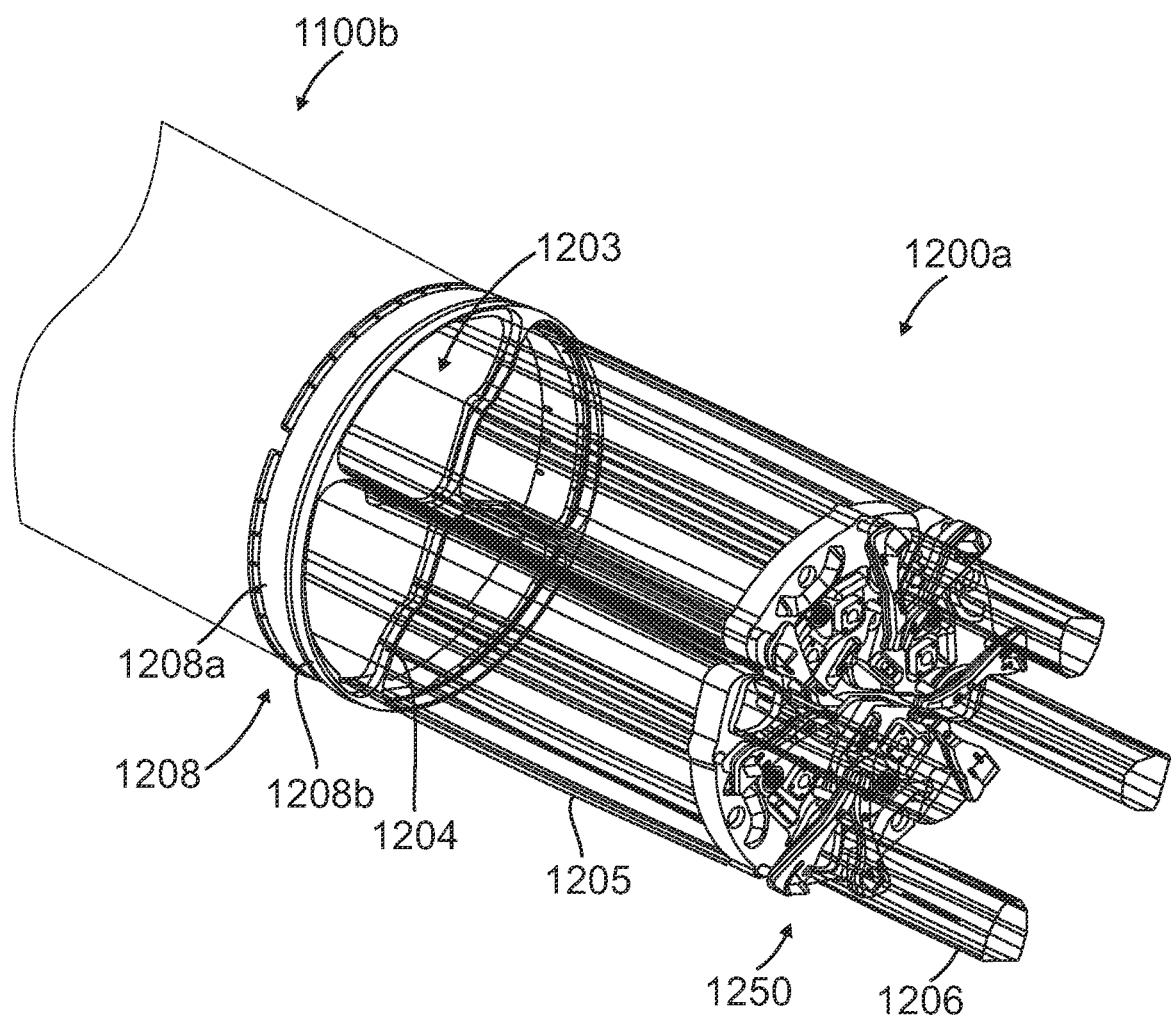
FIG. 12 illustrates a perspective view of a portion of an extended sterile drape including a sterile adapter in accordance with an embodiment of the present disclosure.

Another embodiment of a drape including a sterile adapter will now be described in greater detail. FIG. 12 illustrates a perspective view of a drape portion 1200*a* of an extended sterile drape including a sterile adapter 1250 in accordance with another embodiment of the present disclosure. Drape portion 1200*a* may replace drape portion 1100*a* in FIG. 11D, and is operably coupled to drape portion 1100*b* by way of a rotatable seal 1208 which is substantially similar to rotatable seal 1108. Drape portion 1200*a* includes a plurality of drape sleeves 1205 coupled between rotatable seal 1208 and sterile adapter 1250. Drape portion 1200*a* further includes pocket extensions 1206 coupled to the sterile adapter 1250 for draping over insertion mechanisms of the instrument manipulators.

Rotatable seal 1208 operably couples proximal openings 1203 of the drape sleeves 1205 to the manipulator platform of the manipulator arm assembly. In one example, the rotatable seal 1208 includes a rotatable labyrinth seal having a roll cover portion 1208*a* and a base comb portion 1208*b* rotatable relative to the roll cover portion 1208*a*. In one embodiment, base comb portion 1208*b* includes a disc with ribs 1204 that form a plurality of wedge-shaped "frames" with apertures, each of the frames sized to circumscribe an instrument manipulator. In one embodiment, base comb portion 1208*b* includes ribs 1204 formed ninety degrees apart within the disc. Proximal ends of the drape sleeves 1205 are coupled to each of the frames of the base comb portion 1208*b*. Accordingly, the ribbed base comb portion 1208*b* aids in draping individual instrument manipulators which are closely clustered on the rotatable base plate of the instrument manipulator and further aids in maintaining the orientation and arrangement of the drape sleeves 1205 as the draped instrument manipulators move during a surgical procedure.

Although FIG. 12 illustrates all the drape sleeves 1205 in extended states, for example as the instrument manipulators extend along their respective insertion mechanisms, it is noted that the drape sleeves may independently retract and extend as the instrument manipulators are independently and/or dependently controlled with respect to one another.

It is also noted that base comb portion 1208b may include various number of ribs oriented at angles other than ninety degrees as long as space is provided to fit an instrument manipulator through each of the frames of the base comb portion. In one example, the base comb portion 1208b may be comprised of ribs that divide a circular area into a multitude of segments that are sized to each enclose an instrument manipulator.

Roll cover portion 1208a fixedly mounts to the frame of the manipulator platform (e.g., the manipulator halo) and base comb portion 1208b fixedly mounts to the rotatable base plate 1140a, such that when base plate 1140a is rotated, the base comb portion 1208b also rotates in combination with the draped instrument manipulators. In one example, since the proximal end of dr_ape sleeves 1205 are coupled to base comb portion 1208b, all the drape sleeves 1205 rotate together as a group with reference to a more proximal drape portion 1100b.

Figure 13A:
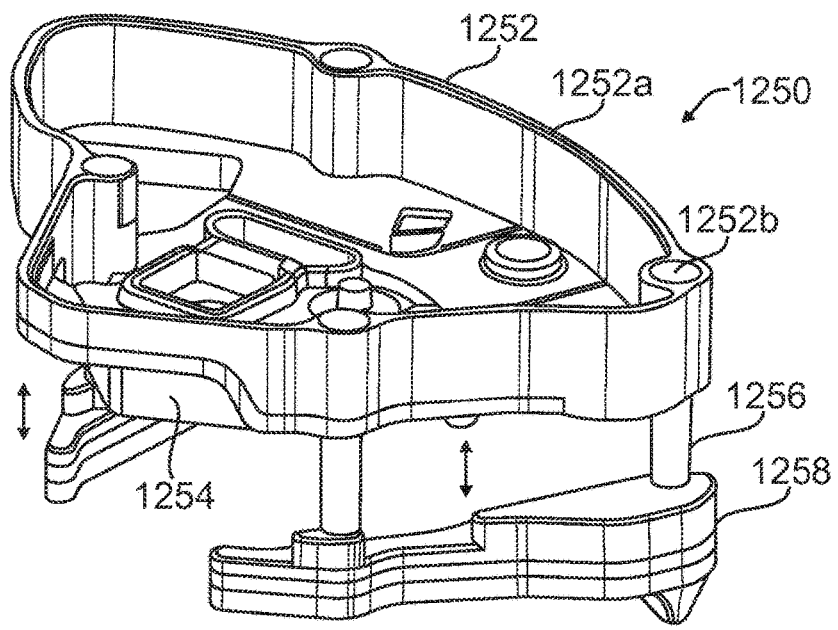
FIGS. 13A and 13B illustrate a perspective view of an assembled sterile adapter and an exploded view of the sterile adapter, respectively, in accordance with an embodiment of the present disclosure.
Figure 13C:
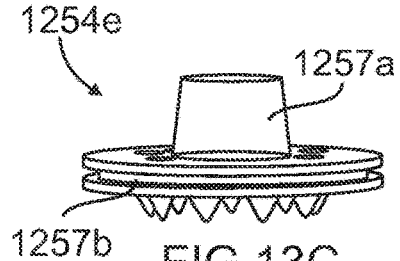
FIG. 13C illustrates an enlarged view of a roll actuator interface in accordance with an embodiment of the present disclosure.
Figure 13B:
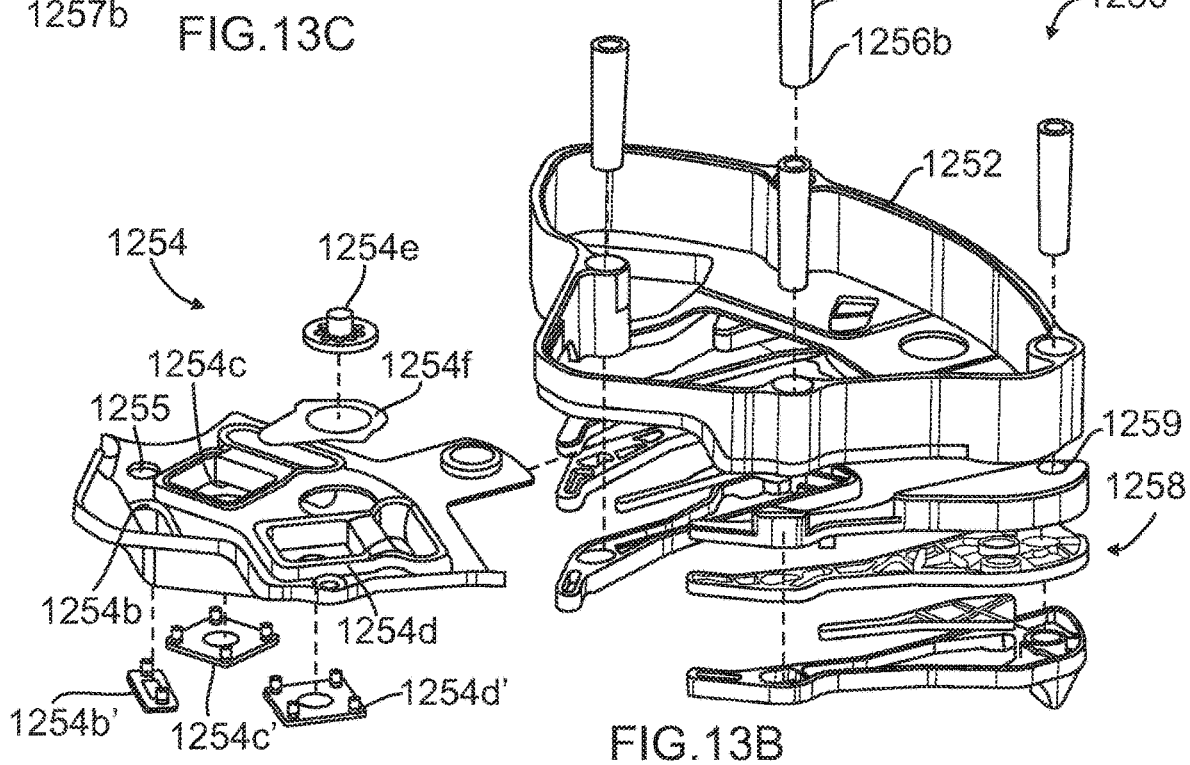

FIGS. 13A and 13B illustrate a perspective view of an assembled sterile adapter 1250 and an exploded view of the sterile adapter 1250, respectively, in accordance with an embodiment of the present disclosure. Sterile adapter 1250 includes a boot 1252 having a boot wall 1252a and cylindrical apertures 1252b that serve as passageways for posts on the instrument manipulator as will be further described below. A distal end of drape sleeves 1205 may be coupled to an exterior surface of boot wall 1252a. Adapter 1250 further includes a pair of supports 1258 that serve to properly align, position, and retain a surgical instrument on an underside of the sterile adapter for engagement with the instrument manipulator on a top surface of the sterile adapter. Adapter 1250 further includes a flexible membrane interface 1254 that interfaces between outputs of a respective instrument manipulator and inputs of a respective surgical instrument for controlling wrist, roll, grip, and translational motions of the surgical instrument. In one embodiment, membrane interface 1254 includes a grip actuator interface 1254b, a joggle actuator interface 1254c, a wrist actuator interface 1254d, and a roll actuator interface 1254e for interfacing with associated instrument manipulator outputs.

In one embodiment, roll actuator interface 1254e is designed to rotate and maintain a sterile barrier within the sterile adapter 1250. As illustrated in FIG. 13C, in one aspect, the roll actuator interface 1254e includes a roll disc 1257a having a slot or groove 1257b around the circumference of the disc that accepts a flat retaining plate 1254f (FIG. 13B). The retaining plate 1254f is attached to the flexible membrane interface 1254 and allows the roll disc to rotate while maintaining a sterile barrier for the sterile adapter and drape.

Membrane interface 1254 is positioned between boot 1252 and supports 1258, and tubes 1256 couple boot 1252, membrane interface 1254, and supports 1258 together. Tubes 1256 are aligned with boot apertures 1252b and membrane apertures 1254b and a shaft portion of tubes 1256 are positioned within the apertures. A tube lip 1256a is retained within boot aperture 1252b and a tube end 1256 is fixedly coupled to support 1258 such that tubes 1256 and therefore supports 1258 are movable a certain lengthwise distance of the tube shaft, as shown by the double sided arrows in FIG. 13A.

Optionally, a grip actuator interface plate 1254b', a joggle actuator interface plate 1254c', and a wrist actuator interface plate 1254d' may be coupled to an underside of the grip actuator interface 1254b, the joggle actuator interface 1254c, and the wrist actuator interface 1254d, respectively, for increased engagement and coupling with associated instrument inputs.

Figure 14A:
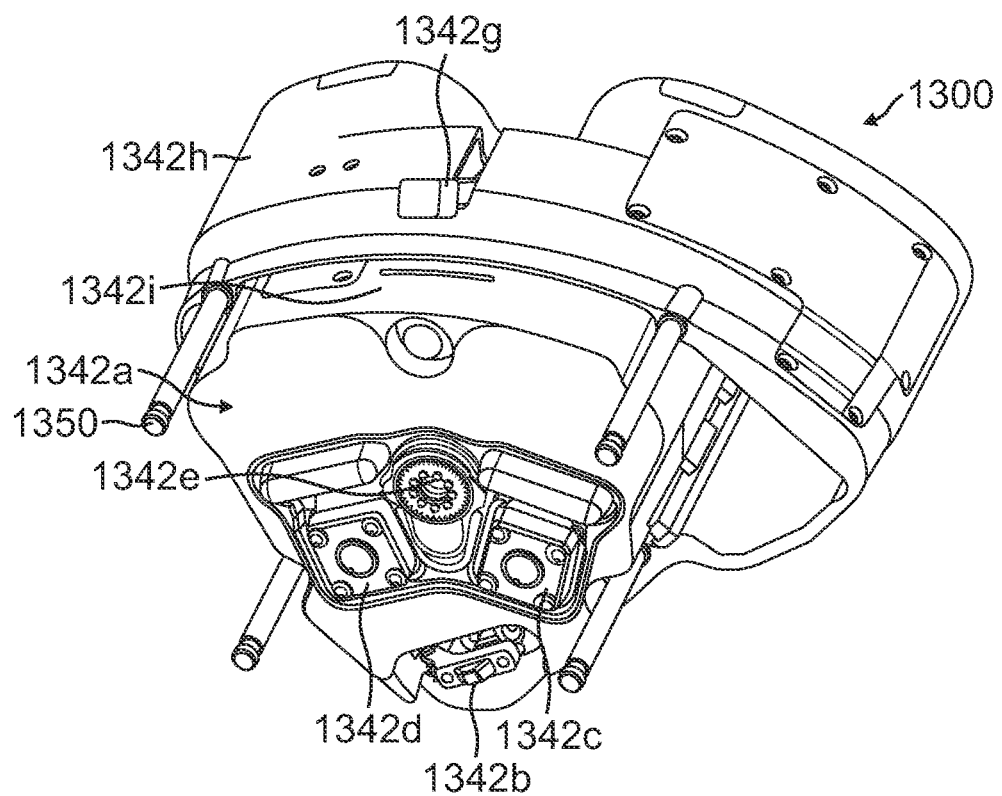
FIGS. 14A and 14B illustrate a bottom perspective view and a bottom view of an instrument manipulator in accordance with an embodiment of the present disclosure.
Figure 14B:
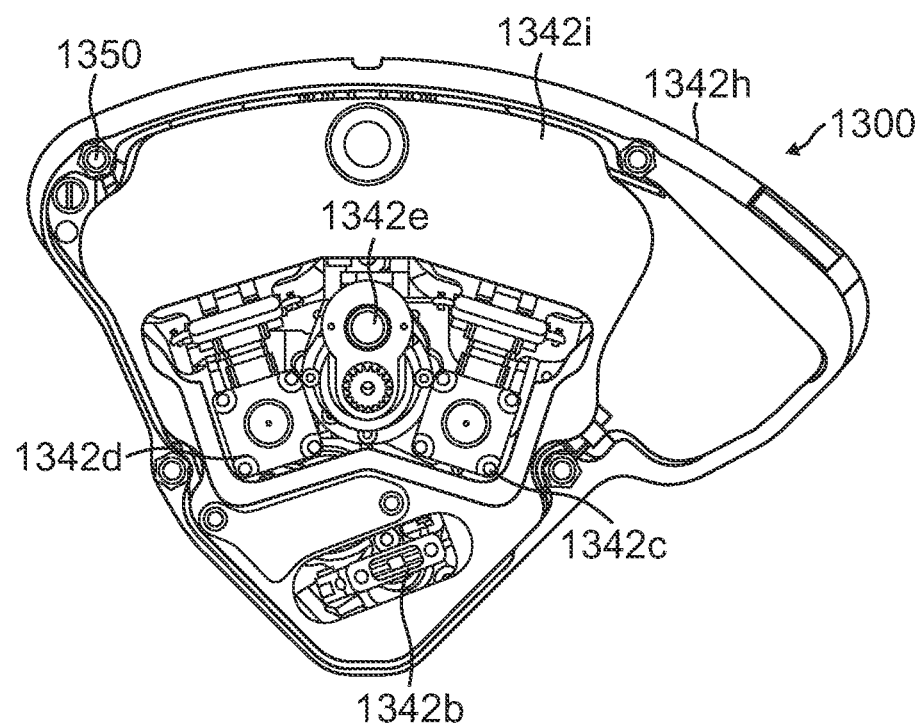

FIGS. 14A and 14B illustrate a bottom perspective view and a bottom view of an instrument manipulator 1300 in accordance with an embodiment of the present disclosure. In this illustrative embodiment, instruments mount against the distal face 1342a of the instrument manipulator 1300. Distal face 1342a includes various actuation outputs that transfer actuation forces to a mounted instrument, similar to the instrument manipulators described above with respect to FIGS. 3-8. As shown in FIGS. 14A and 14B, such actuation outputs may include a grip output lever 1342b (controlling the grip motion of an instrument end effector), a joggle output gimbal 1342c (controlling the side-to-side motion and the up-and-down motion of a distal end parallel linkage ("joggle" or "elbow" mechanism)), a wrist output gimbal 1342d (controlling the yaw motion and the pitch motion of an instrument end effector), and a roll output disk 1342e (controlling the roll motion of an instrument). Independent actuator drive modules (similar to those described above with respect to modules 542b', 542c', 542d', and 542e') in the instrument manipulator 1300 provide the actuator outputs 1342b, 1342c, 1342d, and 1342e. In a similar manner, the actuator outputs 1342b-1342e may be spring-loaded. Details of applicable outputs, and the associated parts of the instrument force transmission mechanism that receives such outputs, may be found in U.S. patent application Ser. No. 12/060,104 (filed Mar. 31, 2008; U.S. Patent Application Pub. No. US 2009/0248040 A1), which is incorporated herein by reference. Examples of the proximal ends of illustrative surgical instruments that may receive such inputs may be found in U.S. patent application Ser. No. 11/762,165, which is referenced above. Briefly, the side-to-side and up-and-down DOFs are provided by a distal end parallel linkage, the end effector yaw and end effector pitch DOFs are provided by a distal flexible wrist mechanism, the instrument roll DOF is provided by rolling the instrument shaft while keeping the end effector at an essentially constant position and pitch/yaw orientation, and the instrument grip DOF is provided by two movable opposing end effector jaws. Such DOFs are illustrative of more or fewer DOFs (e.g., in some implementations a camera instrument omits instrument roll and grip DOFs).

Instrument manipulator 1300 further includes a latch mechanism 1342g for engaging the actuator outputs of the instrument manipulator 1300 with the actuator inputs of a mounted instrument through sterile adapter 1250. In one embodiment, similar to the latch mechanism described above, when latch 1342g is actuated, the inner frame 1342i of the instrument manipulator 1300 moves a set distance relative to outer shell 1342h and towards a mounted instrument. Spring-loaded module outputs 1342b-1342e engage appropriate instrument inputs through the sterile adapter 1250, and in one example through the membrane interface 1254. A mounted instrument is thus clamped between the upper surface of supports 1258 and the spring loaded outputs through the membrane interface of the sterile adapter.

As noted above, the drape 1100a may include a latch cover 1107 (FIG. 11D) on the individual drape pockets 1105 to cover the individual latches 1342g that may extend outside the circumference of the instrument manipulator during use. The latch handles are each able to fold inside the circumference of a corresponding instrument manipulator to enable the rotatable seal of a drape to pass over the instrument manipulators.

Instrument manipulator 1300 further includes posts 1350 for operably coupling the instrument manipulator 1300 to the sterile adapter 1250 as will be further described below.

Figure 15:
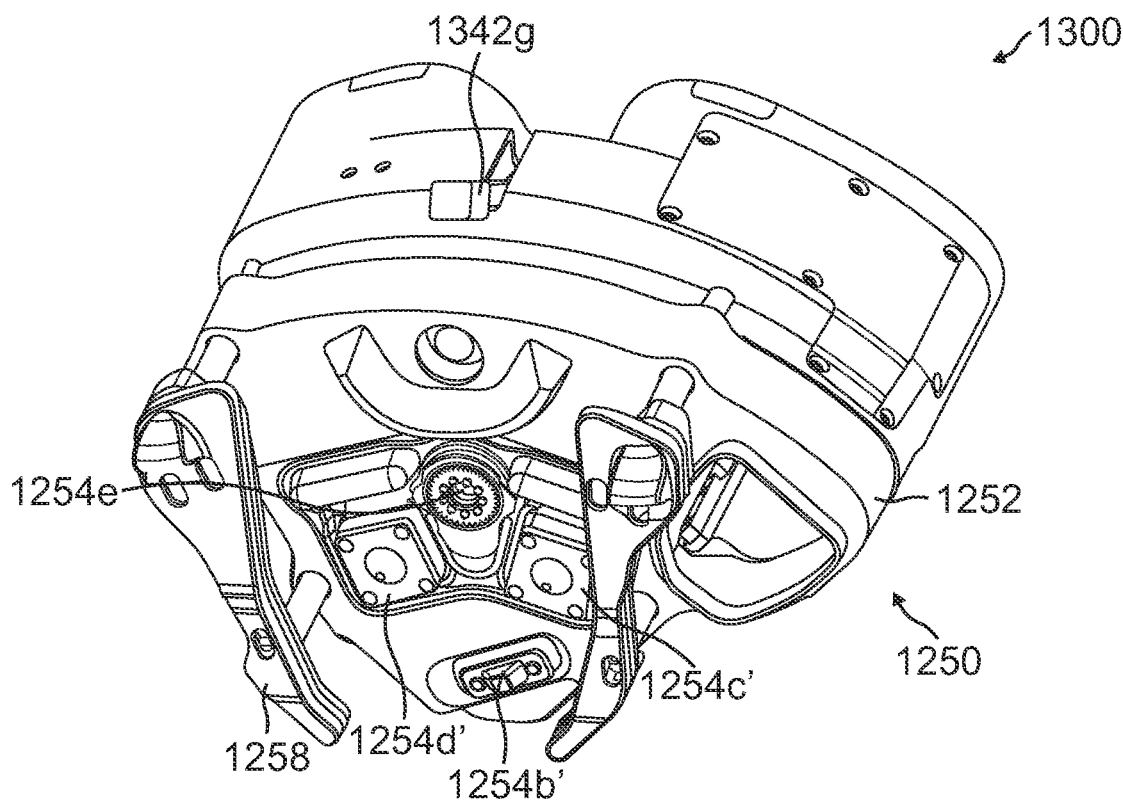
FIG. 15 illustrates a bottom perspective view of the instrument manipulator operably coupled to the sterile adapter in accordance with an embodiment of the present disclosure.
Figure 16A:
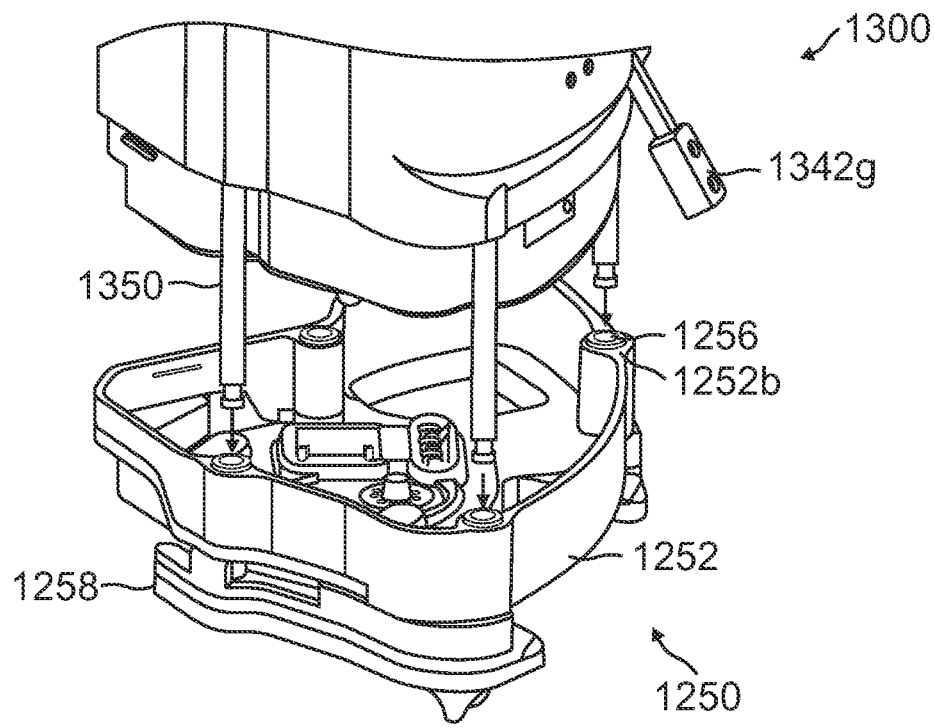
FIGS. 16A-16E illustrate a sequence for coupling the instrument manipulator and the sterile adapter in accordance with an embodiment of the present disclosure.
Figure 16B:
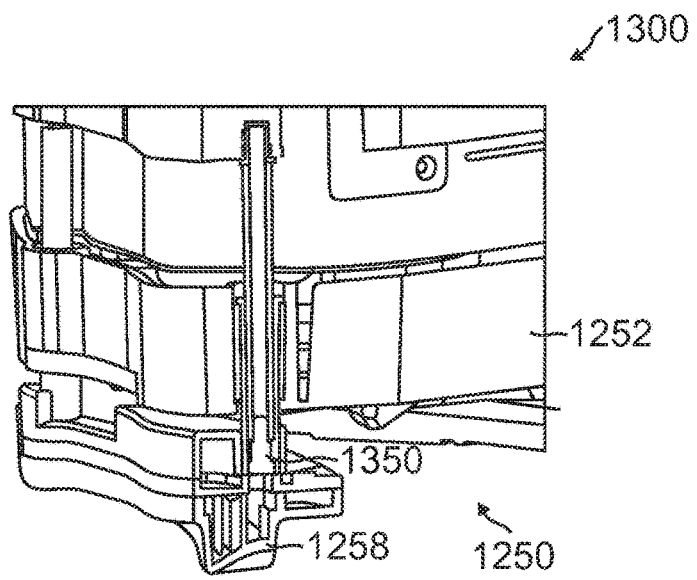
Figures 1, 16C:
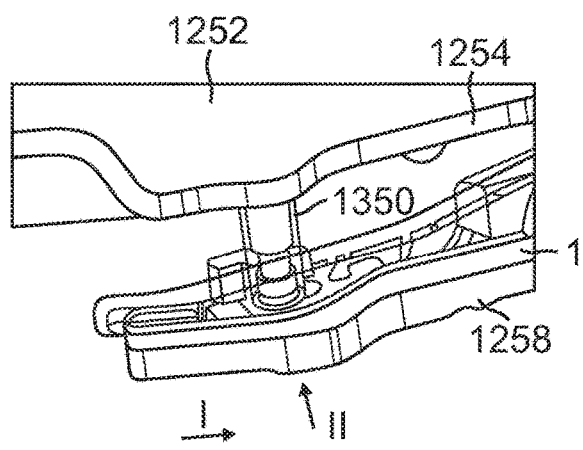
Figure 16D:
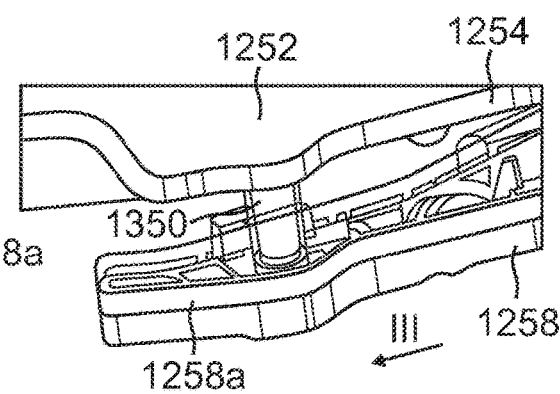
Figures 2, 16C:
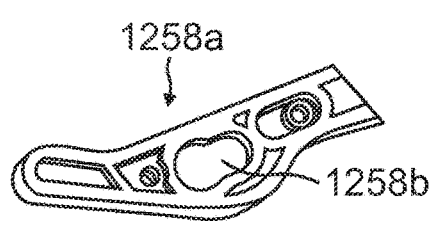
Figure 16E:
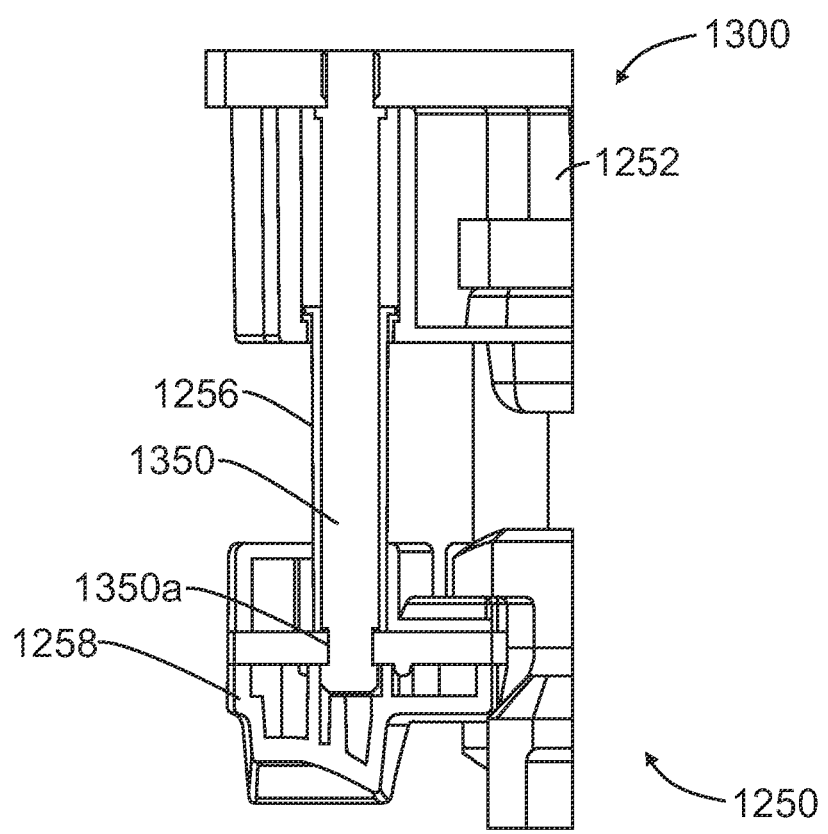

Referring now to FIGS. 15 and 16A-16E, the coupling of the instrument manipulator 1300 to the sterile adapter 1250 is illustrated and described. FIG. 15 illustrates a bottom perspective view of the instrument manipulator 1300 operably coupled to the sterile adapter 1250 in accordance with an embodiment of the present disclosure. FIGS. 16A-16E illustrate a sequence for coupling the instrument manipulator 1300 and the sterile adapter 1250 in accordance with an embodiment of the present disclosure. As shown in FIG. 16A, posts 1350 are aligned with tubes 1256 within boot apertures 1252*b*. Then, as shown in FIG. 16B, the free end of posts 1350 are positioned through tube 1256 until tabs at the end of posts 1350 engage with associated support apertures, as shown in FIG. 16E. Thus, one end of posts 1350 are fixedly mounted to the supports 1258. In one embodiment, supports 1258 include a slide 1258*a* having a keyhole aperture 1258*b*, as illustrated in FIGS. 16C-1 and 16C-2. Support 1258 is slid in a direction of arrow Ito allow the post 1350 to pass to the end of the keyhole aperture 1258*b*, as the sterile adapter is lifted into a final position as shown by arrow II. Then support 1258 is returned in a direction of arrow III by a biasing means such that the narrow section of the keyhole aperture 1258*b* locks into a groove 1350*a* in the post 1350 (FIG. 16E).

After the supports 1258 of the sterile adapter have been attached to the posts on the instrument manipulator housing, the boot 1252 of the sterile adapter 1250 is attached to the distal face 1342*a* of the instrument manipulator 1300. In one embodiment, this attachment is accomplished by protrusions on the inside walls of the boot that register in depressions on the sides of the inner frame 1342*i* of the instrument manipulator. Such an attachment allows the boot to stay attached to the inner frame as the inner frame is raised or lowered by the latch 1342*g*.

Figure 17A:
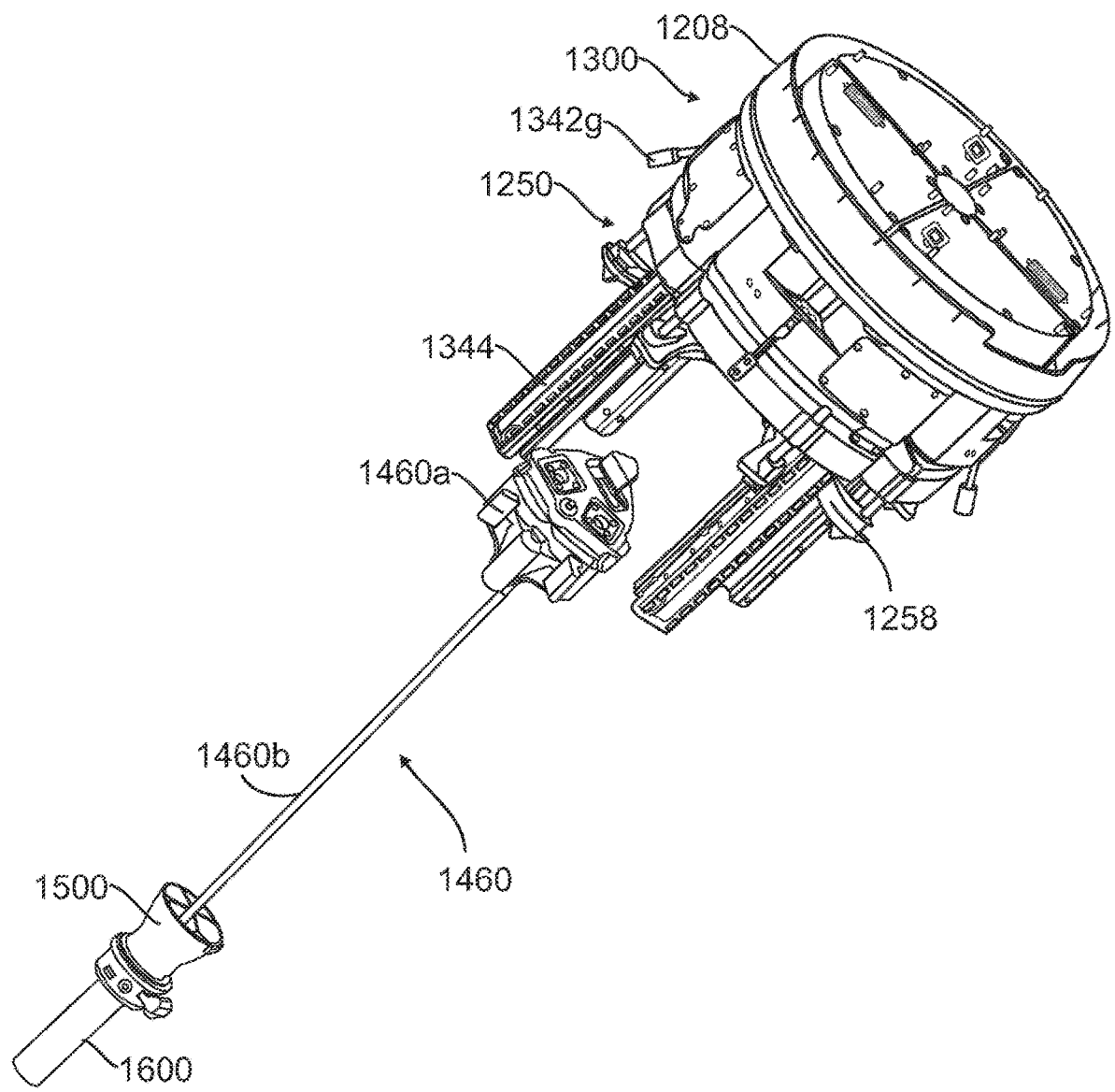
FIGS. 17A-17O illustrate a sequence for coupling a surgical instrument to the sterile adapter in accordance with an embodiment of the present disclosure.
Figure 17B:
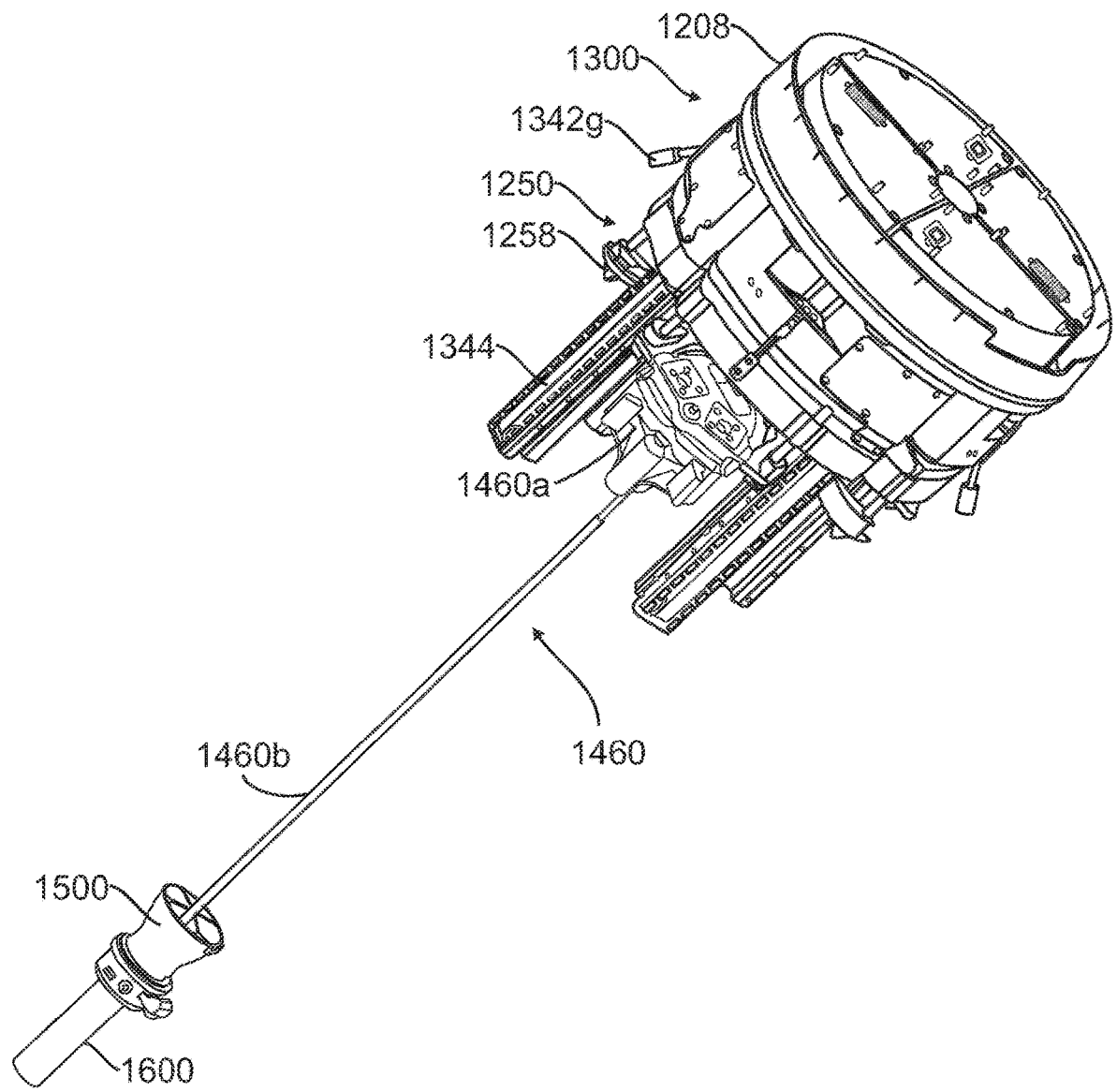
Figure 17C:
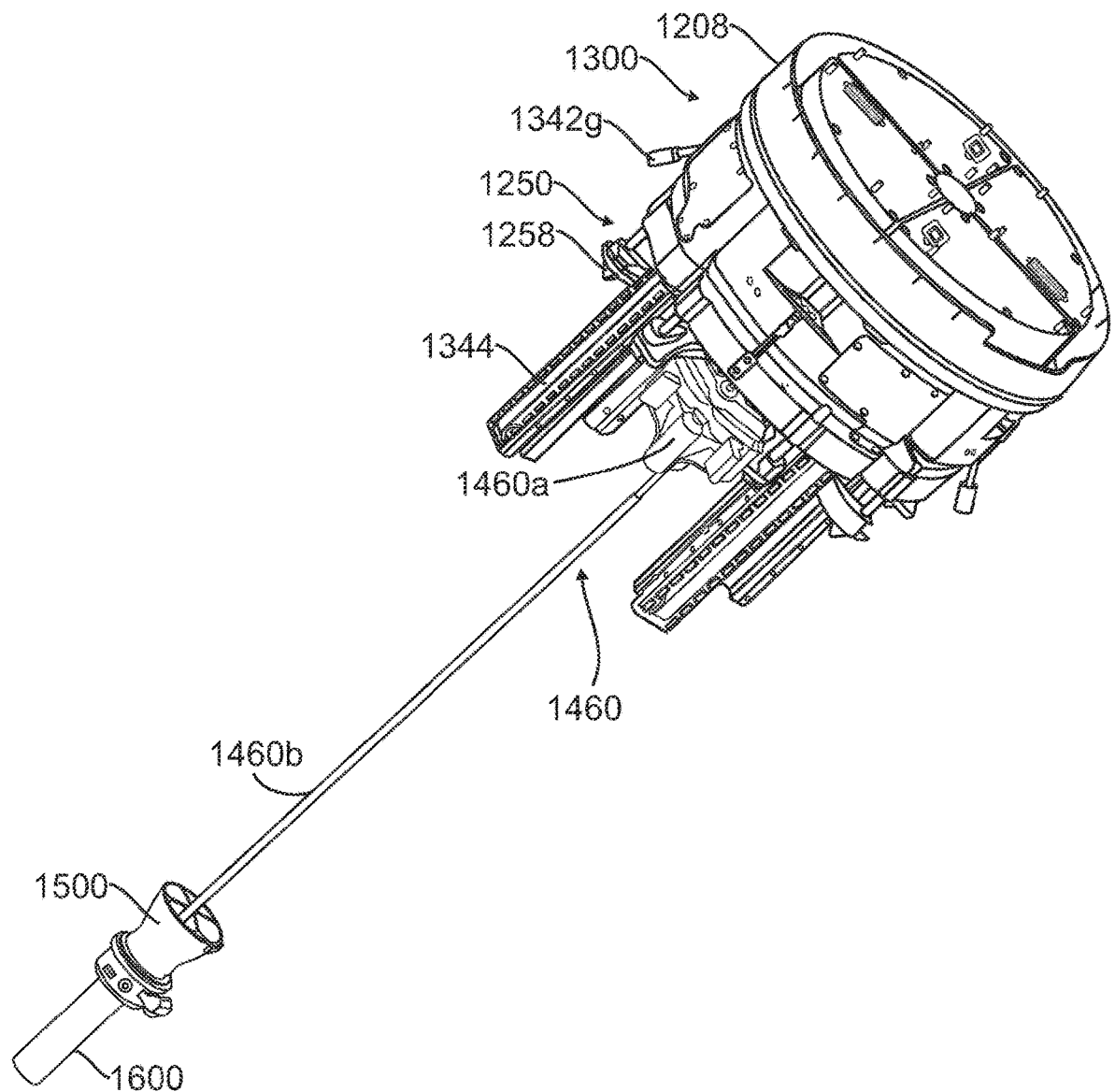

Referring now to FIGS. 17A-17C and 18A-18B, the coupling of a surgical instrument 1460 to the sterile adapter 1250 is illustrated and described. FIGS. 17A-170 illustrate a sequence for coupling the surgical instrument 1460 to the sterile adapter 1250 in accordance with an embodiment of the present disclosure. As shown in FIG. 17A, the instrument 1460 includes a force transmission mechanism 1460*a* and a shaft 1460*b*. A tip of shaft 1460*b* is placed within an entry guide 1500, which is freely rotatable within a cannula 1600. FIG. 17B shows tabs (e.g., tabs 1462 of FIG. 18A) on the force transmission mechanism 1460*a* of instrument 1460 engaged with and aligned by a pair of supports 1258, and FIG. 17C shows force transmission mechanism 1460*a* being further translated along a top surface of supports 1258.

Figure 18A:
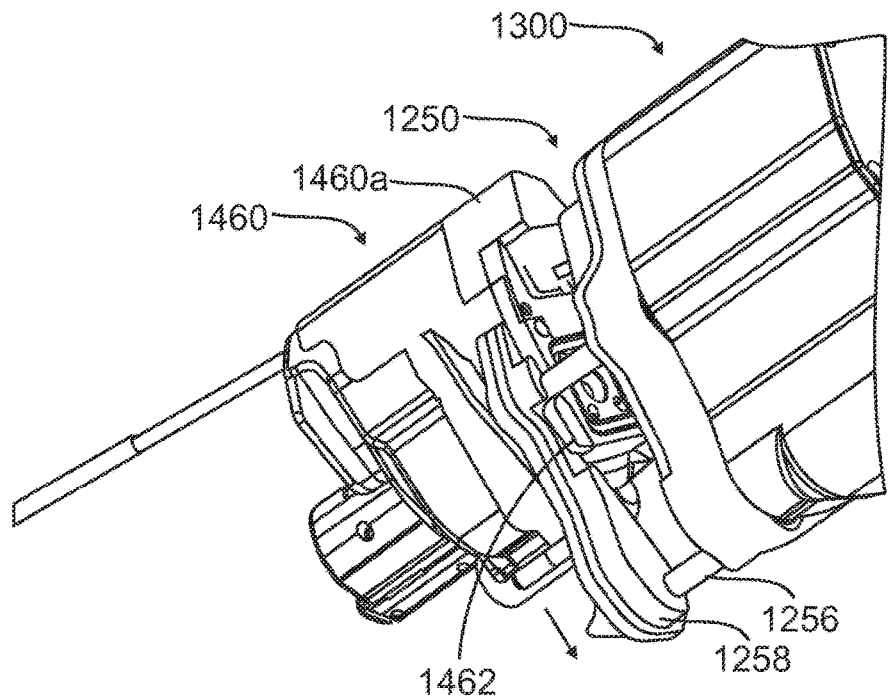
FIGS. 18A and 18B illustrate an enlarged perspective view and side view, respectively, of the instrument and sterile adapter prior to engagement.
Figure 18B:
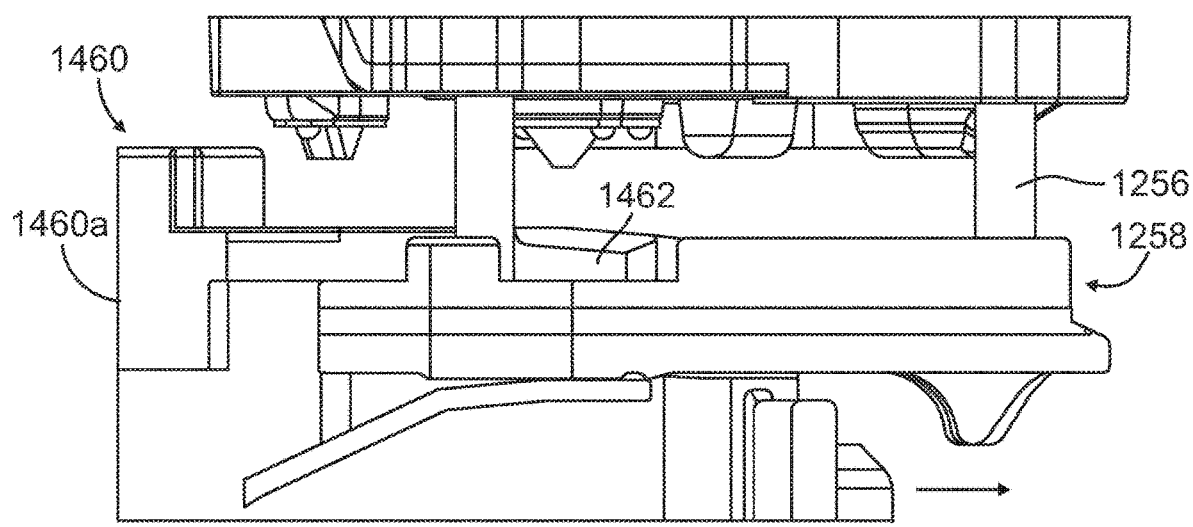

FIGS. 18A and 18B illustrate an enlarged perspective view and side view, respectively, of the instrument 1460 and sterile adapter 1250 prior to full translation of the force transmission mechanism 1460*a* along supports 1258. Instrument 1460 is translated along supports 1258 until a retention mechanism is reached along the supports, which in one example can be a protrusion on an underside of tab 1462 that aligns and couples with an aperture on a top surface of support 1258. Latch 1342*g* may then be actuated to engage the instrument manipulator outputs with the instrument inputs through sterile adapter 1250. In one embodiment, supports 1258 are prevented from being removed from posts 1350 after an instrument has been mounted. In one aspect, a protrusion on the support may engage with a depression on the side of the instrument force transmission mechanism housing to prevent the support from moving while the instrument has been mounted.

Entry Guide

Embodiments of an entry guide, cannula, and cannula mounting arm will now be described in greater detail. As previously described, a surgical instrument is mounted on and actuated by each surgical instrument manipulator. The instruments are removably mounted so that various instruments may be interchangeably mounted on a particular manipulator. In one aspect, one or more manipulators may be configured to support and actuate a particular type of instrument, such as a camera instrument. The shafts of the instruments extend distally from the instrument manipulators. The shafts extend through a common cannula placed at the entry port into the patient (e.g., through the body wall, at a natural orifice). The cannula is coupled to a cannula mounting arm which is movably coupled to a manipulator arm. In one aspect, an entry guide is positioned at least partially within the cannula, and each instrument shaft extends through a channel in the entry guide, so as to provide additional support for the instrument shafts.

Figure 19A:
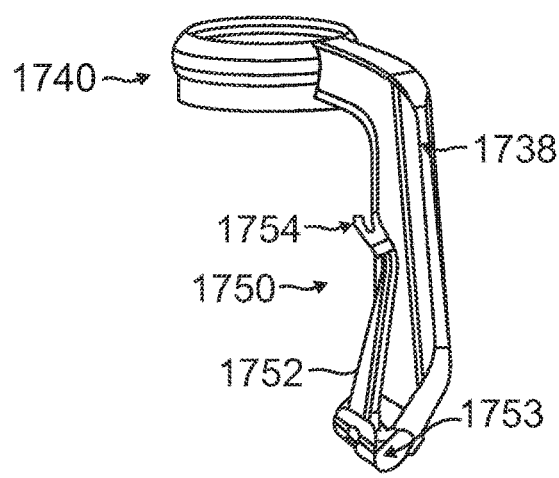
FIGS. 19A and 19B illustrate perspective views of a movable cannula mount in a retracted position and a deployed position, respectively.
Figure 19B:
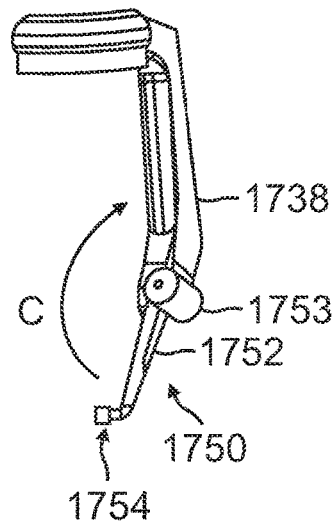

FIGS. 19A and 19B illustrate perspective views of an embodiment of a movable and/or detachable cannula mount 1750 in a retracted position and a deployed position, respectively. Cannula mount 1750 includes an extension 1752 that is movably coupled to a link 1738 of the manipulator arm, such as adjacent a proximal end of fourth manipulator link 138 (FIGS. 1A and 1B). Cannula mount 1750 further includes a clamp 1754 on a distal end of extension 1752. In one implementation, extension 1752 is coupled to link 1738 by a rotational joint 1753 that allows extension 1752 to move between a stowed position adjacent link 1738 and an operational position that holds the cannula in the correct position so that the remote center of motion is located along the cannula. In one implementation, extension 1752 may be rotated upwards or folded toward link 1738, as shown by arrow C, to create more space around the patient and/or to more easily don a drape over the cannula mount when draping the manipulator arm. Other joints may be used to couple the extension 1752, including but not limited to a ball and socket joint or a universal joint, a sliding joint to create a telescoping effect, and the like, so that the extension may be moved closer to the link in order to reduce the overall form factor of the cannula mount and manipulator arm. In another embodiment, the extension 1752 may be internally telescoping relative to the manipulator arm, or the extension 1752 may be detachable from and operably couplable to the link. During operation of the surgical system, extension 1752 is maintained in an operating position.

Figure 20A:
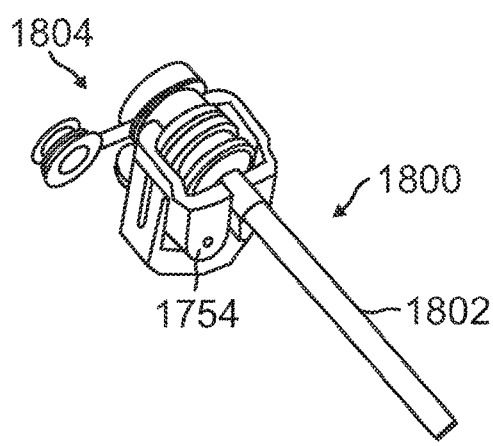
FIGS. 20A and 20B illustrate a front and a back perspective view of a cannula mounted on a cannula clamp in accordance with an embodiment.
Figure 20B:
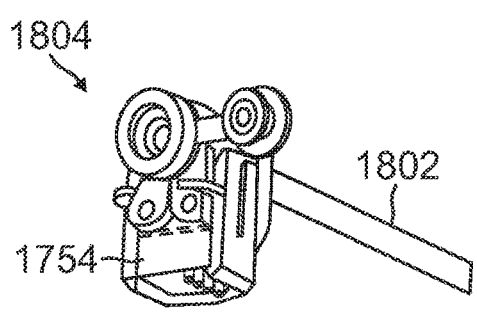
Figure 21:
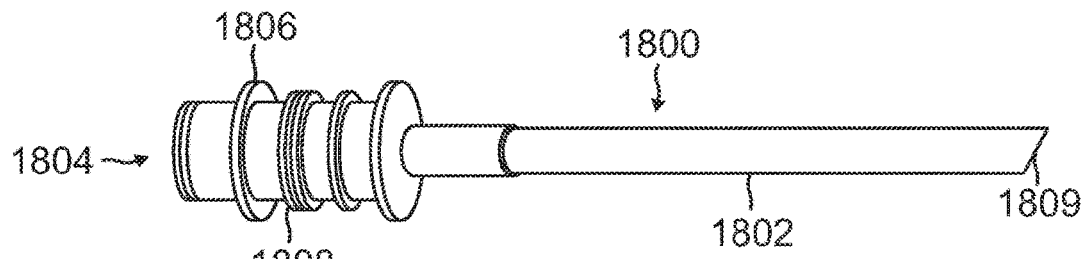
FIG. 21 illustrates a perspective view of a cannula alone.
Figure 22:
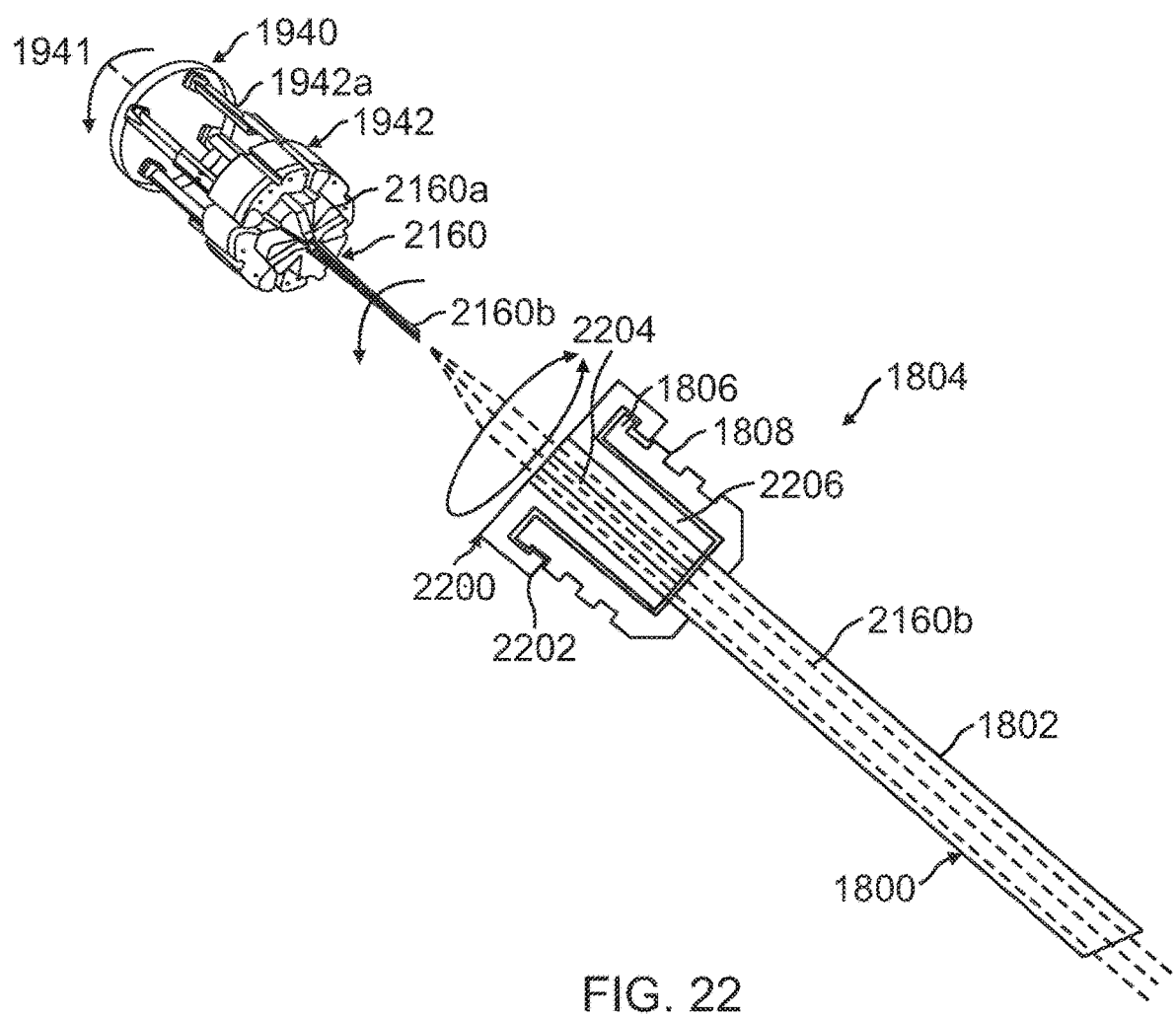
FIG. 22 illustrates a cross-sectional view of the cannula of FIG. 21 and a mounted entry guide of FIGS. 23A and 23B in combination with instruments mounted to instrument manipulators on a manipulator platform in accordance with an embodiment of the present disclosure.
Figure 23A:
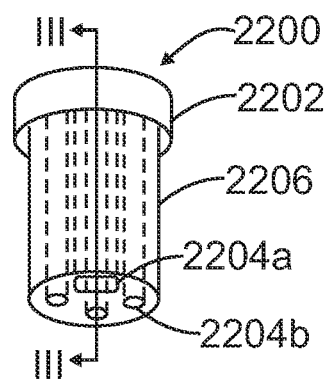
FIGS. 23A and 23B illustrate a perspective view and a top view of the entry guide of FIG. 22.
Figure 23B:
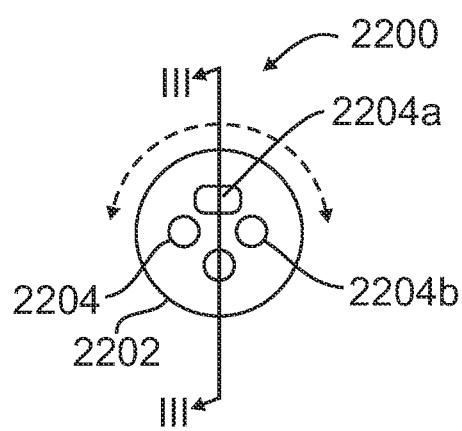

FIGS. 20A and 20B illustrate perspective views of a cannula 1800 mounted to clamp 1754 of cannula mount 1750 as illustrated in FIGS. 19A-19B, and FIG. 21 illustrates a perspective view of free-standing cannula 1800. In one embodiment, cannula 1800 includes a proximal portion 1804, which is removably coupled to the clamp 1754, and a tube 1802 for passage of instrument shafts (as shown in FIG. 22). Once the cannula 1800 is mounted in clamp 1754, the clamp may keep cannula 1800 from rotating. In one example, tube 1802 is comprised of stainless steel, and an interior surface of tube 1802 may be coated or lined with a lubricating or anti-friction material, although the cannula may be comprised of other materials, liners or no liners. Proximal portion 1804 may include exterior ridges 1806, 1808 and an interior space for receipt of an entry guide with channels, as shown in FIGS. 22 and 23A-23B and as described in more detail below. Examples of applicable accessory clamps and accessories, such as cannulas, are disclosed in pending U.S. patent application Ser. No. 11/240,087, filed Sep. 30, 2005, the full disclosure of which is incorporated by reference herein for all purposes.

Referring now to FIGS. 22 and 23A-23B in accordance with embodiments of the present disclosure, FIG. 22 illustrates a cross-sectional view of the cannula 1800 of FIG. 21, and a cross-sectional view of a mounted entry guide tube 2200. Instrument manipulators 1942 are coupled to a rotatable base plate 1940 of a manipulator platform, in one example by telescoping insertion mechanisms 1942a, and instruments 2160 are mounted to the instrument manipulators 1942 (e.g., on a distal or proximal face of the instrument manipulator). In one embodiment, the telescoping insertion mechanisms 1942a are symmetrically mounted to the rotatable base plate 1940, and in one example are set apart 90 degrees from one another to provide for four instrument manipulators. Other configurations and number of insertion mechanisms (and therefore instrument manipulators and instruments) are possible.

Thus, the instruments 2160 are mounted to the instrument manipulators 1942 such that the instrument shafts 2160b are clustered around manipulator assembly roll axis 1941. Each shaft 2160b extends distally from the instrument's force transmission mechanism 2160a, and all shafts extend through cannula 1800 placed at the port into the patient. The cannula 1800 is removably held in a fixed position with reference to base plate 1940 by cannula mount 1750, which is coupled to fourth manipulator link 138 in one embodiment. Entry guide tube 2200 is inserted into and freely rotates within cannula 1800, and each instrument shaft 2160b extends through an associated channel 2204 in the guide tube 2200. The central longitudinal axes of the cannula and guide tube are generally coincident with the roll axis 1941. Therefore, as the base plate 1940 rotates to rotate the instrument manipulators and respective instrument shafts, the guide tube 2200 rotates within the cannula as base plate 1940 rotates. In one example, entry guide tube 2200 is freely rotatable within the cannula about a central longitudinal axis of the guide tube, which is aligned to a central longitudinal axis of the cannula, which in turn is aligned or runs parallel to the roll axis 1941 of the manipulator platform. In other embodiments, the entry guide tube 2200 may be fixedly mounted to the cannula if such fixed support for the instrument shafts is desirable.

The cross-sectional view of entry guide tube 2200 is taken along a line III-III in FIGS. 23A and 23B, which illustrate a side view and a top view, respectively, of an entry guide tube 2200 having a coupling lip 2202, a tube 2206, and channels 2204a, 2204b. Entry guide tube 2200 includes lip 2202 on a proximal end of the tube 2206 to rotatably couple the entry guide to the proximal portion 1804 of cannula 1800. In one example, lip 2202 couples between ridges (e.g., ridges 1806 and 1808 in FIG. 22) of the cannula. In other embodiments, the entry guide does not need a coupling lip, as will be further described below.

Entry guide tube 2200 further includes channels 2204a, 2204b through the entry guide for passage of instrument shafts (e.g., instrument shafts 2160b in FIG. 22). In one aspect, one channel or passageway is provided per instrument shaft and the channels may have different geometric shapes and sizes. As illustrated in FIGS. 23A and 23B, channel 2204a is of a different shape and size from channels 2204b, and in one example, channel 2204a is used to guide a camera instrument which has a larger and more rigid shaft, and channels 2204b are used to guide instrument shafts of typical instruments. Other shapes and sizes of the channels are applicable, including but not limited to openings which are shaped as a circle, an oval, an ellipse, a triangle, a square, a rectangle, and a polygon.

As the base plate rotates about the roll axis 1941, the cluster of instrument manipulators 1942 and instruments 2160 also rotate about the roll axis. As instrument shafts 2160b rotate about roll axis 1941 while in channels 2204 of the entry guide, an instrument shaft impinges against an interior surface of an entry guide channel, and at least one rotating instrument shaft drives entry guide tube 2200 to rotate relative to and within cannula 1800, which is clamped and kept stationary by the clamp of a cannula mount; e.g., clamp 1754 of cannula mount 1750.

The instrument shafts may be inserted and retracted through the entry guide channels independently or in coordination with one another by movement of respective insertion mechanisms 1942a. The instruments 2160 may rotate in a clockwise or counterclockwise direction about roll axis 1941, and accordingly, entry guide tube 2200 may correspondingly rotate in a clockwise or counterclockwise direction about the roll axis. It is further noted that although four channels are illustrated in the entry guide and a plurality of instrument shafts are illustrated as passing through the entry guide and cannula, the entry guide and cannula assembly may function within the surgical system with other numbers of channels and instrument/instrument assembly shafts running through the entry guide and cannula. For example, an entry guide tube with one or more channels for running one or more instrument/instrument assembly shafts through the entry guide and cannula is within the scope of the present disclosure. Furthermore, torque provided by the instrument shafts to rotate the entry guide need not be symmetrically provided by a plurality of instrument shafts but may be provided asymmetrically and independently, including the majority of the torque being provided by a single instrument shaft.

In one embodiment, entry guide tube 2200 and cannula 1800 may each include an electronic interface or a wireless interface, such as a radio frequency identification (RFID) chip or tag, which includes identifying information about the cannula and/or entry guide tube and allows for the surgical system (e.g., read by the manipulator arm) to recognize the identification of a particular entry guide and/or cannula. Metal rings, mechanical pins, and inductive sensing mechanisms may also be used to read identification data. This electronic or wireless interface allows data (e.g., entry guide tube/cannula type) to be transferred to the surgical system. Details about mechanical and electrical interfaces for various instruments, guide tubes, and imaging systems, and also about sterile draping to preserve the sterile field, are discussed in U.S. Pat. No. 6,866,671 (Tierney et al.) and U.S. Pat. No. 6,132,368 (Cooper), both of which are incorporated by reference, and which may be similarly used with the entry guide and cannula.

Figure 24:
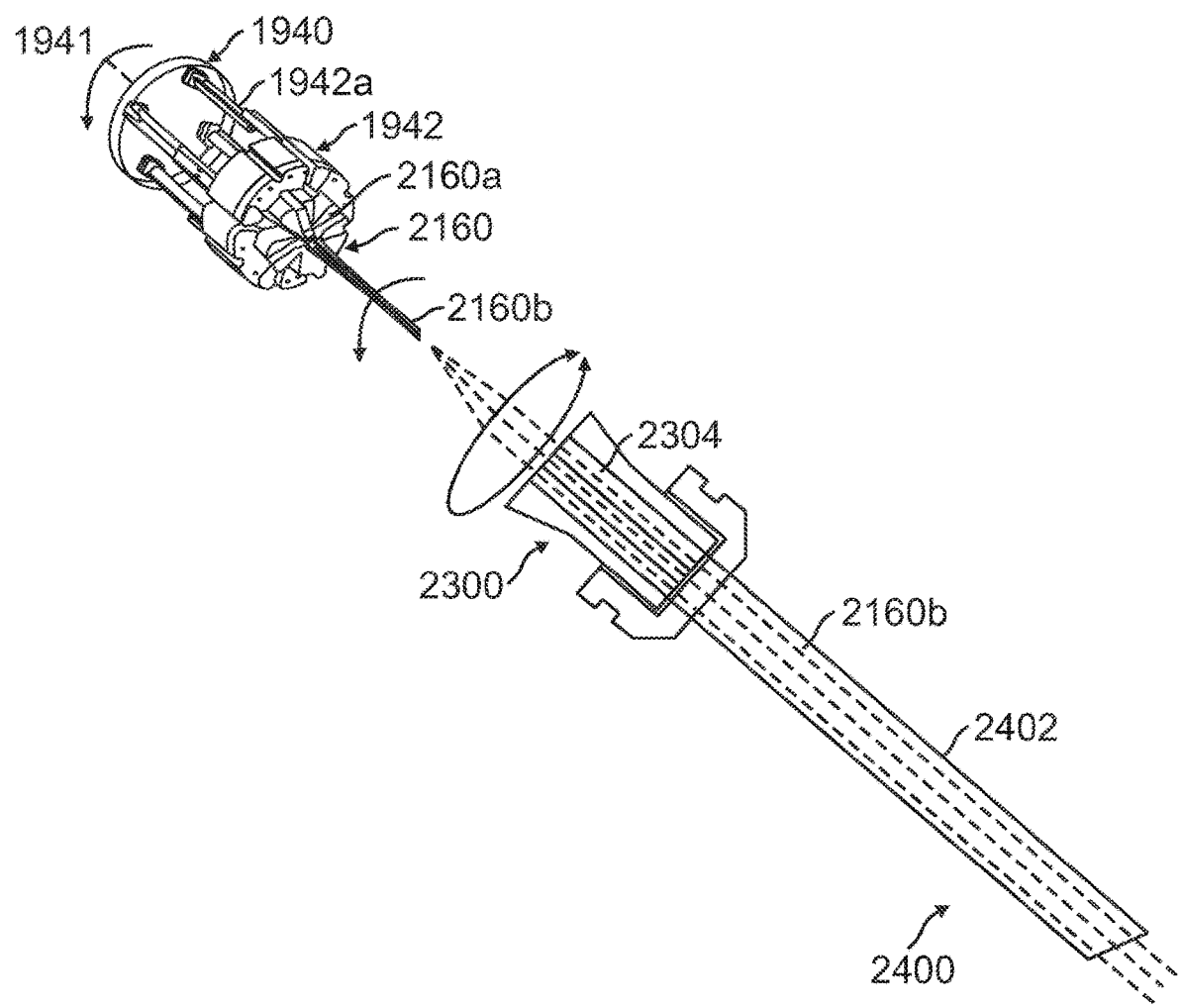
FIG. 24 illustrates a cross-sectional view of another cannula and another mounted entry guide in combination with instruments mounted to instrument manipulators on a manipulator platform in accordance with an embodiment of the present disclosure.

It is further noted that in other embodiments, the entry guide tube may not include a coupling lip. FIG. 24 illustrates a cross-sectional view of an entry guide tube 2300 mounted to a cannula 2400. Entry guide tube 2300 includes channels 2304 and is similar to entry guide tube 2200 described above but does not include a coupling lip. Instead, entry guide tube 2300 is rotatably coupled to the proximal portion of the cannula by impingement force of the instrument shafts 2160b against the interior walls of the entry guide tube channels 2304. It is further noted that the cannula need not include exterior ridges at a proximal portion. It is further noted that in one aspect, the entry guide tube may move rotatably and longitudinally along the cannula's longitudinal axis or the roll axis, driven by the instrument shafts running through the entry guide tube.

Figure 24A:
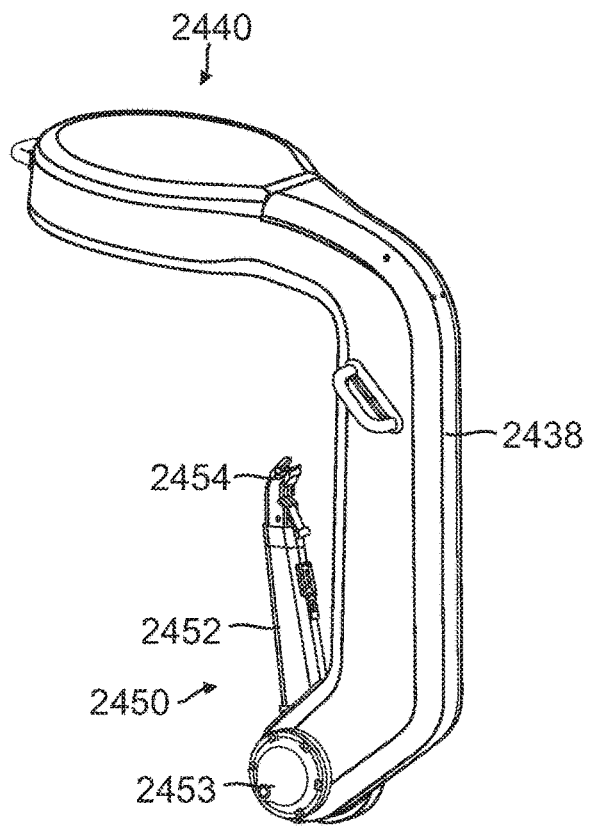
FIGS. 24A-24B illustrate perspective views of another movable cannula mounting arm in a retracted position and a deployed position, respectively.
Figure 24B:
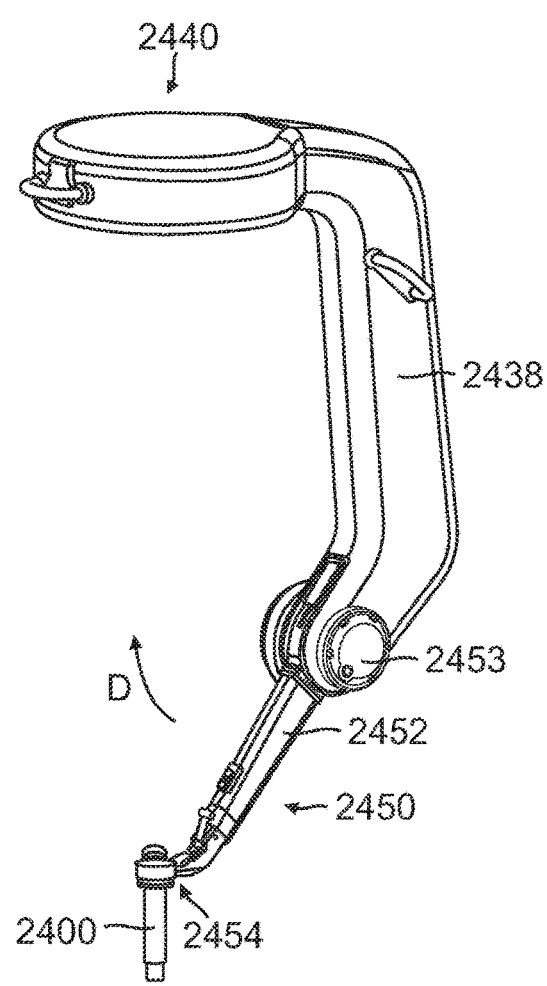

Referring now to FIGS. 24A-24D, a different embodiment of a cannula mounting arm, clamp, and cannula are illustrated which may be used with an entry guide as described above. FIGS. 24A and 24B illustrate perspective views of an embodiment of a movable and/or detachable cannula mount 2450 in a retracted position and a deployed operating position, respectively. Cannula mount 2450 includes an extension 2452 that is movably coupled to a link 2438 of the manipulator arm having an instrument manipulator assembly platform 2440, such as adjacent a proximal end of fourth manipulator link 138 (FIGS. 1A and 1B). In one implementation, extension 2452 is coupled to link 2438 by a rotational joint 2453 that allows extension 2452 to move between a stowed position adjacent link 2438 and an operational position that holds the cannula in the correct position so that the remote center of motion is located along the cannula. In one implementation, extension 2452 may be rotated upwards or folded toward link 2438, as shown by arrow D, to create more space around the patient and/or to more easily don a drape over the cannula mount when draping the manipulator arm. Other joints may be used to couple the extension 2452, including but not limited to a ball and socket joint or a universal joint, a sliding joint to create a telescoping effect, and the like, so that the extension may be moved closer to the link in order to reduce the overall form factor of the cannula mount and manipulator arm. In another embodiment, the extension 2452 may be internally telescoping relative to the manipulator arm, or the extension 2452 may be detachable from and operably couplable to the link.

Figure 24C:
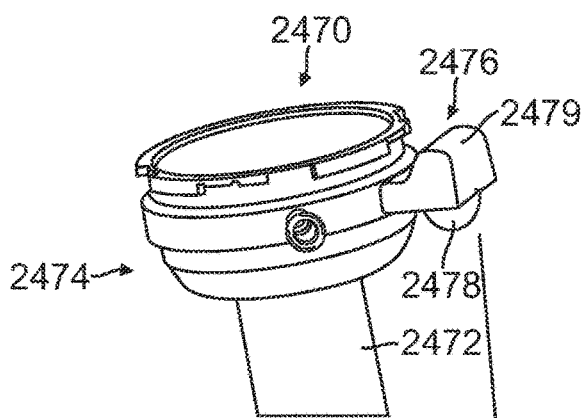
FIG. 24C illustrates a proximal top section of a cannula in accordance with another embodiment.
Figure 24D:
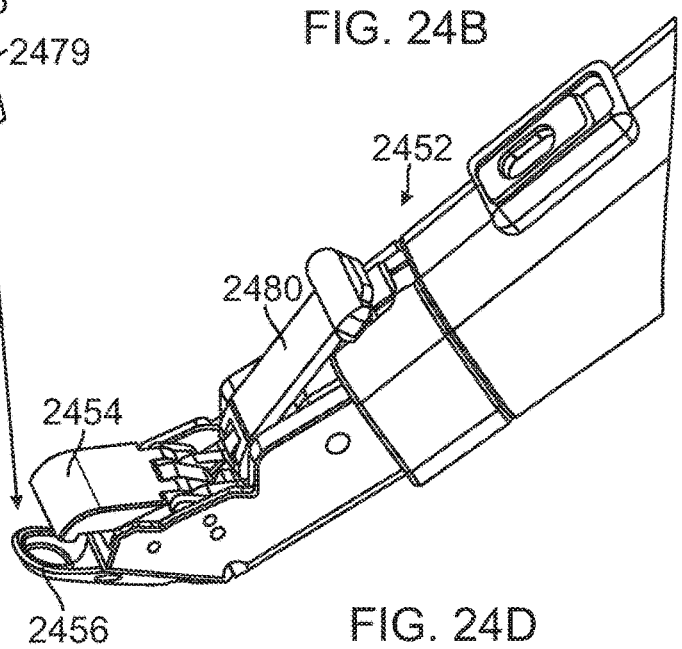
FIG. 24D illustrates a cannula clamp at a distal end of a cannula mounting arm in accordance with another embodiment.

Cannula mount 2450 further includes a clamp 2454 over a receptacle 2456 on a distal end of extension 2452. FIG. 24C illustrates a perspective view of a cannula 2470 mountable to clamp 2454 and receptacle 2456 of cannula mount 2450 as illustrated in FIG. 24D. In one embodiment, cannula 2470 includes a proximal portion 2474 having a boss 2476. Boss 2476 includes a bottom hemispherical surface 2478 that is positioned within the mating receptacle 2456 (as shown by the arrow from hemispherical surface 2478 to receptacle 2456). Boss 2476 further includes a top surface 2479 which is engaged by clamp 2454 to lock the boss in position and therefore the cannula 2470 in a fixed position relative to cannula mount extension 2452. Clamp 2454 is actuated by a lever 2480. Cannula 2470 further includes a tube 2472 for passage of instrument shafts (as shown in FIGS. 22 and 24). Once the cannula 2470 is mounted by clamp 2454 and receptacle 2456, the clamp may keep cannula 2470 from rotating. In one example, tube 2472 is comprised of stainless steel, and an interior surface of tube 2472 may be coated or lined with a lubricating or anti-friction material, although the cannula may be comprised of other materials, liners or no liners. Proximal portion 2474 includes an interior space for receipt of an entry guide with channels, as shown in FIGS. 22, 23A-23B, and 24. Examples of applicable accessory clamps and accessories, such as cannulas, are disclosed in pending U.S. application Ser. No. 11/240,087, filed Sep. 30, 2005, the full disclosure of which is incorporated by reference herein for all purposes.

In one aspect, the entry guide and cannula assemblies described above support insufflation and procedures requiring insufflation gas at the surgical site. Further disclosure of insufflation through the entry guide and cannula assembly may be found in U.S. application Ser. No. 12/705,439, filed Feb. 12, 2010 and entitled "Entry Guide for Multiple Instruments in a Single Port System", the full disclosure of which is incorporated by reference herein for all purposes.

Advantageously, because the entry guide is dependently driven by the instrument shaft(s), the need for a motor or other actuating mechanism to rotate the entry guide is eliminated. Furthermore, the entry guide allows for the removal of a bulky actuator mechanism near the patient or surgical site. Thus, the entry guide and cannula assembly provide for an efficient and robust means to advantageously organize and support multiple instruments through a single port and reduce collisions between instruments and other apparatus during a surgical procedure.

Single Port Surgical System Architecture

FIGS. 25A-25C, 26A-26C, and 27A-27C illustrate different views of a surgical system 2500 with an instrument manipulator assembly roll axis or instrument insertion axis pointed at different directions relative to a patient P. FIGS. 25A-25C illustrate a manipulator assembly roll axis 2541 directed downward and toward patient P's head H. FIGS. 26A-26C illustrate manipulator assembly roll axis 2541 directed downward and toward patient P's feet F. FIGS. 27A-27C illustrate manipulator assembly roll axis 2541 directed upward and toward patient P's head H.

Surgical system 2500 includes a setup link 2518 for locating a remote center of motion for the robotic surgical system, and a manipulator arm assembly 2501 including an active proximal link 2526 and an active distal link 2528, in which the proximal link 2526 is operably coupled to the setup link 2518 by an active yaw joint 2524. A plurality of instrument manipulators 2542 form an instrument manipulator assembly which is rotatably coupled to a distal end of the distal link 2528. In one embodiment, the plurality of instrument manipulators are coupled to a manipulator assembly platform 2540 by telescoping insertion mechanisms 2544. The plurality of instrument manipulators 2542 are rotatable about the roll axis 2541. In one embodiment, each of the plurality of instrument manipulators includes a distal face from which a plurality of actuator outputs distally protrude, and a plurality of surgical instruments 2560 are coupled to the distal face of a corresponding instrument manipulator. A cannula mount 2550 is movably coupled to the distal link 2528, and a cannula and entry guide tube assembly 2552 is coupled to the cannula mount 2550. In one embodiment, the cannula has a central longitudinal axis substantially coincident with the roll axis 2541. Each surgical instrument has a shaft passing through the entry guide tube and the cannula, such that rotation of at least one instrument shaft rotates the entry guide tube about the longitudinal axis of the cannula.

A vertical manipulator assembly yaw axis 2523 at yaw joint 2524 allows the proximal link 2526 to rotate substantially 360 degrees or more about the remote center of motion for the surgical system (see, e.g., FIG. 2C). In one instance the manipulator assembly yaw rotation may be continuous, and in another instance the manipulator assembly yaw rotation is approximately .+–. 180 degrees. In yet another instance, the manipulator assembly yaw rotation may be approximately 660 degrees. Since the instruments are inserted into the patient in a direction generally aligned with manipulator assembly roll axis 2541, the manipulator arm assembly 2501 can be actively controlled to position and reposition the instrument insertion direction in any desired direction around the manipulator assembly yaw axis (see, e.g., FIGS. 25A-25C showing the instrument insertion direction toward a patient's head, and FIGS. 26A-26C showing the instrument insertion direction toward a patient's feet). This capability may be significantly beneficial during some surgeries. In certain abdominal surgeries in which the instruments are inserted via a single port positioned at the umbilicus (see, e.g., FIGS. 25A-25C), for example, the instruments may be positioned to access all four quadrants of the abdomen without requiring that a new port be opened in the patient's body wall. Multi-quadrant access may be required for, e.g., lymph node access throughout the abdomen. In contrast, the use of a multi-port telerobotic surgical system may require additional ports be made in the patient's body wall to more fully access other abdominal quadrants.

Additionally, the manipulator may direct the instrument vertically downwards and in a slightly pitched upwards configuration (see, e.g., FIGS. 27A-27C showing the instrument insertion direction pitched upwards near a body orifice O). Thus, the angles of entry (both yaw and pitch about the remote center) for an instrument through a single entry port may be easily manipulated and altered while also providing increased space around the entry port for patient safety and patient-side personnel to maneuver.

Furthermore, the links and active joints of the manipulator arm assembly 2501 may be used to easily manipulate the pitch angle of entry of an instrument through the single entry port while creating space around the single entry port. For example, the links of the arm assembly 2501 may be positioned to have a form factor "arcing away" from the patient. Such arcing away allows rotation of the manipulator arm about the yaw axis 2523 that does not cause a collision of the manipulator arm with the patient. Such arcing away also allows patient side personnel to easily access the manipulator for exchanging instruments and to easily access the entry port for inserting and operating manual instruments (e.g., manual laparoscopic instruments or retraction devices). In other terms, the work envelope of the cluster of instrument manipulators 2542 may approximate a cone, with the tip of the cone at the remote center of motion and the circular end of the cone at the proximal end of the instrument manipulators 2542. Such a work envelope results in less interference between the patient and the surgical robotic system, greater range of motion for the system allowing for improved access to the surgical site, and improved access to the patient by surgical staff.

Accordingly, the configuration and geometry of the manipulator arm assembly 2501 in conjunction with its large range of motion allow for multi-quadrant surgery through a single port. Through a single incision, the manipulator may direct the instrument in one direction and easily change direction; e.g., working toward the head a patient (see, e.g., FIGS. 25A-25C) and then changing direction toward the pelvis of the patient (see, e.g., FIGS. 26A-26C), by moving the manipulator arm about the constantly vertical yaw axis 2523.

Figure 28:
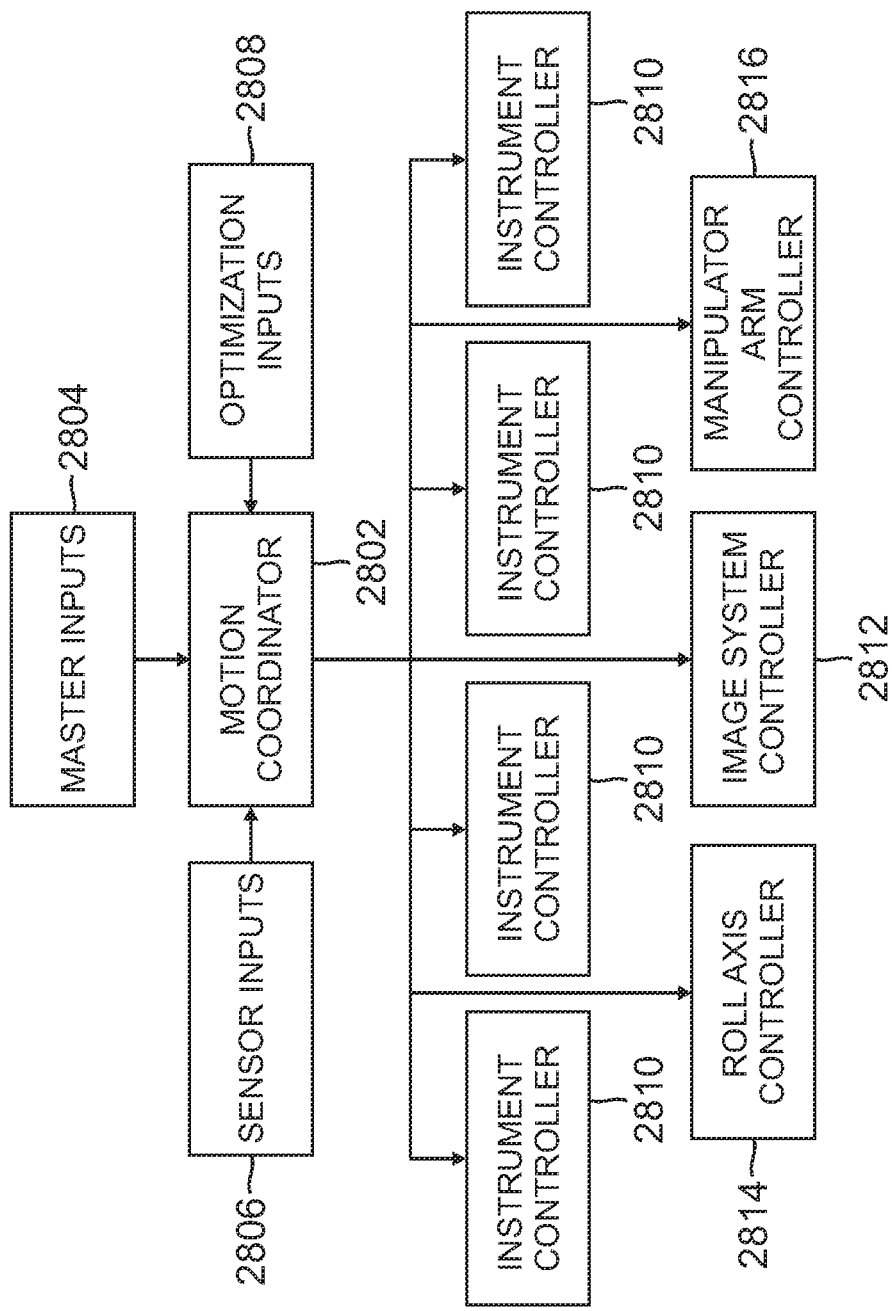
FIG. 28 is a diagrammatic view of a centralized motion control system for a minimally invasive telesurgical system in accordance with an embodiment.

Referring now to FIG. 28, a diagrammatic view illustrates aspects of a centralized motion control and coordination system architecture for minimally invasive telesurgical systems that incorporate surgical instrument assemblies and components described herein. A motion coordinator system 2802 receives master inputs 2804, sensor inputs 2806, and optimization inputs 2808.

Master inputs 2804 may include the surgeon's arm, wrist, hand, and finger movements on the master control mechanisms. Inputs may also be from other movements (e.g., finger, foot, knee, etc. pressing or moving buttons, levers, switches, etc.) and commands (e.g., voice) that control the position and orientation of a particular component or that control a task-specific operation (e.g., energizing an electrocautery end effector or laser, imaging system operation, and the like).

Sensor inputs 2806 may include position information from, e.g., measured servomotor position or sensed bend information. U.S. patent application Ser. No. 11/491,384 (Larkin, et al.) entitled "Robotic surgery system including position sensors using fiber Bragg gratings", incorporated by reference, describes the use of fiber Bragg gratings for position sensing. Such bend sensors may be incorporated into the various instruments and imaging systems described herein to be used when determining position and orientation information for a component (e.g., an end effector tip). Position and orientation information may also be generated by one or more sensors (e.g., fluoroscopy, MRI, ultrasound, and the like) positioned outside of the patient, and which in real time sense changes in position and orientation of components inside the patient.

As described below, the user interface has three coupled control modes: a mode for the instrument(s), a mode for the imaging system, and a mode for the manipulator arm configuration and/or roll axis control. A mode for the guide tube(s) may also be available. These coupled modes enable the user to address the system as a whole rather than directly controlling a single portion. Therefore, the motion coordinator must determine how to take advantage of the overall system kinematics (i.e., the total DOFs of the system) in order to achieve certain goals. For example, one goal may be to optimize space around the patient or to minimize the form factor of the manipulator arm. Another goal may be optimize instrument workspace for a particular configuration. Another goal may be to keep the imaging system's field of view centered between two instruments. Therefore, optimization inputs 2808 may be high-level commands, or the inputs may include more detailed commands or sensory information. An example of a high level command would be a command to an intelligent controller to optimize a workspace. An example of a more detailed command would be for an imaging system to start or stop optimizing its camera. An example of a sensor input would be a signal that a workspace limit had been reached.

Motion coordinator 2802 outputs command signals to various actuator controllers and actuators (e.g., servomotors) associated with manipulators for the various telesurgical system arms. FIG. 28 depicts an example of output signals being sent to four instrument controllers 2810, to an imaging system controller 2812, to a roll axis controller 2814, and to a manipulator arm controller 2816, which then can send control signals to instrument actuators, active arm joints, rotation mechanisms of the manipulator platform, and active telescoping insertion mechanisms. Other numbers and combinations of controllers may be used. Control and feedback mechanisms and signals, such as position information (e.g., from one or more wireless transmitters, RFID chips, etc.) and other data from a sensing system, are disclosed in U.S. patent application Ser. No. 11/762,196, which is incorporated by reference, and are applicable in the present disclosure.

Accordingly, in some aspects the surgeon who operates the telesurgical system will simultaneously and automatically access at least the three control modes identified above: an instrument control mode for moving the instruments, an imaging system control mode for moving the imaging system, and a manipulator arm roll axis control mode for configuring the links of the manipulator arm into a certain form factor or relative to one another or the rotation of the manipulator platform, and also for active movement about the outer yaw axis to enable multi-quadrant surgery. A similar centralized architecture may be adapted to work with the various other mechanism aspects described herein.

Figure 29:
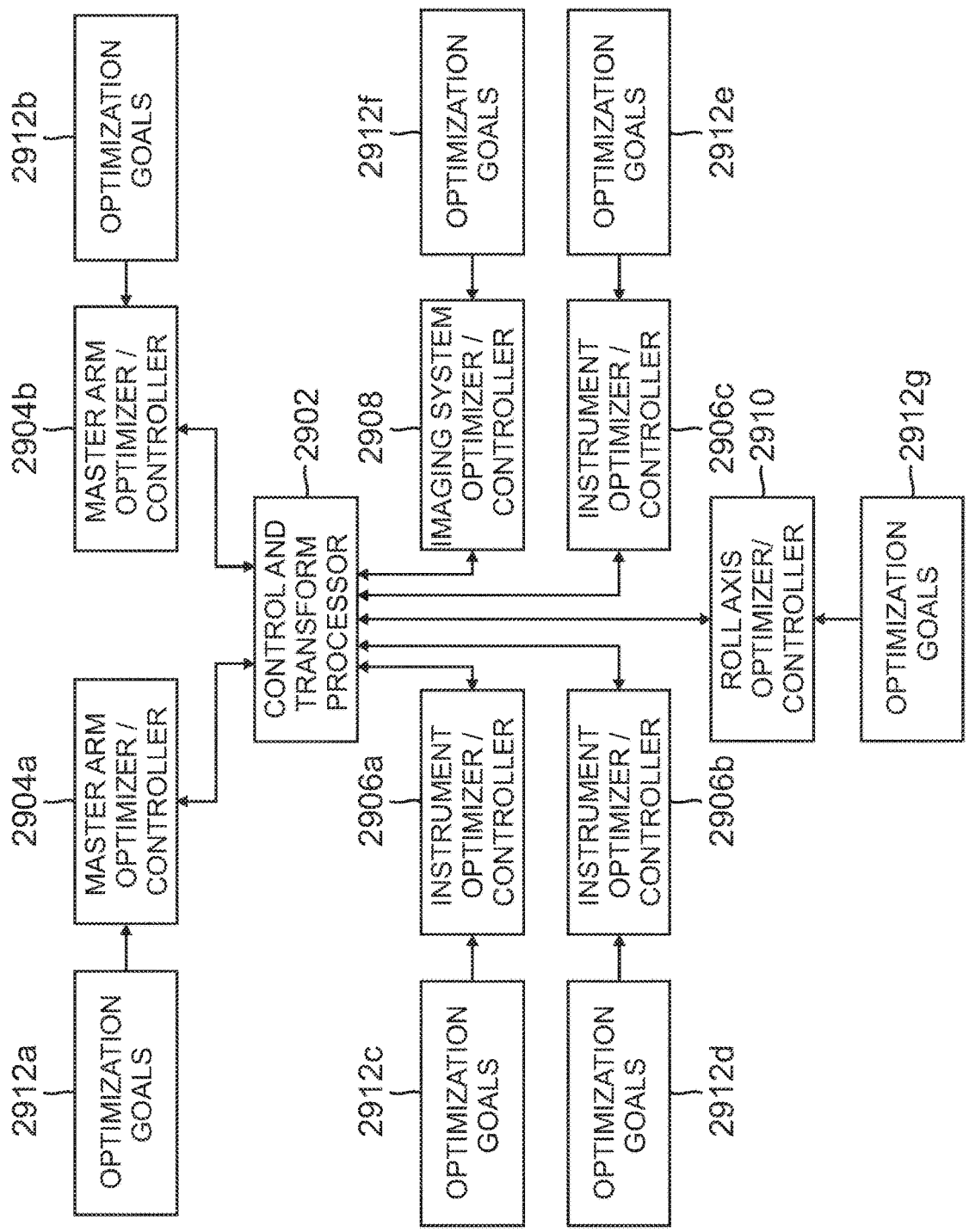
FIG. 29 is a diagrammatic view of a distributed motion control system for a minimally invasive telesurgical system in accordance with an embodiment.

FIG. 29 is a diagrammatic view that illustrates aspects of a distributed motion control and coordination system architecture for minimally invasive telesurgical systems that incorporate surgical instrument assemblies and components described herein. In the illustrative aspects shown in FIG. 29, control and transform processor 2902 exchanges information with two master arm optimizer/controllers 2904a, 2904b, with three surgical instrument optimizer/controllers 2906a, 2906b, 2906c, with an imaging system optimizer/controller 2908, and with a roll axis optimizer/controller 2910. Each optimizer/controller is associated with a master or slave arm (which includes, e.g., the camera (imaging system) arm, the instrument arms, and the manipulator arm) in the telesurgical system. Each of the optimizer/controllers receives arm-specific optimization goals 2912a-2912g.

The double-headed arrows between control and transform processor 2902 and the various optimizer/controllers represent the exchange of Following Data associated with the optimizer/controller's arm. Following Data includes the full Cartesian configuration of the entire arm, including base frame and distal tip frame. Control and transform processor 2902 routes the Following Data received from each optimizer/controller to all the optimizer/controllers so that each optimizer/controller has data about the current Cartesian configuration of all arms in the system. In addition, the optimizer/controller for each arm receives optimization goals that are unique for the arm. Each arm's optimizer/controller then uses the other arm positions as inputs and constraints as it pursues its optimization goals. In one aspect, each optimization controller uses an embedded local optimizer to pursue its optimization goals. The optimization module for each arm's optimizer/controller can be independently turned on or off. For example, the optimization module for only the imaging system and the instrument arm may be turned on.

The distributed control architecture provides more flexibility than the centralized architecture, although with the potential for decreased performance. In this distributed architecture, however, the optimization is local versus the global optimization that can be performed with the centralized architecture, in which a single module is aware of the full system's state.

Link Counterbalance

Figure 30A:
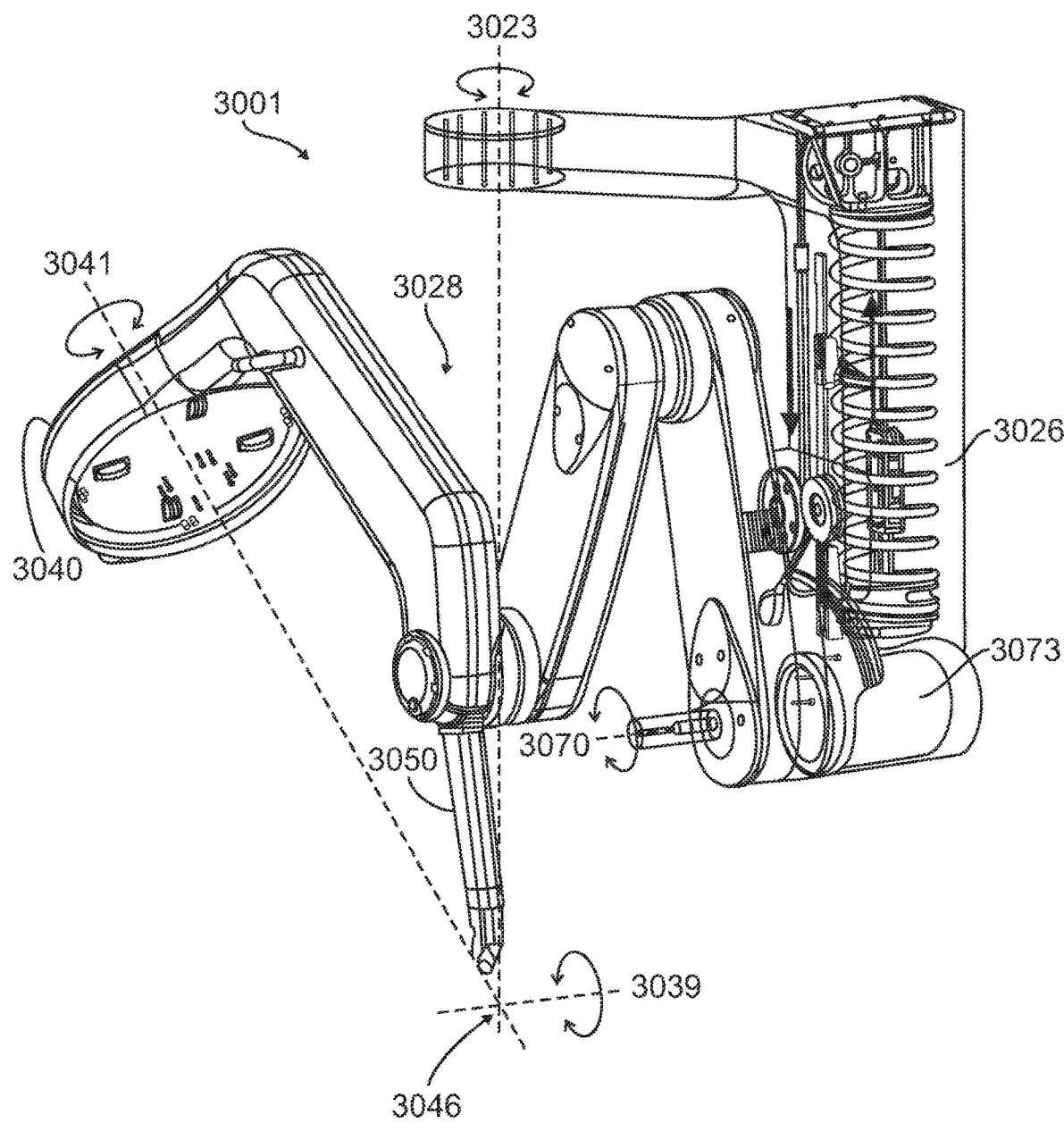
FIGS. 30A-30B illustrate different views of a counterbalancing link of a robotic surgical system in accordance with an embodiment.
Figure 30B:
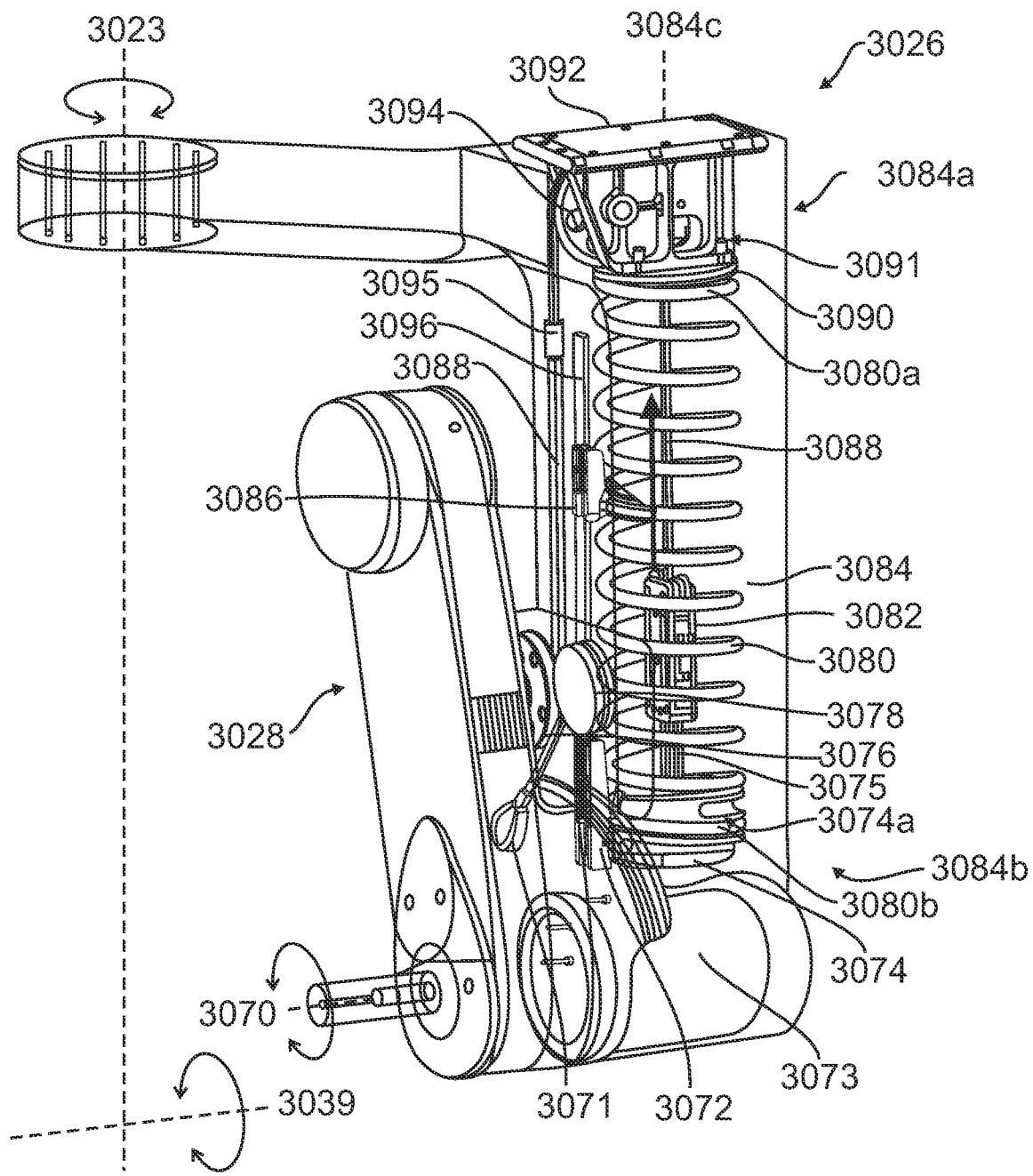
Figure 31:
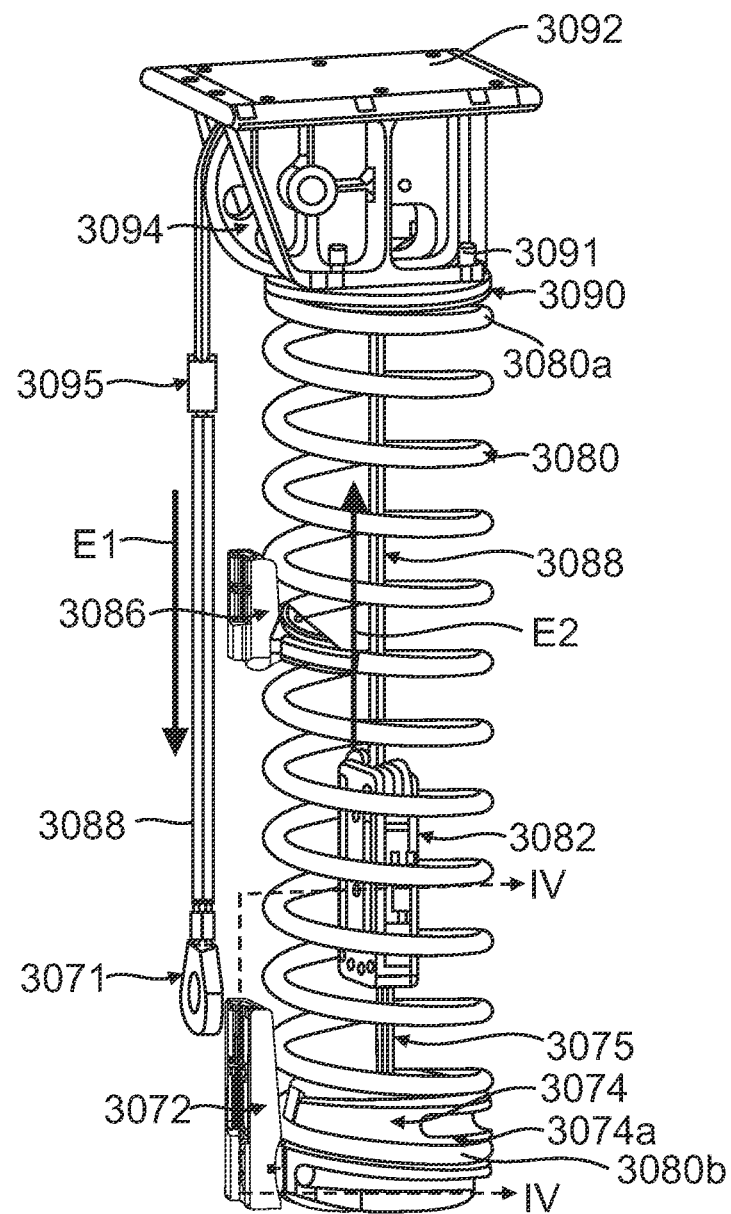
FIG. 31 illustrates a view of the counterbalancing link without an exterior housing in accordance with an embodiment.

An embodiment of a counterbalancing mechanism in a proximal link will now be described in greater detail with reference to FIGS. 30A-37C. FIG. 30A illustrates a manipulator arm assembly 3001 which is substantially similar to the arm assemblies described above, the features of which are applicable with respect to assembly 3001 as well, and FIG. 30B illustrates a closer view of the counterbalancing proximal link of the arm assembly 3001. FIGS. 31-37C illustrate different views and aspects of the counterbalancing system without the walls of a proximal link housing. In particular, FIG. 31 illustrates a perspective view of the counterbalancing system, FIGS. 32A-36C illustrate views of an adjustment pin, a linear guide, and a range of movement of the adjustment pin to move an end plug relative to the linear guide, and FIGS. 37A-37C illustrate detailed views from a distal end of the counterbalancing proximal link showing a rocker arm and set screws according to various aspects of the present disclosure.

Referring now to FIGS. 30A-30B, manipulator arm assembly 3001 includes a proximal link 3026 which is operably couplable to a setup link by a yaw joint to form a manipulator assembly yaw axis 3023. Proximal link 3026 is rotatably coupled to a distal link 3028 about a pivot axis 3070. In one example, a motor 3073 may be controlled to pivot the distal link 3028 about the pivot axis 3070. In one embodiment, distal link 3028 includes an instrument manipulator assembly platform 3040 at a distal end of the distal link. A cannula mount 3050 is movably coupled to the distal link 3028. In one embodiment, platform 3040 provides a rotatable base plate on which instrument manipulators may be mounted and rotated about an instrument manipulator assembly roll axis 3041. The intersection of yaw axis 3023, roll axis 3041, and an instrument manipulator assembly pitch axis 3039 form a remote center of motion 3046 as has been previously described above.

Referring now in particular to FIGS. 30B and 31, counterbalancing link 3026 includes a housing 3084 having a central longitudinal axis 3084c that runs between a housing proximal end or first end 3084a and a housing distal end or second end 3084b. A compression spring 3080 is disposed along the longitudinal axis 3084c and has a spring proximal end or first end 3080a and a spring distal end or second end 3080b. In one embodiment, the compression spring is comprised of silicon chrome alloy, but may be comprised of other materials. A base 3092 is disposed at the first end of the housing and is coupled to the first end 3080a of the compression spring 3080 by an alignment ring 3090 therebetween. A plug 3074 is disposed at the second end of the housing and is coupled to the second end 3080b of the compression spring 3080. In one embodiment, alignment ring 3090 is fixedly coupled to first end 3080a of the compression spring 3080, and plug 3074 includes an external screw thread (e.g., screw thread 3074a) onto which is screwed the spring second end 3080b.

A cable 3088 having a coupler 3071 at a first end of the cable is coupled to a load from the distal link 3028, and a second end of the cable 3088 is operably coupled to the plug 3074. From the load bearing end of cable 3088 at coupler 3071, cable 3088 passes through a plurality of pulleys 3076 and 3078 outside of housing 3084, and then through a pulley 3094 at base 3092 prior to coupling to plug 3074. The load from the distal link 3028 pulls cable 3088 in directions E1 and E2 about pulley 3094 (FIG. 31), causing plug 3074 to compress spring 3080 in the E2 direction, which is set to counterbalance at least a portion of the load from the distal link about the pivot axis 3070.

In order to increase safety, cable 3088 may include redundant cables which are coupled to a cable tension equalizer 3082 that equalizes tension across the redundant cables. A cable twister 3095 is optionally used to operably couple the redundant cables to one another between pulley 3094 and coupler 3071. A plurality of cap screws 3075 may be disposed between the cable tension equalizer 3082 and the plug 3074, and may be used to adjust the force offset of the counterbalancing link. In one embodiment, three cap screws 3075 couple the cable tension equalizer 3082 and the plug 3074 with one cap screw bearing substantially all of the tension and the other two cap screws provided for redundancy and safety purposes.

In one aspect, the portion of cable 3088 between pulley 3094 and plug 3074 runs substantially along the central longitudinal axis 3084c of the proximal link housing. In a further aspect, spring 3080 compresses substantially along the central longitudinal axis 3084c of the proximal link housing. Spring compression can however cause "bowing" or non-linear compression of the spring along the longitudinal axis of the housing, which can lead to scraping and contact of the spring against the inner surface of the proximal link housing. In order to reduce or substantially eliminate bowing, the orientation of spring 3080 at both the first and second ends 3080a and 3080b may be adjusted in accordance with various aspects of the present disclosure. Furthermore, in one embodiment, the housing includes a linear guide track 3096 disposed parallel to the longitudinal axis of the housing 3084c. A linear guide 3086 that is movably or slidably joined to the linear guide track 3096 is fixedly coupled to a coil of the compression spring 3080. A linear guide 3072 that is also movably or slidably joined to the linear guide track 3096 is operably coupled to the plug 3074. The linear guide track 3096 and linear guides 3086 and 3072 further reduce or substantially eliminate bowing of the compression spring 3080. It should be noted that in some embodiments, the counterbalancing system may be operated without linear guides and a linear guide track.

Referring now to adjustable alignment of the first end or proximal end of the compression spring, in one aspect, alignment ring 3090 is movably coupled to base 3092 by a plurality of adjustment screws 3091, such that movement of the adjustment screws 3091 adjusts an orientation of the alignment ring 3090 and therefore an orientation of the first end of spring 3080a fixedly coupled to the alignment ring 3090. In one example, base 3092 is coupled to alignment ring 3090 by four adjustment screws 3091 set apart from one another in a square or rectangular configuration. Other geometric configurations of the screws are possible. The adjustment screws 3091 are each movable in a direction substantially perpendicular to a planar top surface of the alignment ring 3090 (e.g., via a screwing action through base apertures having interior screw threads) such that the orientation of the alignment ring may be adjusted at each point of contact with the adjustment screws. Accordingly, the orientation of the alignment ring 3090 and the fixedly coupled first end 3080a of spring 3080 may be adjusted at various points along the alignment ring 3090. More or less adjustment screws 3091 are within the scope of the present disclosure.

Referring now to FIGS. 32A-37C, detailed views from a distal end of the counterbalancing proximal link without the walls of the link housing are illustrated. In particular, the figures illustrate views of an adjustment pin 3106, a rocker arm 3108, and a range of movement of the adjustment pin and the rocker arm to adjust an orientation of the end plug 3074 and the fixedly coupled second end 3080b of spring 3080, according to various aspects of the present disclosure.

FIG. 32A illustrates a bottom perspective view of the counterbalancing system, and FIG. 32B illustrates a perspective view of a cross-section along line IV-IV of FIGS. 31, 32A, and 37A. As noted above, a plurality of cap screws 3075a and 3075b are disposed between and couple the cable tension equalizer 3082 and the plug 3074. Cap screw 3075a bears all the tension in this embodiment and the other two cap screws 3075b are provided for redundancy and safety purposes. As further noted above, a distal end of spring 3080 is coupled to plug 3074 by screwing onto external screw threads 3074a of the plug 3074. Plug 3074 may optionally include a plurality of grooves 3200 formed to lighten the weight of the plug. It is also noted that linear guide 3072 may be slidably coupled to linear guide track 3096 by linear guide flanges 3072a.

As can be seen in FIGS. 32A-32B, plug 3074 is coupled to linear guide 3072 by adjustment pin 3106, a socket screw 3104 that runs through an interior channel of the adjustment pin 3106, and a nut 3102 that screws onto a free end 3104a of socket screw 3104 to lock in place the position of the adjustment pin 3106 and linear guide 3072 relative to one another. In one embodiment, the socket screw 3104 is a hex socket screw. A head 3104b of the socket screw 3104 opposite the free end 3104a is placed within an engaging trench 3105 of the adjustment pin 3106 to lock the head portion of the socket screw within the adjustment pin when the nut 3102 is fully engaged at the free end 3104a of the socket screw, thus locking the position of adjustment pin 3106 and linear guide 3072 relative to one another.

Referring now to FIGS. 33-36C, adjusting movement of the adjustment pin 3106 relative to linear guide 3072 is described in greater detail. FIG. 33 illustrates a side view of the adjustment pin 3106 coupled to linear guide 3072, a circle 3114, and a circle center 3114a about which adjustment pin 3106 may pivot when the adjustment pin is not fully locked in place relative to linear guide 3072. FIG. 34 illustrates linear guide markings 3072b and adjustment pin markings 3106c when a central longitudinal axis 3107 of adjustment pin 3106 is perpendicular to a central longitudinal axis 3097 of the linear guide 3072 or guide track 3096. The linear guide markings 3072b and adjustment pin markings 3106c may be used by an adjuster of the counterbalancing system (and in particular the plug orientation) to determine relative positions of the adjustment pin and linear guide. FIG. 35 illustrates a perspective view of the adjustment pin 3106 including a pin shaft 3106a and a pin head 3106b. As can be seen in FIGS. 33-35, pin head 3106b has a curved top surface that operably mates with a curved surface of the linear guide 3072.

Figure 36A:
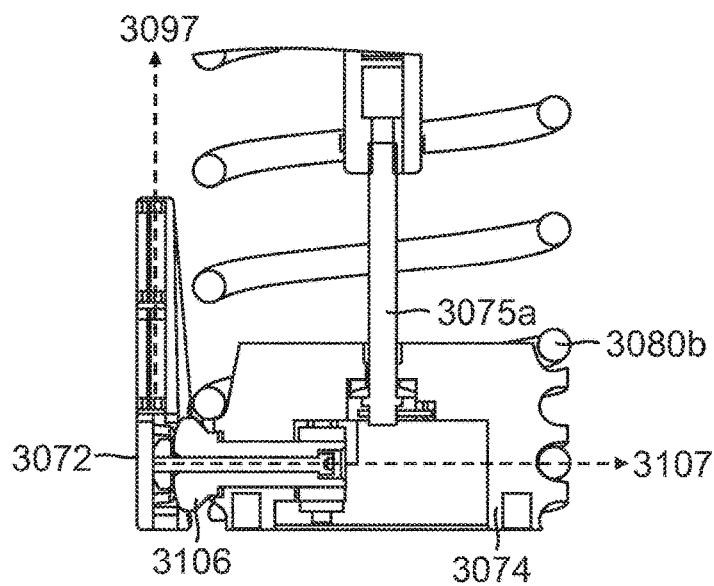
FIG. 36A-36C illustrate sectional side views showing a range of movement of the adjustment pin to move an end plug relative to the linear guide in accordance with various aspects of the present disclosure.
Figure 36B:
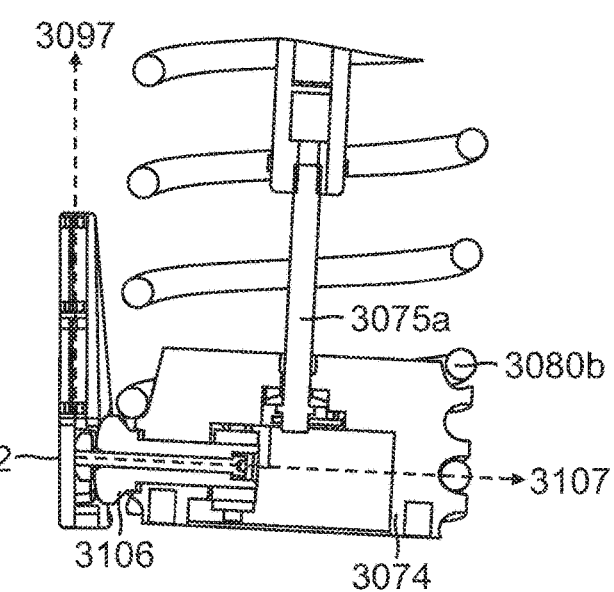
Figure 36C:
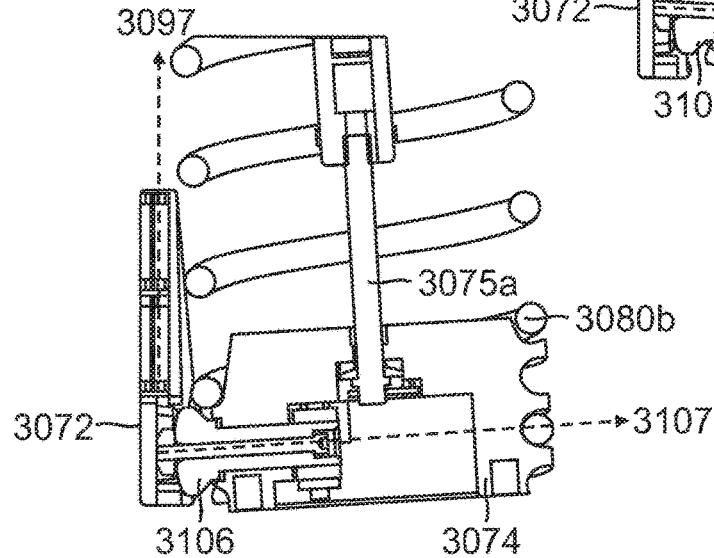
Figure 37A:
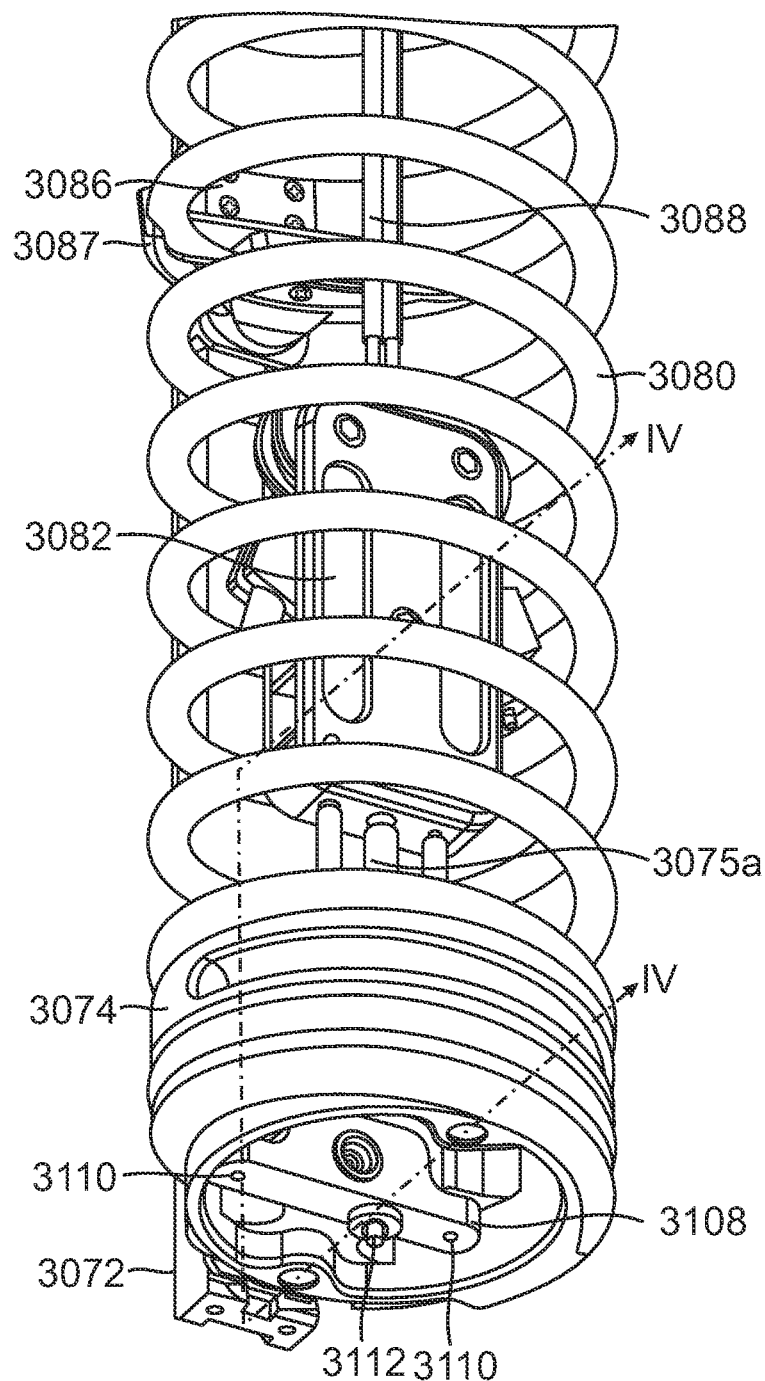
FIGS. 37A-37C illustrate detailed views from a distal end of the counterbalancing proximal link according to various aspects of the present disclosure.
Figure 37B:
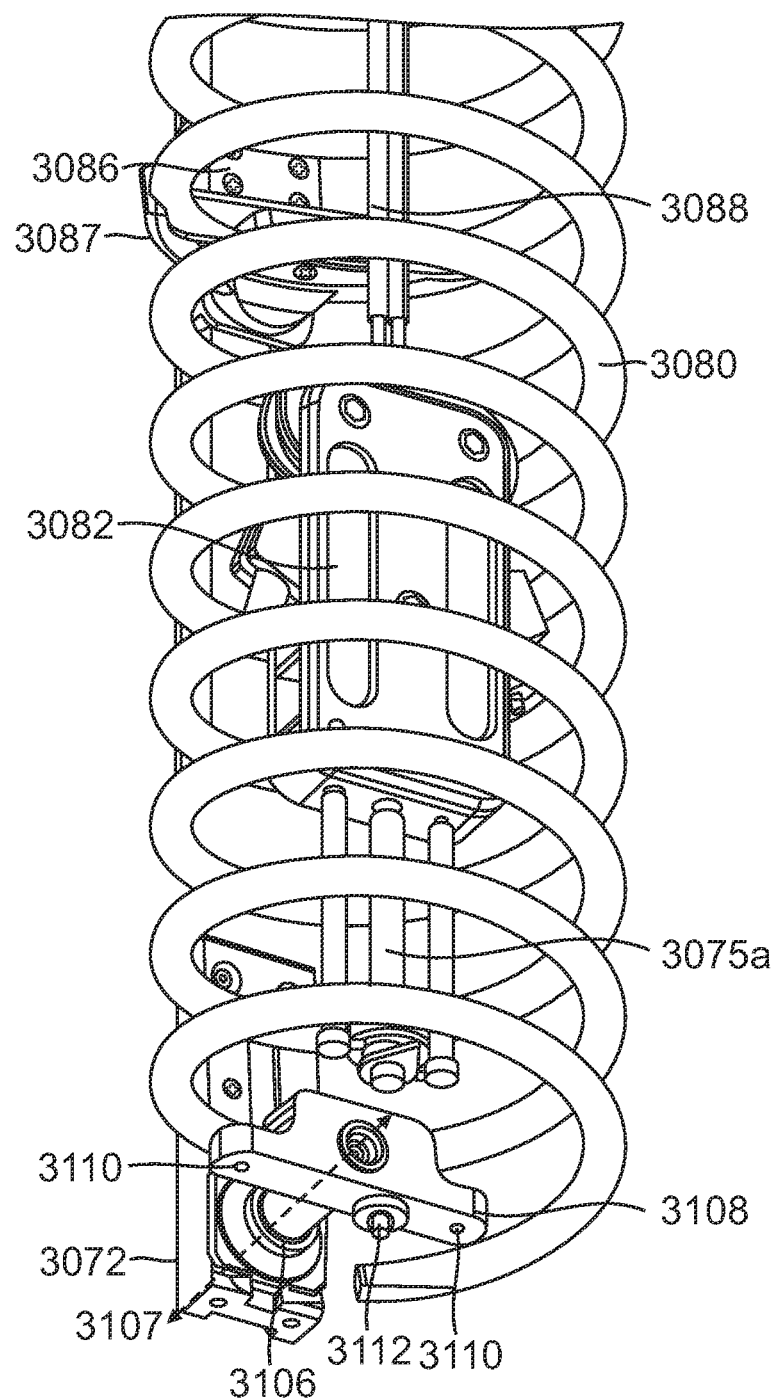
Figure 37C:
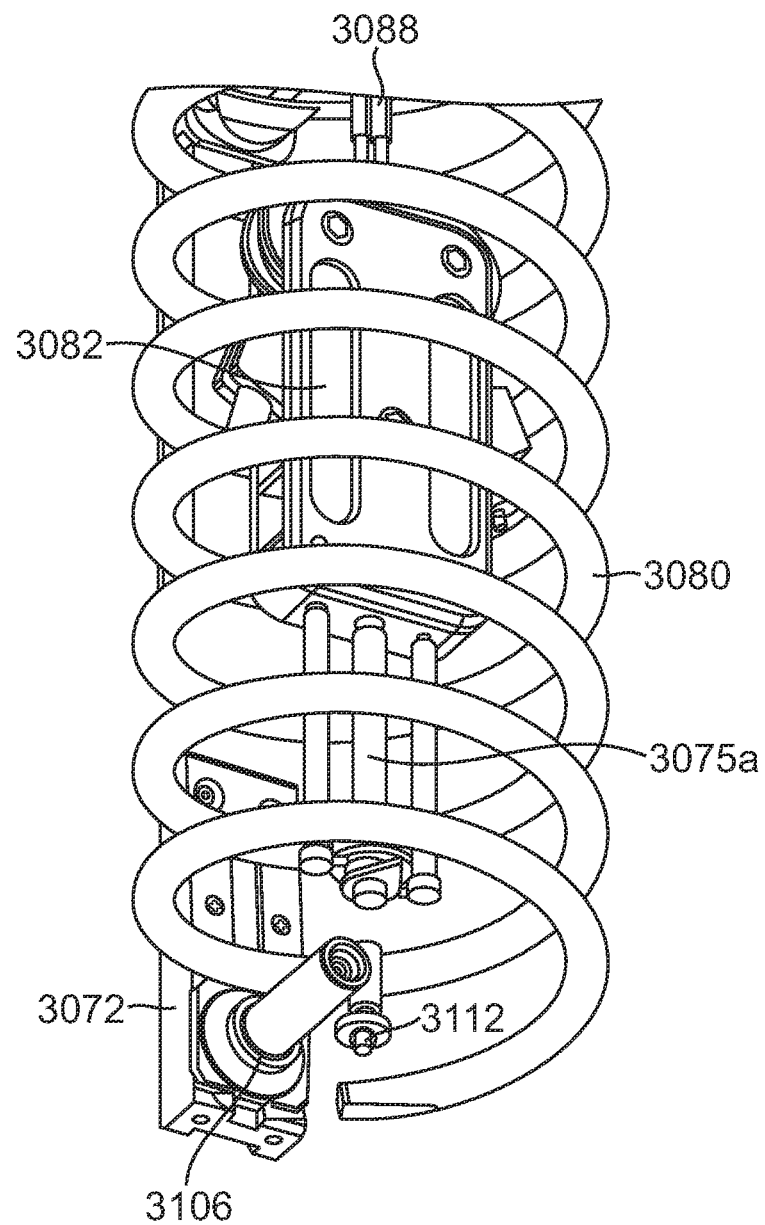

FIGS. 36A-36C illustrate side views of the adjustment pin 3106 and linear guide 3072 and their respective central longitudinal axis 3107 and 3097, respectively. FIG. 36A illustrates a perpendicular position of central longitudinal axis 3107 of adjustment pin 3106 relative to central longitudinal axis 3097 of linear guide 3072, FIG. 36B illustrates a position in which the central longitudinal axis 3107 of adjustment pin 3106 forms an obtuse angle with central longitudinal axis 3097 of linear guide 3072, and FIG. 36C illustrates a position in which the central longitudinal axis 3107 of adjustment pin 3106 forms an acute angel with central longitudinal axis 3097 of linear guide 3072. Accordingly, FIGS. 36A-36C illustrate the pivot movement of adjustment pin 3106 relative to linear guide 3072, and thus the orientation adjustment that may be made to plug 3074 and the fixedly coupled second end 3080b of spring 3080.

FIG. 37A illustrates another bottom perspective view of the counterbalancing system showing a rocker arm 3108 and set screws 3110, FIG. 37B illustrates FIG. 37A with the plug 3074 removed, and FIG. 37C illustrates FIG. 37B with the rocker arm 3108 removed. Rocker arm 3108 is coupled to adjustment pin 3106 at a free end of pin shaft 3106a and set screws 3110 couple the rocker arm 3108 to plug 3074. A cross disc pin 3112 clamps the rocker arm 3108 to adjustment pin 3106. Rocker arm 3108 and coupled plug 3074 may pivot about the central longitudinal axis 3107 of adjustment pin 3106 and may be adjusted by the movement of set screws 3110 in a direction substantially perpendicular to longitudinal axis 3107, for example by screwing action through rocker arm apertures having interior screw threads. Thus, the orientation of the plug 3074 and fixedly coupled second end 3080b of spring 3080 may be adjusted at each point of contact with the set screws 3110. More or less adjustment screws 3110 are within the scope of the present disclosure. Accordingly, the orientation of the plug and therefore the second or distal end of spring 3080 may be adjusted at various points by pivoting adjustment pin 3106 and pivoting rocker arm 3108. In one aspect, adjustment pin 3106 and rocker arm 3108 pivot about axes which are perpendicular to one another.

Furthermore, the counterbalancing link of the present disclosure allows for adjustment between the plug and the second end of the compression spring to change the number of active coils that are compressible in the compression spring. In one aspect, the second end of the compression spring may be screwed further or less onto the exterior screw threads of the plug to change the number of active coils that are compressible.

Advantageously, as a motor pivots the distal link 3028 about the pivot axis 3070 for increased and advantageous robot arm configuration and instrument manipulation, the counterbalancing proximal link 3026 allows for easier movements of the distal link, and less torque required from the motor pivoting the distal link, while also providing for increased safety from any motor failure. In some embodiments, although the counterbalancing mechanism of the proximal link was to totally fail, the motor pivoting the distal link may brake to hold the distal link in place.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

What is claimed is:

1. An instrument manipulator comprising:
   a frame comprising an outer shell and an inner frame, the inner frame being movably coupled to the outer shell;
   a plurality of actuator outputs protruding in a distal direction from the frame;
   an instrument support feature coupled to the outer shell; and
   a latching mechanism, the latching mechanism being configured to move the inner frame, the outer shell, or both relative to one another, so as to operably engage the plurality of actuator outputs with a plurality of actuator inputs of an instrument supported by the instrument support feature.

2. The instrument manipulator of claim 1, wherein the instrument support feature comprises one or more supports configured to engage with the instrument to couple the instrument to the instrument manipulator.

3. The instrument manipulator of claim 1, wherein the instrument support feature comprises one or more supports configured to engage with a sterile adaptor to couple the sterile adaptor to the instrument manipulator, the sterile adaptor to engage with the instrument.

4. The instrument manipulator of claim 3, wherein the plurality of actuator outputs are spring loaded to engage the plurality of actuator inputs through the sterile adaptor.

5. The instrument manipulator of claim 1, wherein the latching mechanism is configured to move the outer shell proximally relative to the inner frame to operably engage the plurality of actuator outputs with the plurality of actuator inputs while the instrument is supported by the instrument support feature.

6. The instrument manipulator of claim 1, wherein the latching mechanism is configured to move the outer shell distally relative to the inner frame to operably disengage the plurality of actuator outputs from the plurality of actuator inputs while the instrument is supported by the instrument support feature.

7. The instrument manipulator of claim 1, wherein the latching mechanism is configured to hold the inner frame stationary while moving the outer shell.

8. The instrument manipulator of claim 1, wherein the latching mechanism comprises a latch and a wire connected to the latch and to the inner frame.

9. The instrument manipulator of claim 1, wherein the latching mechanism comprises a latch handle configured to be folded inside a circumference of the instrument manipulator.

10. The instrument manipulator of claim 1, wherein the plurality of actuator outputs include a grip output lever, a joggle output gimbal, a wrist output gimbal, a roll output disk, or any combination of these.

11. The instrument manipulator of claim 1, wherein the instrument is a surgical instrument.

12. The instrument manipulator of claim 11, wherein the surgical instrument comprises jaws, a scissors, a grasper, a needle holder, a micro-dissector, a stapler, a tacker, a clip applier, a cutting blade, a cautery probe, an irrigator, a catheter, a suction orifice, or any combination of these.

13. The instrument manipulator of claim 1, further comprising an insertion mechanism configured to move the instrument manipulator proximally and distally relative to a manipulator assembly platform.

14. A robotic surgical system, comprising:
    a base;
    an arm assembly coupled to the base; and
    a manipulator assembly platform rotatably coupled to a distal portion of the arm assembly; and
    one or more instrument manipulators coupled to the manipulator assembly platform, each of the one or more instrument manipulators including:
      a frame comprising an outer shell and an inner frame, the inner frame being movably coupled to the outer shell;
      a plurality of actuator outputs protruding in a distal direction from the frame;
      an instrument support feature coupled to the outer shell; and
      a latching mechanism, the latching mechanism being configured to move the inner frame, the outer shell, or both relative to one another so as to operably engage the plurality of actuator outputs with a plurality of actuator inputs of an instrument supported by the instrument support feature.

15. The system of claim 14, comprising:
    one or more insertion mechanisms each coupling a corresponding one of the instrument manipulators to the manipulator assembly platform.

16. The system of claim 14, wherein the latching mechanism is configured to move the outer shell proximally relative to the inner frame to operably engage the plurality of actuator outputs with the plurality of actuator inputs while the instrument is supported by the instrument support feature.

17. The system of claim 14, wherein the latching mechanism is configured to move the outer shell distally relative to the inner frame to operably disengage the plurality of actuator outputs from the plurality of actuator inputs while the instrument is supported by the instrument support feature.

18. The system of claim 14, wherein the latching mechanism is configured to hold the inner frame stationary while moving the outer shell.

19. The system of claim 14, further comprising one or more insertion mechanisms configured to move the one or more instrument manipulators proximally and distally relative to the manipulator assembly platform.

20. A method of coupling a surgical instrument to a manipulator arm of a robotic surgical system, the method comprising:
- mounting the surgical instrument to an instrument manipulator coupled to the manipulator arm such that an instrument support feature of the instrument manipulator supports the surgical instrument, the instrument support feature being coupled to an outer shell of the instrument manipulator; and
- using a latching mechanism of the instrument manipulator to move an inner frame of the instrument manipulator, the outer shell, or both relative to one another such that a plurality of actuator outputs of the instrument manipulator operably engage with a plurality of actuator inputs of the instrument supported by the instrument support feature.

21. The method of claim 20, wherein the latching mechanism moves the outer shell relative to the inner frame while the inner frame is held stationary.

22. The method of claim 20, further comprising using the latching mechanism to move the instrument support feature distally relative to the inner frame to operably disengage the plurality of actuator outputs from the plurality of actuator inputs while the instrument is supported by the instrument support feature.

* * * * *